(12) United States Patent
VanTassel et al.

(10) Patent No.: US 7,727,189 B2
(45) Date of Patent: Jun. 1, 2010

(54) FILTER APPARATUS FOR OSTIUM OF LEFT ATRIAL APPENDAGE

(75) Inventors: Robert A VanTassel, Excelsior, MN (US); Robert G Hauser, Long Lake, MN (US); Robert Schwartz, Rochester, MN (US); David Holmes, Rochester, MN (US); Gregg S Sutton, Maple Grove, MN (US); Thomas E Borillo, Plymouth, MN (US); Jeffrey Welch, New Hope, MN (US)

(73) Assignee: Atritech, Inc., Plymouth, MN (US)

( * ) Notice: Subject to any disclaimer, the term of this patent is extended or adjusted under 35 U.S.C. 154(b) by 1069 days.

(21) Appl. No.: 10/644,388

(22) Filed: Aug. 19, 2003

(65) Prior Publication Data

US 2004/0127935 A1 Jul. 1, 2004

Related U.S. Application Data

(63) Continuation of application No. 09/697,628, filed on Oct. 26, 2000, now Pat. No. 6,652,556, which is a continuation-in-part of application No. 09/614,091, filed on Jul. 11, 2000, now Pat. No. 6,689,150, which is a continuation-in-part of application No. 09/428,008, filed on Oct. 27, 1999, now Pat. No. 6,551,303.

(60) Provisional application No. 60/196,454, filed on Apr. 11, 2000, provisional application No. 60/206,967, filed on May 25, 2000, provisional application No. 60/209,511, filed on Jun. 5, 2000, provisional application No. 60/211,896, filed on Jun. 16, 2000.

(51) Int. Cl.
A61M 29/00 (2006.01)

(52) U.S. Cl. .................................... 604/104

(58) Field of Classification Search ................ 604/104; 606/200, 1, 151, 108, 191; 623/1.1, 11.11
See application file for complete search history.

(56) References Cited

U.S. PATENT DOCUMENTS 178,283 A 6/1876 French ...................... 604/109

(Continued)

FOREIGN PATENT DOCUMENTS

WO WO 93/13712 7/1993

(Continued)

OTHER PUBLICATIONS

Dotter et al., "Transluminal Expandable Nitinol Coil Stent Grafting: Preliminary Report", *Radiology* vol. 147, No. 1, pp. 259-260, Apr. 1983.

(Continued)

*Primary Examiner*—Nicholas D Lucchesi
*Assistant Examiner*—Christopher D Koharski
(74) *Attorney, Agent, or Firm*—Beck & Tysver PLLC

(57) ABSTRACT

Apparatus for permanent placement across an ostium of a left atrial appendage in a patient, which includes a filtering membrane configured to extend across the ostium of the left atrial appendage. The filtering membrane has a permeable structure which allows blood to flow through but substantially inhibits thrombus from passing therethrough. The apparatus also includes a support structure comprising a plurality of fingers which are radially outwardly expandable with respect to a longitudinal axis to permanently engage the interior wall of the left atrial appendage, wherein the filtering membrane is attached to the support structure extending across the ostium of the left atrial appendage.

15 Claims, 38 Drawing Sheets

U.S. PATENT DOCUMENTS

| | | | |
|---|---|---|---|
| 1,967,318 A | 7/1934 | Monahan | 604/106 |
| 3,540,431 A * | 11/1970 | Mobin-Uddin Kazi | 128/899 |
| 3,844,302 A | 10/1974 | Klein | 135/26 |
| 3,874,388 A | 4/1975 | King et al. | 606/232 |
| 4,007,743 A | 2/1977 | Blake | 606/232 |
| 4,341,218 A | 7/1982 | Ü | 606/195 |
| 4,585,000 A | 4/1986 | Hershenson | 606/194 |
| 4,603,693 A | 8/1986 | Conta et al. | 227/179.1 |
| 4,665,906 A | 5/1987 | Jervis | 606/78 |
| 4,710,192 A | 12/1987 | Liotta et al. | 606/108 |
| 4,917,089 A | 4/1990 | Sideris | 606/215 |
| 4,921,484 A | 5/1990 | Hillstead | 604/104 |
| 5,037,810 A | 8/1991 | Saliba, Jr. | 514/56 |
| 5,041,090 A | 8/1991 | Scheglov et al. | 604/101.02 |
| 5,041,093 A | 8/1991 | Chu | 604/104 |
| 5,042,707 A | 8/1991 | Taheri | 606/213 |
| 5,053,009 A | 10/1991 | Herzberg | 604/104 |
| 5,064,435 A | 11/1991 | Porter | 623/23.7 |
| 5,078,736 A | 1/1992 | Behl | 623/1 |
| 5,108,420 A | 4/1992 | Marks | 606/213 |
| 5,171,259 A | 12/1992 | Inoue | 606/213 |
| 5,176,692 A | 1/1993 | Wilk et al. | 606/151 |
| 5,192,301 A | 3/1993 | Kamiya et al. | 606/213 |
| 5,256,146 A | 10/1993 | Ensminger et al. | 604/104 |
| 5,258,042 A | 11/1993 | Mehta | 600/36 |
| 5,284,488 A | 2/1994 | Sideris | 606/213 |
| 5,306,234 A | 4/1994 | Johnson | 604/49 |
| 5,334,217 A | 8/1994 | Das | 606/213 |
| 5,350,399 A | 9/1994 | Erlebacher et al. | 606/213 |
| 5,353,784 A | 10/1994 | Nady-Mohamed | 600/205 |
| 5,370,657 A | 12/1994 | Irie | 606/200 |
| 5,375,612 A * | 12/1994 | Cottenceau et al. | 128/899 |
| 5,417,699 A | 5/1995 | Klein et al. | 606/144 |
| 5,421,832 A | 6/1995 | Lefebvre | 264/173.11 |
| 5,425,744 A | 6/1995 | Fagan et al. | 606/213 |
| 5,433,727 A | 7/1995 | Sideris | 606/213 |
| 5,443,454 A | 8/1995 | Tanabe et al. | 604/264 |
| 5,451,235 A | 9/1995 | Lock et al. | 606/213 |
| 5,464,408 A | 11/1995 | Duc | 606/108 |
| 5,469,867 A | 11/1995 | Schmitt | 128/898 |
| 5,490,856 A | 2/1996 | Person et al. | 606/139 |
| 5,522,822 A | 6/1996 | Phelps et al. | 606/151 |
| 5,522,836 A | 6/1996 | Palermo | 606/200 |
| 5,527,322 A | 6/1996 | Klein et al. | 606/144 |
| 5,527,338 A | 6/1996 | Purdy | 606/200 |
| 5,591,196 A | 1/1997 | Marin et al. | 606/198 |
| 5,614,204 A | 3/1997 | Cochrum | 424/423 |
| 5,634,936 A | 6/1997 | Linden et al. | 606/213 |
| 5,634,942 A | 6/1997 | Chevillon et al. | 623/1 |
| 5,637,097 A | 6/1997 | Yoon | 604/176 |
| 5,643,292 A | 7/1997 | Hart | 606/144 |
| 5,649,953 A | 7/1997 | Lefebvre | 606/200 |
| 5,662,671 A | 9/1997 | Barbut et al. | 606/170 |
| 5,669,933 A | 9/1997 | Simon et al. | 600/200 |
| 5,681,347 A | 10/1997 | Cathcart et al. | 606/200 |
| 5,690,671 A | 11/1997 | McGurk et al. | 606/200 |
| 5,693,067 A | 12/1997 | Purdy | 606/200 |
| 5,695,525 A | 12/1997 | Mulhauser et al. | 623/11 |
| 5,702,421 A | 12/1997 | Schneidt | 606/213 |
| 5,709,224 A | 1/1998 | Behl et al. | 128/898 |
| 5,709,707 A | 1/1998 | Lock et al. | 606/213 |
| 5,725,552 A | 3/1998 | Kotula et al. | 606/213 |
| 5,725,568 A | 3/1998 | Hastings | 623/11.21 |
| 5,733,294 A | 3/1998 | Forber et al. | 606/151 |
| 5,735,290 A | 4/1998 | Sterman et al. | 128/898 |
| 5,749,883 A | 5/1998 | Halpern | 606/159 |
| 5,749,894 A | 5/1998 | Engelson | 606/213 |
| 5,766,219 A | 6/1998 | Horton | 606/191 |
| 5,769,816 A | 6/1998 | Barbut et al. | 604/96 |
| 5,776,097 A | 7/1998 | Massoud | 604/500 |
| 5,782,860 A | 7/1998 | Epstein et al. | 606/213 |
| 5,800,454 A | 9/1998 | Jacobsen et al. | 606/191 |
| 5,810,874 A | 9/1998 | Lefebvre | 606/200 |
| 5,823,198 A | 10/1998 | Jones et al. | 128/899 |
| 5,830,228 A | 11/1998 | Knapp et al. | 606/195 |
| 5,836,913 A | 11/1998 | Orth et al. | 604/107 |
| 5,836,968 A | 11/1998 | Simon et al. | 606/200 |
| 5,846,260 A | 12/1998 | Maahs | 606/200 |
| 5,846,261 A | 12/1998 | Kotula et al. | 606/213 |
| 5,849,005 A | 12/1998 | Garrison et al. | 606/1 |
| 5,851,232 A | 12/1998 | Lois | 623/1 |
| 5,855,597 A | 1/1999 | Jayaraman | 623/1 |
| 5,865,791 A | 2/1999 | Whayne et al. | 604/49 |
| 5,865,802 A | 2/1999 | Yoon et al. | 604/104 |
| 5,868,708 A | 2/1999 | Hart et al. | 604/104 |
| 5,876,367 A | 3/1999 | Kaganov et al. | 604/8 |
| 5,882,340 A | 3/1999 | Yoon | 604/164.12 |
| 5,885,258 A | 3/1999 | Sachdeva et al. | 604/530 |
| 5,895,399 A | 4/1999 | Barbut et al. | 606/159 |
| 5,904,703 A | 5/1999 | Gilson | 606/213 |
| 5,906,207 A | 5/1999 | Shen | 128/898 |
| 5,910,154 A | 6/1999 | Tsugita et al. | 606/200 |
| 5,911,734 A | 6/1999 | Tsugita et al. | 606/200 |
| 5,916,236 A | 6/1999 | Muijs Van de Moer et al. | 606/213 |
| 5,928,192 A | 7/1999 | Maahs | 604/96 |
| 5,928,260 A | 7/1999 | Chin et al. | 606/200 |
| 5,935,147 A | 8/1999 | Kensey et al. | 606/213 |
| 5,935,148 A | 8/1999 | Villar et al. | 606/213 |
| 5,941,249 A | 8/1999 | Maynard | 128/898 |
| 5,947,997 A | 9/1999 | Pavcnik et al. | 606/213 |
| 5,951,589 A | 9/1999 | Epstein et al. | 606/213 |
| 5,954,694 A | 9/1999 | Sunseri | 604/96 |
| 5,957,940 A | 9/1999 | Tanner et al. | 606/155 |
| 5,976,174 A | 11/1999 | Ruiz | 606/213 |
| 5,980,555 A | 11/1999 | Barbut et al. | 606/200 |
| 5,989,281 A | 11/1999 | Barbut et al. | 606/200 |
| 5,993,469 A | 11/1999 | McKenzie et al. | 606/159 |
| 5,997,557 A | 12/1999 | Barbut et al. | 606/159 |
| 6,007,523 A | 12/1999 | Mangosong | 604/284 |
| 6,007,557 A | 12/1999 | Ambrisco et al. | 606/200 |
| 6,010,517 A | 1/2000 | Baccaro | 606/151 |
| 6,010,522 A | 1/2000 | Barbut et al. | 606/200 |
| 6,024,754 A | 2/2000 | Engelson | 606/213 |
| 6,024,755 A | 2/2000 | Addis | 606/213 |
| 6,024,756 A | 2/2000 | Huebsch et al. | 606/213 |
| 6,027,520 A | 2/2000 | Tsugita et al. | 606/200 |
| 6,033,420 A | 3/2000 | Hahnen | 606/185 |
| 6,036,720 A | 3/2000 | Abrams et al. | 606/213 |
| 6,042,598 A | 3/2000 | Tsugita et al. | 606/200 |
| 6,048,331 A | 4/2000 | Tsugita et al. | 604/96 |
| 6,051,014 A | 4/2000 | Jang | 606/200 |
| 6,051,015 A | 4/2000 | Maahs | 606/200 |
| 6,056,720 A | 5/2000 | Morse | 604/96 |
| 6,063,070 A | 5/2000 | Eder | 606/1 |
| 6,068,621 A | 5/2000 | Balceta et al. | 604/500 |
| 6,074,357 A | 6/2000 | Kaganov et al. | 604/8 |
| 6,079,414 A | 6/2000 | Roth | 128/898 |
| 6,080,182 A | 6/2000 | Shaw et al. | 606/213 |
| 6,080,183 A | 6/2000 | Tsugita et al. | 606/213 |
| 6,083,239 A | 7/2000 | Addis | 606/200 |
| 6,132,438 A | 10/2000 | Fleischman et al. | 606/139 |
| 6,136,016 A | 10/2000 | Barbut et al. | 606/200 |
| 6,139,527 A | 10/2000 | Laufer et al. | 604/114 |
| 6,152,144 A * | 11/2000 | Lesh et al. | 128/898 |
| 6,161,543 A | 12/2000 | Cox et al. | 128/898 |
| 6,652,556 B1 * | 11/2003 | VanTassel et al. | 606/200 |
| 6,949,113 B2 * | 9/2005 | Van Tassel et al. | 606/200 |

FOREIGN PATENT DOCUMENTS

| | | |
|---|---|---|
| WO | WO 97/21402 | 6/1997 |
| WO | WO 97/28749 | 8/1997 |
| WO | WO 98/02100 | 1/1998 |

| WO | WO 98/17187 | 4/1998 |
| WO | WO 98/23322 | 6/1998 |
| WO | WO 99/05977 | 2/1999 |
| WO | WO 99/07289 | 2/1999 |
| WO | WO 99/08607 | 2/1999 |
| WO | WO 99/30640 | 6/1999 |
| WO | WO 00/27292 | 5/2000 |
| WO | WO 01/21247 | 3/2001 |

OTHER PUBLICATIONS

Cragg et al., "Nonsurgical Placement of Arterial Endoprostheses: A New Technique Using Nitinol Wire", *Radiology*, vol. 147, No. 1, pp. 261-263, Apr. 1983.

Cragg et al., "A New Percutaneous Vena Cava Filter", *ALJ*, 141:601-604, Sep. 1983.

Sugita et al., "Nonsurgical Implantation of a Vascular Ring Prosthesis Using Thermal Shape Memory Ti/Ni Alloy (Nitinol Wire)", *Trans. Am. Soc. Artif. Intern. Organs*, vol. XXXII, 30-34, 1986.

Ruttengberg, "Nonsurgical Therapy of Cardiac Disorders", *Pediatric Consult*, vol. 5, No. 2, pages not numbered, 1986.

Rashkind et al., "Nonsurgical Closure of Patent Ductus Arteriosus: Clinical Application of the Rashkind PDA Occluder System", *Circulation* 75, No. 3, 583-592, 1987.

Lock et al., "Transcatheter Umbrella Closure of the Congenital Heart Defects", *Circulation*, vol. 75, No. 3, 593-599, 1987.

Wessel et al., "Outpatient Closure of the patent ductus arteriosus", *Circulation*, vol. 77, No. 5, 1068-1071, 1998.

Lock et al., "Transcatheter Closure of Atrial Septal Defects", *Circulation*, vol. 79, No. 5, 1091-1099, May, 1989.

* cited by examiner

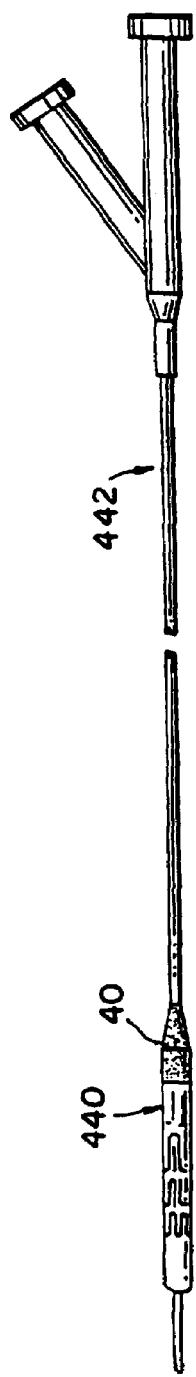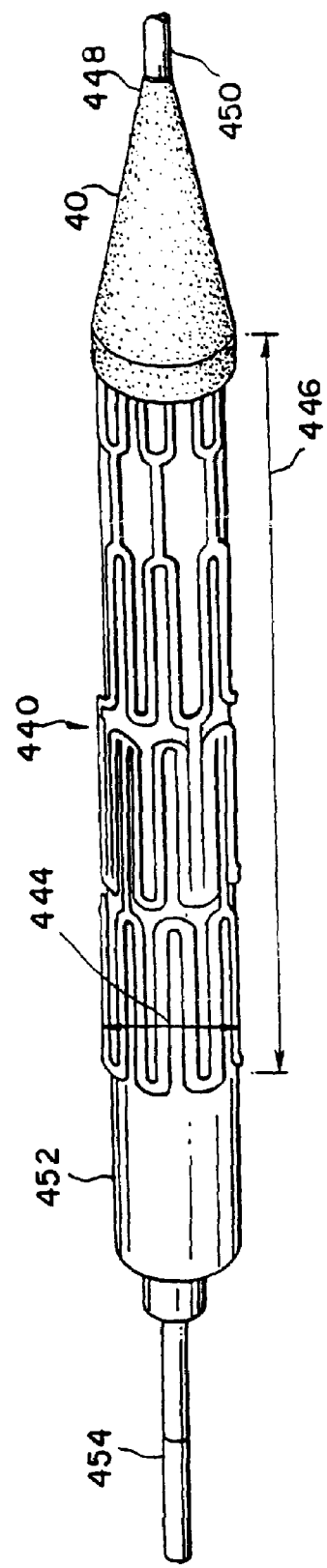

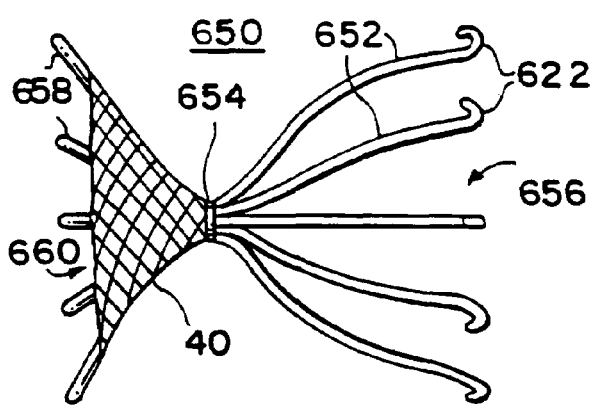
FIG.59
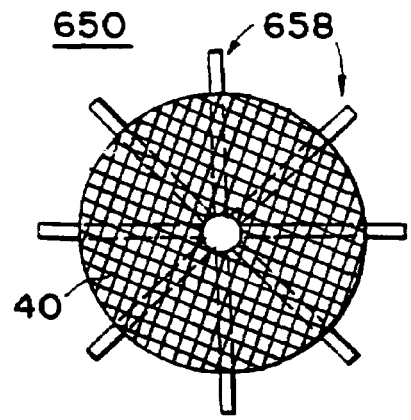
FIG.60
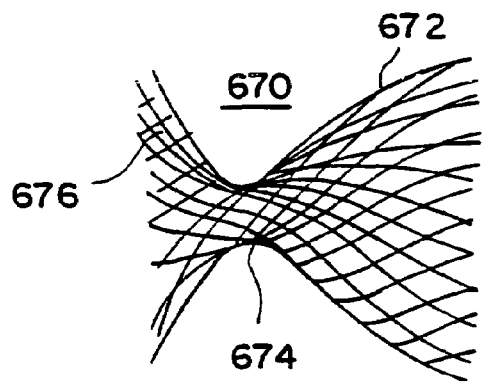
FIG.61
FIG.62
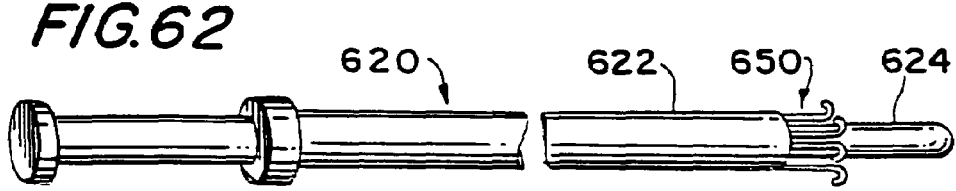
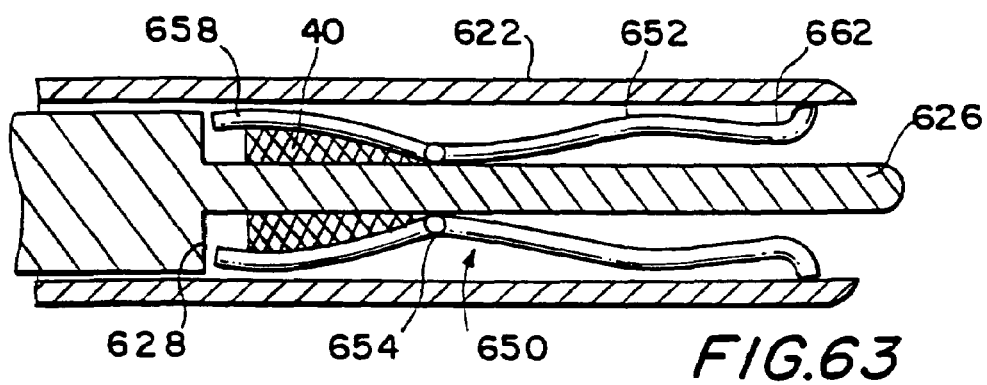
FIG.63

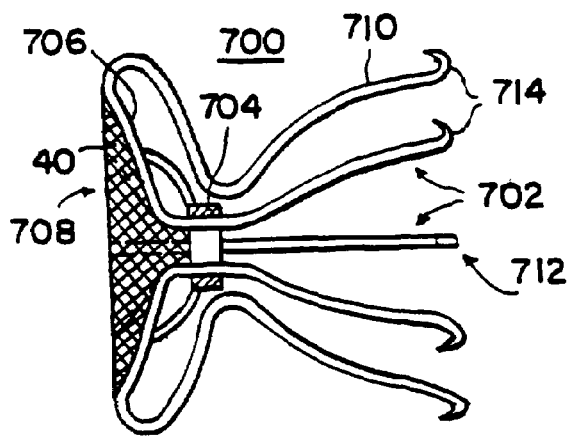
FIG. 66
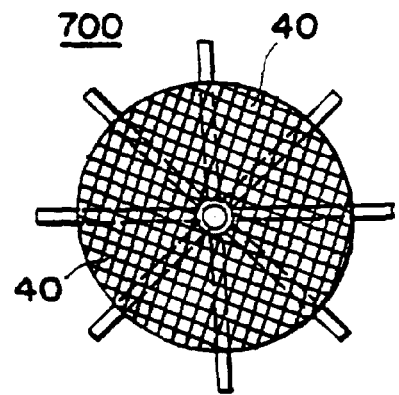
FIG. 67
FIG. 68
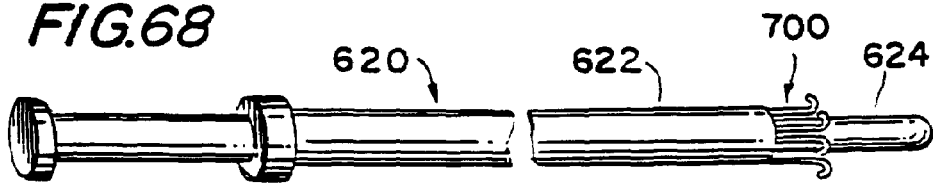
FIG. 69

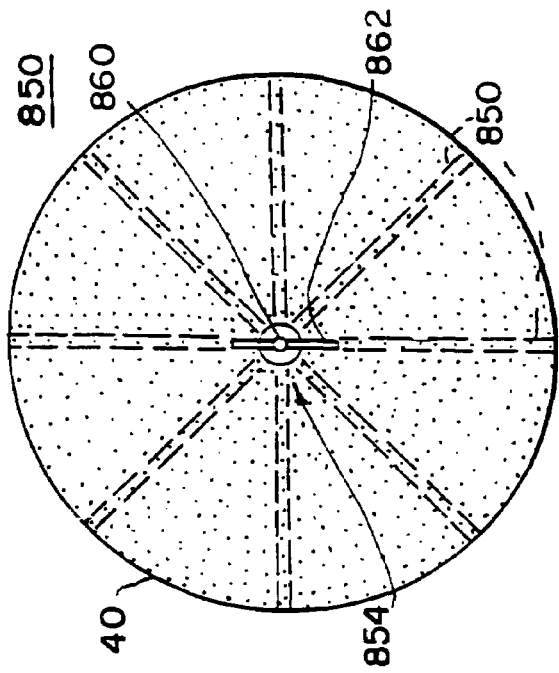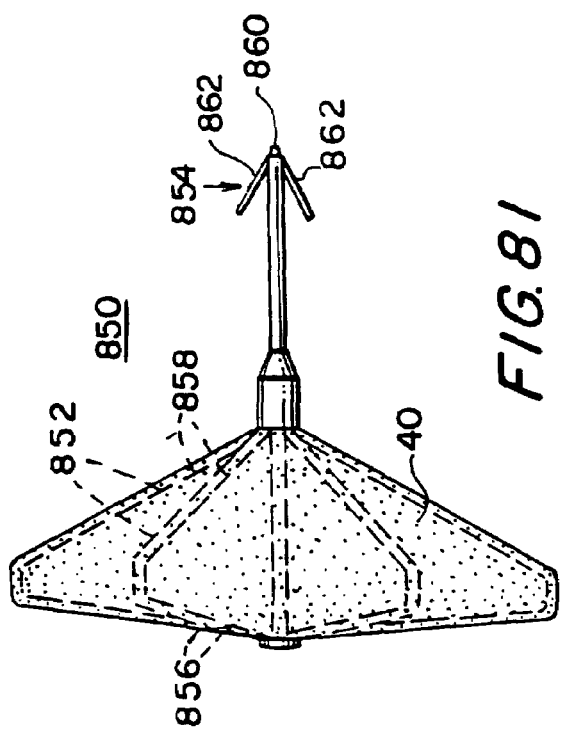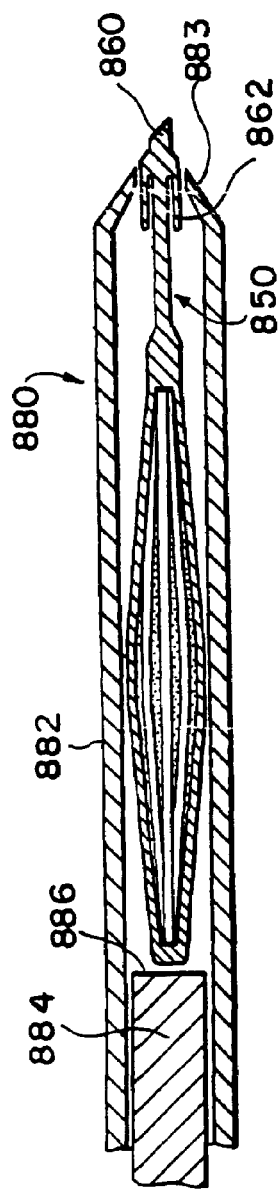

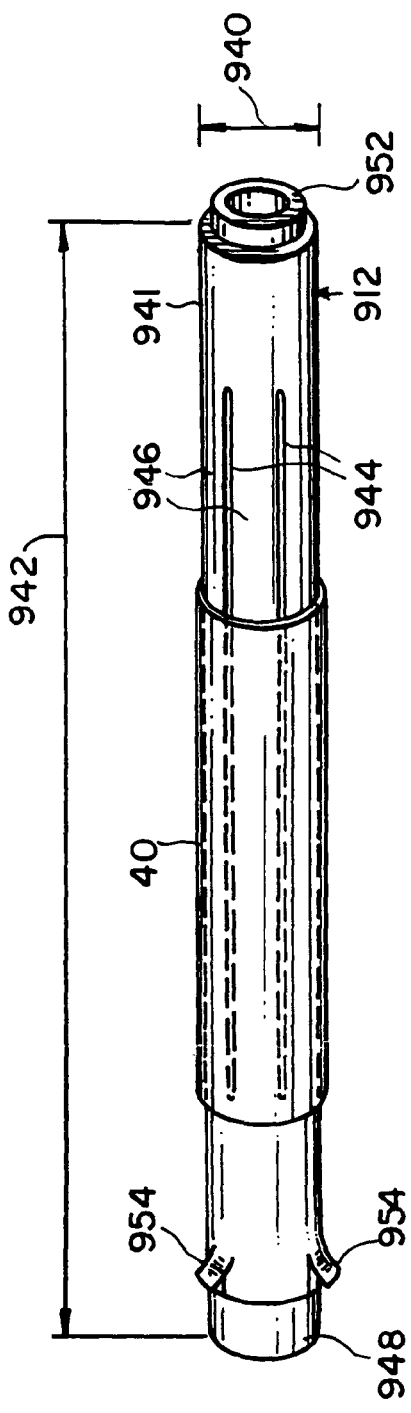
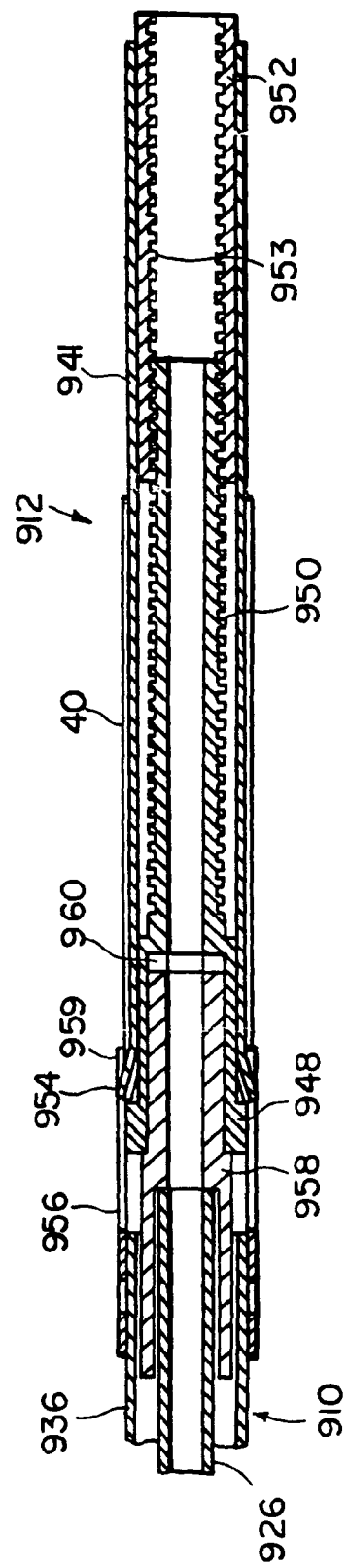
FIG.89
FIG.88

FILTER APPARATUS FOR OSTIUM OF LEFT ATRIAL APPENDAGE

This application is a continuation of application Ser. No. 09/697,628, filed Oct. 26, 2000, which is a continuation-in-part of application Ser. No. 09/614,091, filed Jul. 11, 2000, which is a continuation-in-part of application Ser. No. 09/428,008, filed Oct. 27, 1999, (now U.S. Pat. No. 6,551,303) all of which are incorporated by reference in their entirety herein. This application also claims the benefit of U.S. provisional application No. 60/196,454, filed Apr. 11, 2000, U.S. provisional application No. 60/206,967, filed May 25, 2000, U.S. provisional application No. 60/209,511, filed Jun. 5, 2000, and U.S. provisional application No. 60/211,896, filed Jun. 16, 2000, all of which are incorporated by reference in their entirety herein.

BACKGROUND OF THE INVENTION

1. Field of the Invention

The invention relates to a membrane structure applied to or across the ostium of an atrial appendage for filtering blood between an atrium of the heart and the associated atrial appendage or appendages to prevent a thrombus from leaving the atrial appendage while allowing blood flow through the membrane.

2. Description of the Related Art

There are a number of heart diseases (e.g., coronary artery disease, mitral valve disease) that have various adverse effects on the heart. An adverse effect of certain cardiac diseases, such as mitral valve disease, is atrial (or auricular) fibrillation. Atrial fibrillation may result in pooling of blood in the left atrial appendage. Blood pooling may also be spontaneous. When blood pools in the atrial appendage, blood clots can form and accumulate therein, build upon themselves, and propagate out from the atrial appendage into the atrium. These blood clots can then enter the systemic or pulmonary circulations and cause serious problems if they migrate from the atrial appendage and become free in the blood stream and embolize distally into the arterial system. Similar problems also occur when a blood clot extending from an atrial appendage into an atrium breaks off and enters the blood supply. Since blood from the left atrium and ventricle supply the heart and brain, blood clots from the atrial appendages can obstruct blood flow therein causing heart attacks, strokes or other organ ischemia. It is therefore necessary to find a means of preventing blood clots from forming in the atrial appendages and to prevent these blood clots, once formed, from leaving the atrial appendages to the heart, lungs, brain or other circulations of the patient which can cause heart attacks or strokes or other organ ischemia.

U.S. Pat. No. 5,865,791 relates to the reduction of regions of blood stasis and ultimately thrombus formation in such regions, particularly in the atrial appendages of patients with atrial fibrillation. More specifically, the '791 patent relates to procedures and devices for affixing the atrial appendages in an orientation that prevents subsequent formation of thrombus. In the '791 patent, the appendage is removed from the atrium by pulling on it and by putting a loop around it to form a sack of the atrial appendage and then cutting it off from the rest of the heart.

U.S. Pat. No. 5,306,234 relates to a method for surgically closing the passage between the atrium and the atrial appendage or severing the atrial appendage.

Other methods of treatment include surgically removing the atrial appendages to prevent blood stasis in the atrial appendages.

SUMMARY OF THE INVENTION

The invention provides a filtering membrane that allows blood to pass therethrough while substantially preventing blood clots formed in the atrial appendages from exiting therefrom. Such clots may cause heart attacks, strokes and other embolic events if allowed to leave the atrial appendage and enter the bloodstream.

The filtering membrane is permanently positioned across the ostium of the atrial appendage by a support structure attached to the filtering membrane. The filtering membrane filters blood flowing between the atrium and the left atrial appendage and effectively isolates blood clots from leaving the atrial appendage and entering the atrium. It may be larger than the ostium of the appendage, and extend over an area larger than the appendage ostium. It is percutaneously delivered to the ostium of the atrial appendage by a catheter and then may be expanded for positioning across or over the ostium and has a means to secure the filtering membrane across or over the ostium.

The filtering membrane itself is permeable to permit blood flow across the membrane. By allowing the such blood flow across the membrane, the porous structure minimizes any pressure gradient between the atrial appendage and the atrium in a controlled manner. The porous filtering membrane may eventually become infiltrated with cells. The permeable filtering membrane allows such tissue growth which may begin along the outer periphery of the structure. Such tissue growth minimizes uncontrolled leakage about the periphery of the filtering membrane and may assist in attachment of the filtering membrane to the ostium or surrounding tissue.

There are many means for fixing the filtering membrane in position across the ostium of the atrial appendage. The support structure for the filtering membrane may have a means for self-centering the filtering membrane over the appendage ostium. The filtering membrane may be glued to the wall of the atrial appendage adjacent the ostium, or the support structure may have wires, barbs, prongs or other methods of fixation which pass through the ostium and extend into or through the atrial appendage and which permanently engage an interior wall thereof. Alternatively, an anchor in the wall of the atrial appendage may be tethered to the filtering membrane for holding the filtering membrane in place. Springs may also extend between the anchor and the filtering membrane to hold the filtering membrane against the ostium. The filtering membrane may also be connected to a tether, elastic tether or spring and placed through the atrial appendage wall for holding the filtering membrane against the ostium and may pull on the atrial appendage such that its volume is reduced or eliminated, trapping and isolating blood clots therein.

Part of the device may involve a suction apparatus to remove clots that are already in place. The filtering membrane placement may require closure of an atrial septal defect created by the placement of this filter device about the appendage.

Alternatively, the filtering membrane may be held in place by a coiled spring which engages the interior wall of the atrial appendage.

The filtering membrane itself is permeable. The permeability of the filtering membrane allows blood to flow across, while inhibiting blood clots within the atrial appendage from exiting the atrial appendage into the bloodstream. In the case of a permeable filtering membrane, it may eventually become infiltrated with cells so that it may become a "living" structure, and can develop an endothelial/endocardial lining to enable it in turn to become a non-thrombogenic surface. It thus can develop an endothelium and with time become highly biocompatible. It may be coated or covered with an anticoagulant or other compounds, such as, for example, heparin, or it may be treated to prevent thrombus from forming on the filtering membrane surface, to extend its patency or until it is infiltrated with cells and/or develops an endothelial covering.

The device, when implanted in the atrial appendage, may also have the ability to perform electrical monitoring of the heart. This may include two or more electrical contacts placed apart on the device, and connected to signal conditioning circuitry for determination of cardiac features such as rhythm of the atria or ventricles. Another sensor on the device could measure pressure of the atria, atrial appendage, or ventricular end diastolic pressures (left or right) through the open mitral or tricuspid valves. A suitable telemetry system would be used to telemeter this important electrical and hemodynamic information non-invasively outside the patient. Also, memory could be present on the device in order to record the information for later recovery via noninvasive telemetry.

OBJECTS OF THE INVENTION

It is an object of the invention to provide a filter between the atrium and atrial appendage to prevent blood clots from flowing therebetween.

It is an object of the invention to provide a filter between the atrium and atrial appendage to allow blood flow across the filter, e.g., to reduce any hemodynamic pressure differential therebetween.

It is an object of the invention to provide a filter which is permanently implanted between the atrium and the atrial appendage by a support structure which substantially conforms to the contours of the ostium and the interior wall of the atrial appendage.

It is an object of the invention to reduce the volume of an atrial appendage to reduce the size of the region for potential blood stasis formation, and consequently the effective volume of the affected atrium.

It is an object of the invention to reduce the region of static blood in the atrial appendages and hence the thrombogenicity of the atrium.

It is an object of the invention to measure hemodynamics pressure (or flow), or electrical signals in the heart and telemeter them outside the body for diagnosis or monitoring.

It is an object of the invention to prevent blood clots from forming in the atrial appendages.

It is an object of the invention to position across the ostium of the atrial appendage a non-thrombogenic, biocompatible surface that prevents blood clots from forming.

It is an object of the invention to provide a permeable filtering membrane surface which may eventually become lined with endothelial or endocardial cells.

It is an object of the invention to isolate the atrial appendage from the atrium proper with respect to the passage of thrombus with a filtering membrane, while allowing communication through which blood may flow.

It is an object of the invention to minimally invasively prevent blood clots from forming in the atrial appendages and escaping therefrom.

It is an object of the invention to remove thrombi from the atrium via suction or other means.

It is an object of the invention to prevent thrombus by use of heparin, other antithrombogenic substances, or other compounds on or eluted from the filtering membrane.

It is an object of the invention to ensure the filtering membrane is centered across or over the ostium of the atrial appendage.

It is an object of the invention to accurately place the filtering membrane across or over the ostium of the atrial appendage.

Other objects, advantages and novel features of the present invention will become apparent from the following detailed description of the invention when considered in conjunction with the accompanying drawings.

BRIEF DESCRIPTION OF THE DRAWINGS

FIG. 29 illustrates another embodiment of the filtering membrane and apparatus for installing the filtering membrane in accordance with the invention.

FIG. 30 is an enlarged view of the filtering membrane and apparatus illustrated in FIG. 29 in accordance with the invention.

FIG. 59 illustrates a further embodiment of the apparatus in accordance with the invention.

FIG. 60 is an end view of the apparatus of FIG. 59 in accordance with the invention.

FIG. 61 illustrates a still further embodiment of the apparatus in accordance with the invention.

FIG. 62 illustrates additional apparatus for use with the apparatus of FIGS. 59-61 in accordance with the invention.

FIG. 63 is an enlarged sectional view of the apparatus of FIG. 59 in accordance with the invention.

FIG. 66 illustrates yet another embodiment of the apparatus in accordance with the invention.

FIG. 67 is an end view of the apparatus of FIG. 66 in accordance with the invention.

FIG. 68 illustrates additional apparatus for use with the apparatus of FIGS. 66-67 in accordance with the invention.

FIG. 69 is an enlarged sectional view of the apparatus of FIGS. 66 and 68 in accordance with the invention.

FIG. 81 illustrates a further embodiment of the apparatus in accordance with the invention.

FIG. 82 is a distal end view of the apparatus of FIG. 81 in accordance with the invention.

FIG. 83 is an enlarged sectional view of additional apparatus for use with the apparatus of FIGS. 81-82 in accordance with the invention.

FIG. 88 is an enlarged sectional view of a distal portion of the embodiment illustrated in FIG. 87 in accordance with the invention.

FIG. 89 is a perspective view of the embodiment illustrated in FIG. 88 in accordance with the invention.

DESCRIPTION OF THE PREFERRED EMBODIMENTS

Although atrial fibrillation may result in the pooling of blood in the left atrial appendage and the majority of use of the invention is anticipated to be for the left atrial appendage, the invention may also be used on the right atrial appendage and in general for placement across any aperture in the body in which blood is permitted to flow therethrough or therefrom but in which blood clots are substantially prevented from escaping from the atrial appendage and entering into the bloodstream.

Figure 4:
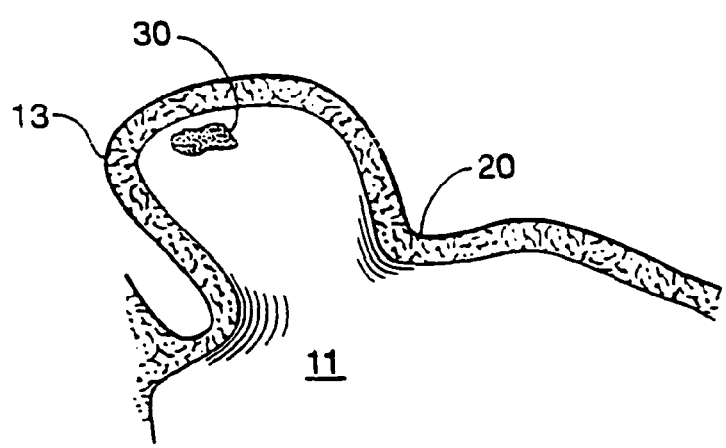
FIG. 4 is a partial cross sectional view of a portion of a heart showing an atrium and its associated atrial appendage.

As shown in FIG. 4, a thrombus, blood clot, or emboli 30 (collectively referred to as a thrombus) may occur from pooling of blood in the left atrial appendage 13 due to poor circulation of blood therein when the patient experiences atrial fibrillation. When blood pools in the left atrial appendage 13, thrombus 30 can accumulate therein, build upon itself, and propagate out from the left atrial appendage 13 into the left atrium 11, thus leaving the heart and entering the blood stream. Once in the bloodstream, such thrombus can block blood flow to the heart, brain, other organs, or peripheral vessels if it becomes lodged in the arteries thereof. Heart attack, a stroke, or ischemia may result.

To prevent thrombus 30 from forming in the left atrial appendage 13, or to prevent thrombus formed therein from leaving and entering the blood stream which may cause a heart attack, a stroke or ischemia, a filtering membrane 40 is permanently placed across the ostium 20 of the atrial appendage 13. The filtering membrane 40 can be made of bicompatible materials, such as, for example, ePFTE (e.g., Gortex®), polyester (e.g., Dacron®), PTFE (e.g., Teflon®), silicone, urethane, metal fibers, or other biocompatible polymers.

The filtering membrane 40 is a permeable filtering membrane, having pore sizes ranging from about 50 to about 400 microns. It is also contemplated that the pores may also be larger or smaller as indicated by the circumstances, provided such pores substantially inhibit thrombus from passing therethrough. The open area of the filtering membrane is preferably at least 20% of the overall surface area, although a range of about 25-60% may be preferred. The structure of the filtering membrane is preferably a two-dimensional screen, a cellular matrix, a woven or non-woven mesh, or the like. The filtering membrane may also be a permeable metal or a metal mesh of fine fibers. The filtering membrane may be coated or covered with an anticoagulant, such as heparin, or another compound, or treated to provide antithromogenic properties.

The porosity of the filtering membrane, described above, allows blood to flow therethrough while blocking or inhibiting the passage of thrombus, clots, or emboli formed within the atrial appendage from entering the atrium of the heart and, eventually, the patient's bloodstream.

The characteristic of allowing the flow of blood through the filtering membrane provides several advantages. For example, the left atrial appendage inherently contracts during normal cardiac function to force blood through the heart. These contractions result in blood flow through the ostium of the left atrial appendage. Allowing blood flow through the filtering membrane substantially reduces any pressure gradient that may exist between the appendage and the atrium.

The reduction of the pressure gradient may be helpful to the patient during recovery from the implantation of the filtering membrane structure in the atrial appendage. More particularly, the heart is able to more gradually adapt to the presence of the filtering membrane when blood is permitted to flow through the membrane, and consequently through the ostium of the left atrial appendage.

The filtering function also reduces the risk of leakage about the periphery of the filtering membrane, or of dislodgement of the filtering membrane that may result from the exertion of pressure against the surface of the filtering membrane. Allowing the blood flow across the filtering membrane may relieve this pressure, sufficiently and in a controlled manner, to reduce such leakage or dislodgement.

Tissue ingrowth may provide additional securement of the filtering membrane to the ostium. More particularly, the growth of tissue may occur along the outer periphery of the filtering membrane or supporting structure adjacent the ostium. This tissue growth, in cooperation with the pressure relief provided by the permeable structure, may provide additional means of reducing leakage about the periphery of the filtering membrane. Tissue growth may eventually cover additional surface area of the filtering membrane.

The filtering membrane 40 placed across or over the ostium 20 should be antithrombotic. In order to make the filtering membrane antithrombotic, heparin or other anticoagulants or antiplatelet agents may be used on the filtering membrane 40.

When permeable filtering membranes 40 are used, an ingrowth of cells may eventually cover the filtering membrane with endothelial cells. The endothelial cells present a smooth cellular wall covering the filtering membrane which prevents thrombosis from occurring at the filtering membrane.

The permeable filtering membrane 40 is permanently implanted across the ostium and retained in position by a support structure attached to the filtering membrane. As will be described herein, such permanent placement is achieved by aspects of the support structure which, for example, may engage and/or pierce the wall of the atrial appendage. Alternatively, such permanent placement may be achieved by the support structure which expands to engage either the ostium and/or the interior wall of the atrial appendage. Furthermore, the support structure may be configured to conform to the unique configuration of the ostium and/or the interior wall of the atrial appendage, and the filtering membrane held in position by the support structure to conform to the ostium.

Figure 1:
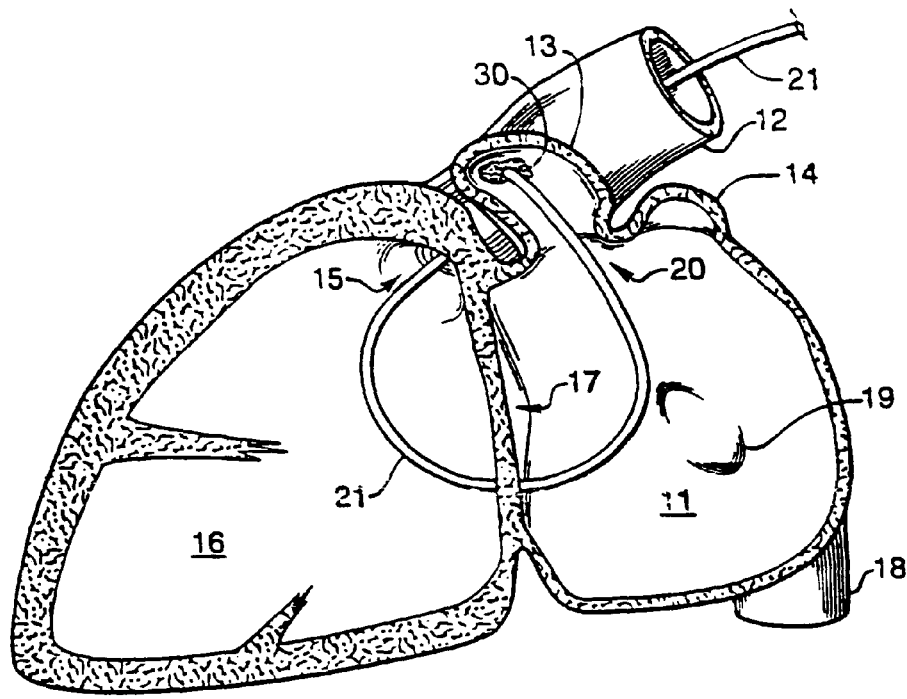
FIG. 1 is a partial cross sectional view of a heart showing a catheter entering the left atrial appendage using a retrograde procedure from the aorta in accordance with the invention.
Figure 2:
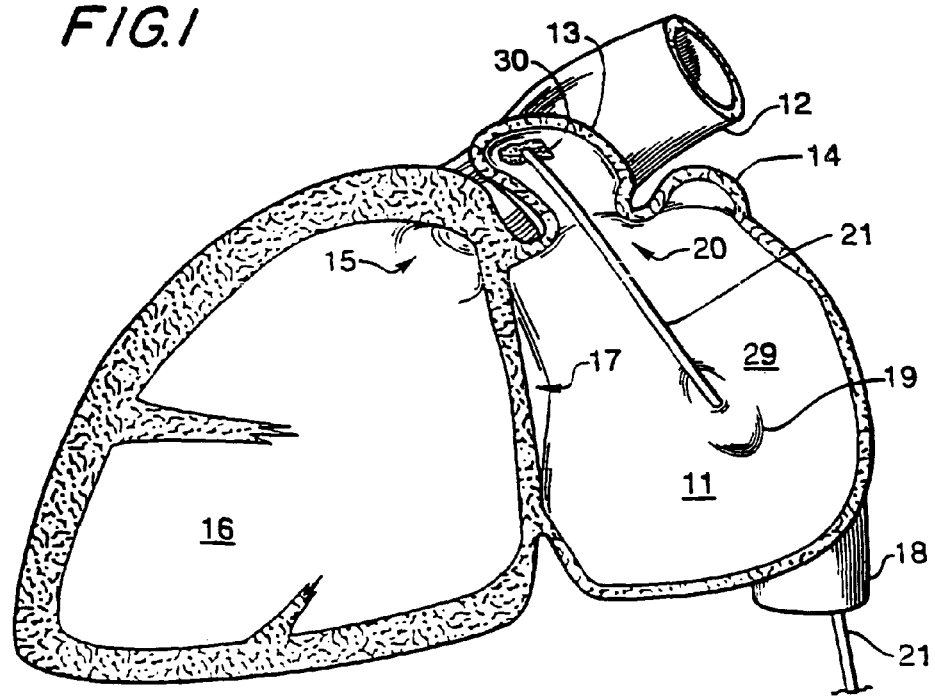
FIG. 2 is a partial cross sectional view of a heart showing a catheter entering the left atrial appendage using a transeptal procedure from the femoral vein or superior vena cava in accordance with the invention.

FIGS. 1 and 2 show a cross section of a human heart showing a thrombus 30 in the left atrial appendage 13. The figures also show the atrial appendage ostium 20 which is to have a filtering membrane 40 placed over it to prevent the thrombus 30 from escaping out of the atrial appendage 13 into the left atrium 11 and thus into the blood stream, which could cause a stroke, a heart attack or ischemia.

Figure 3:
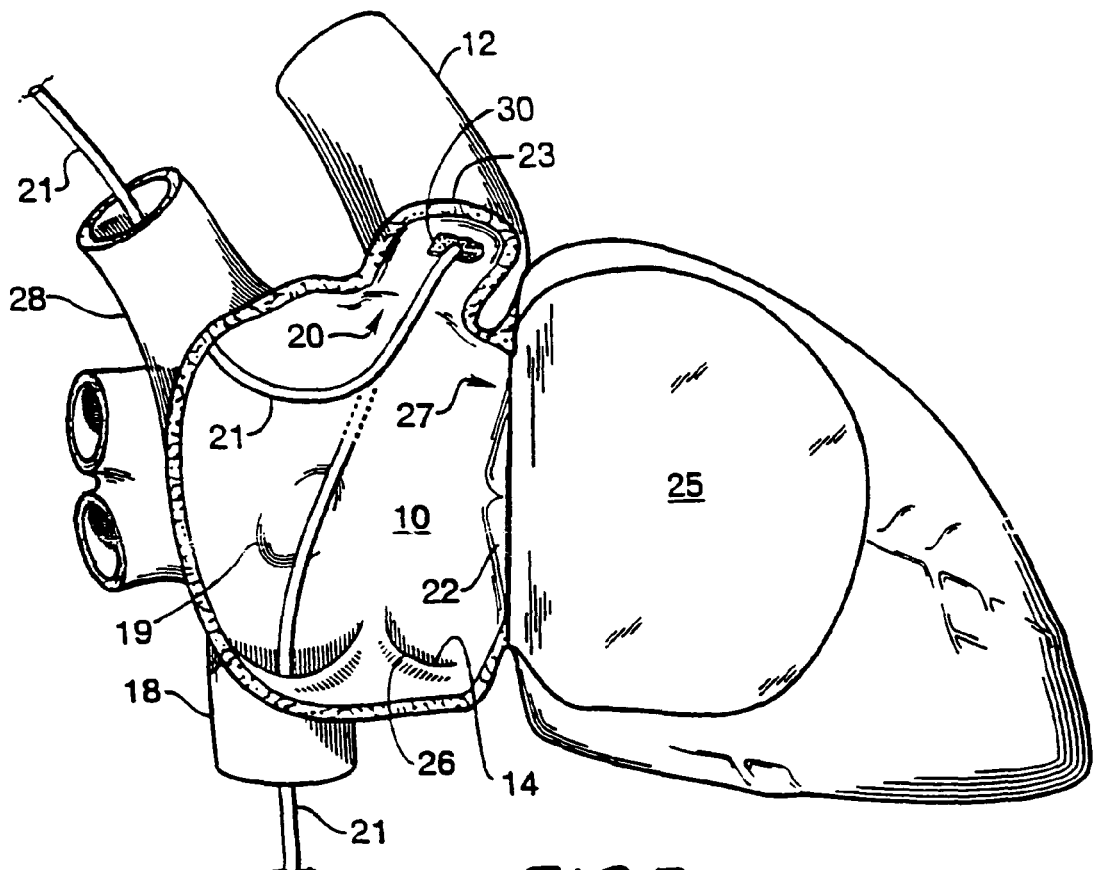
FIG. 3 is a partial cross sectional view of a heart showing a catheter entering the right atrial appendage from the jugular vein or optionally from the femoral vein in accordance with the invention.

FIG. 3 shows a cross section of a human heart showing a thrombus 30 in the right atrial appendage 23. The right atrial appendage 23 can be treated in the same manner as the left atrial appendage 13.

FIG. 4 shows a cross section of the left atrium 11, the ostium 20 and the left atrial appendage 13 having a thrombus 30 therein.

Figure 5:
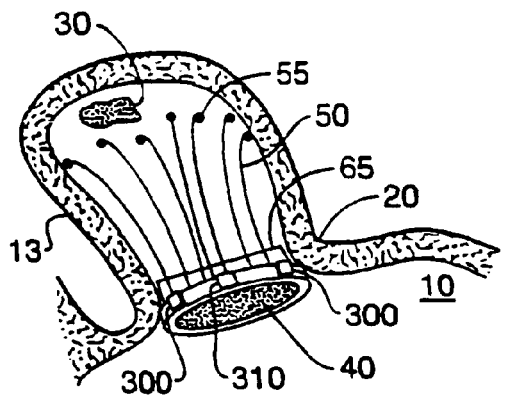
FIG. 5 is a partial cross sectional view of a portion of a heart showing an atrium and its associated atrial appendage with a permeable filtering membrane having flexible wire prongs with atraumatic bulbs to hold the filtering membrane in place and electronics built into the filtering membrane in accordance with the invention.

FIG. 5 shows a first embodiment of the invention having the permeable filtering membrane 40 and a plurality of flexible prongs 50 which may be made from a shape memory alloy, such as Nitinol®, for retaining a predisposed shape. The prongs 50 may be atraumatic so that they do not perforate the left atrial appendage 13. The prongs 50 may have atraumatic bulbs 55 on their tips so that the tips of the prongs 50 will not perforate the left atrial appendage 13. Nitinol® has the property of being able to be placed in a catheter in a compact configuration and then expanded when released from the catheter to a predetermined memory shape. The shape selected may be for the prongs 50 to curve around the lip of the ostium 20 and then hug the sides of the left atrial appendage 13. In this manner the filtering membrane 40 allows blood to flow through the ostium 20 but which blocks or substantially inhibits thrombus 30, clots or emboli from leaving the left atrial appendage 13 and entering the atrium, and eventually, the bloodstream of the patient.

The filtering membrane 40 is self centering across or over the ostium 20 of the left atrial appendage 13, by placing the prongs 50 in a circle around the filtering membrane 40 such that the prongs 50 fit against the wall of the left atrial appendage 13 of or within the lumen of the ostium 20 to center the filtering membrane 40 across or over the ostium 20. The filtering membrane 40 may also be centered by a centering rim 65 (see FIG. 6) attached to the back (appendage) side of the filtering membrane 40 that protrudes into the ostium 20 for centering. The centering rim 65 has a diameter of less than the diameter of the filtering membrane 40. The centering means may also consist of a series of centering cables 66 (see FIG. 11) which attach to a spring 90 or tether 85 from the centering rim 65 or the filtering membrane 40, to assure that centering occurs with placement.

Optionally electronics, such as sensors 300 and chips 310, built into the filtering membrane may be used to provide data about hemodynamic pressure, flow rates, temperature, heart rates, and electrical signals in the heart. When the filtering membrane is placed in the left atrial appendage 13 the sensors 300 may measure pressures in the atria or atrial appendage. The sensors may also measure ventricular end diastolic pressures through the open mitral or cuspid valves. Other information about the heart may be gathered such as noise from accelerometers to detect leakage, valve efficiency, activity levels of the patient and other noise related data. The sensors 300 may also be blood oxygen sensors. The chip 310 may use telemetry to transmit the information gathered by the sensors 300 and processed or stored by the chip 310 to receiving devices to aid in the treatment of the patient.

Figure 6:
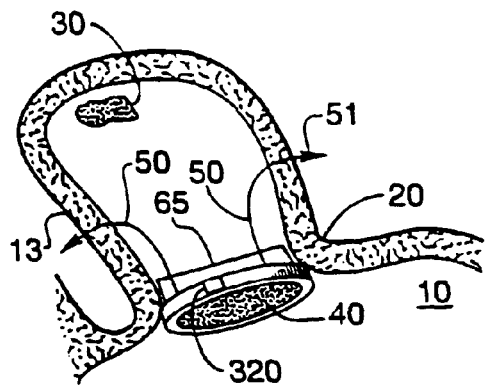
FIG. 6 is similar to FIG. 5 with the atraumatic bulbs removed so that the flexible wire prongs may puncture the atrium wall and secure the filtering membrane to the atrial appendage and a centering rim added to the filtering membrane in accordance with the invention.

In FIG. 6 the protective bulbs 55 are removed from the flexible prongs 50 of FIG. 5 such that flexible prongs 50 puncture the walls of the left atrial appendage 13 and secure the filtering membrane 40 in place. The flexible prongs 50 may penetrate into the atrial appendage wall or extend through the atrial appendage wall. The prongs may have barbed ends 51 to prevent the prongs from withdrawing from the atrial appendage wall.

As described above, filtering membrane 40 has a permeable structure which allows blood to flow therethrough but which blocks or substantially inhibits thrombus, clots or emboli from entering the atrium, and eventually, the bloodstream of the patient. The filtering membrane 40 has centering rim 65 attached for centering the filtering membrane in the ostium 20 and marker 320 in the filtering membrane 40 for observing the position of the filtering membrane while it is being inserted. The marker may be used for x-ray or ultrasound observation.

Although Nitinol® was cited above as a type of shape memory alloy prong material which can be used, any type memory alloy may be used. Such alloys tend to have a temperature induced phase change which will cause the material to have a preferred configuration when heated above a certain transition temperature. Other metals which may be used as prongs include corrosion resistant spring metals such as Elgiloy® or spring tempered steel.

Figure 7:
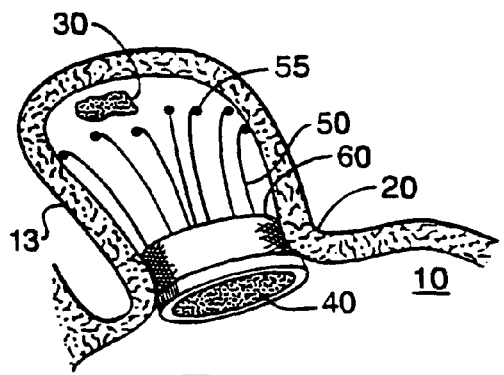
FIG. 7 is a partial cross sectional view of a portion of a heart as in FIG. 5 with a support portion between the filtering membrane and the prongs in accordance with the invention.

Another embodiment of the invention is shown in FIG. 7. It is similar to the embodiment shown in FIG. 5. The embodiment in FIG. 7 has a support structure 60 attached to the filtering membrane 40 for expanding in the ostium 20 helping to secure the filtering membrane 40 thereto. The prongs 50 operate in the same manner as in FIG. 5 hugging the inner walls of the left atrial membrane 13 to secure the filtering membrane 40 across the ostium 20. As described above, filtering membrane 40 has a permeable structure which allows blood to flow therethrough but which blocks or substantially inhibits thrombus, clots or emboli from entering the atrium, and eventually, the bloodstream of the patient. The support structure 60 may also be made from Nitinol®, Elgiloy® or another expandable spring loaded or balloon expandable material.

The filtering membrane 40 may be self centering across or over the ostium 20 of the left 13 atrial appendage, by placing the support structure 50 into the ostium wherein the support structure plugs the ostium with the filtering membrane 40 centered in the support structure. Further the prongs 50 fit against the wall of the left atrial appendage 13 of or within the lumen of the ostium 20 to center the filtering membrane 40 across or over the ostium 20.

Figure 8:
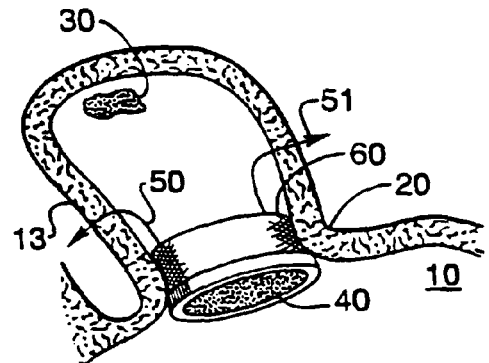
FIG. 8 is similar to FIG. 7 with the atraumatic bulbs removed so that the flexible wire prongs may puncture the atrium wall and secure the filtering membrane to the atrial appendage in accordance with the invention.

In FIG. 8 the protective bulbs 55 are removed from the flexible prongs 50 of FIG. 7 such that flexible prongs 50 puncture the walls of the left atrial appendage 13 and secure the filtering membrane 40 in place. The flexible prongs 50 may penetrate into the atrial appendage wall or extend through the atrial appendage wall. The prongs may have barbed ends 51 to prevent the prongs from withdrawing from the atrial appendage wall. As described above, filtering membrane 40 has a permeable structure which allows blood to flow therethrough but which blocks or substantially inhibits thrombus, clots or emboli from entering the atrium, and eventually, the bloodstream of the patient.

Figure 9:
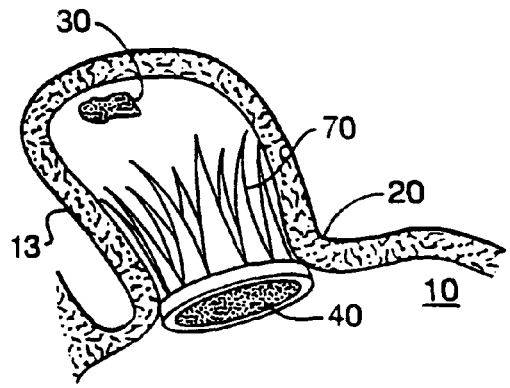
FIG. 9 is a partial cross sectional view of a portion of a heart showing an atrium and its associated atrial appendage with a permeable filtering membrane having a large expandable support portion to hold the filtering membrane in place in accordance with the invention.

In the embodiment shown in FIG. 9 a larger expandable support structure 70 is used to both engage the sides of the ostium 20 and hug the inside walls of the left atrial appendage 13. Again the support structure may be made of Nitinol®, Elgiloy® or other material which may be delivered in a catheter and expanded to the proper size and shape to securely hold the filtering membrane 40 across or over the ostium 20 which allows blood to flow through filtering membrane 40 but which blocks or substantially inhibits thrombus 30, clots or emboli from entering the atrium, and eventually, the bloodstream of the patient.

Figure 10:
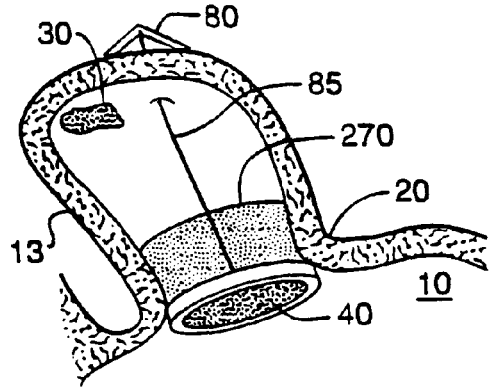
FIG. 10 is a partial cross sectional view of a portion of a heart showing an atrium and its associated atrial appendage having an anchor and a tether to hold the filtering membrane in place in accordance with the invention.

FIG. 10 shows another embodiment of the invention wherein the filtering membrane 40 is secured across the ostium 20 by means of an anchor 80 which is driven into or through the wall of the left atrial appendage 13 and secured therein by the surface area of the anchor so that it will not pull out of or through the wall of the left atrial appendage 13 or cause embolism from the left atrial appendage 13. A tether 85 is attached to the anchor 80 and to the filtering membrane 40 to secure the filtering membrane 40 snuggly against the ostium 20. Filtering membrane 40 has a permeable structure which permits unclotted blood to flow through the filtering membrane. A contrast medium 270, such as radiographic contrast or a similar substance, may be introduced into the left atrial appendage 13 by injection through a catheter after the filtering membrane 40 is in place. The device delivery catheter itself may have a port for this injection. The port may also be used to inject the contrast medium 270 that can be immediately visualized, and examined for diagnostic purposes. In prior art devices, the introduction of the contrast medium 270 into the left atrial appendage 30 may increase the volume of fluid within the appendage and, consequently, the hemodynamic pressure exerted against the walls of the atrial appendage and against any membrane or structure that may be used to occlude the atrial appendage. The filtering membrane 40 allows blood and contrast medium 270 to flow therethrough, and therefore may equalize hemodynamic pressure between the atrium and the left atrial appendage 30 in a controlled manner. The contrast medium may be used with any of the embodiments of the invention.

Figure 11:
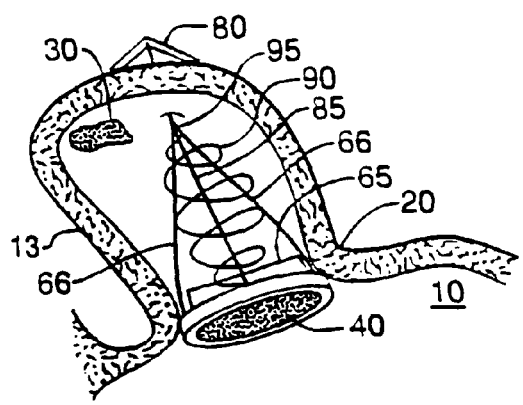
FIG. 11 is a partial cross sectional view of a portion of a heart showing an atrium and its associated atrial appendage having an anchor and a spring to hold the filtering membrane in place, a centering rim on the filtering membrane and a centering cable in accordance with the invention.
Figure 12:
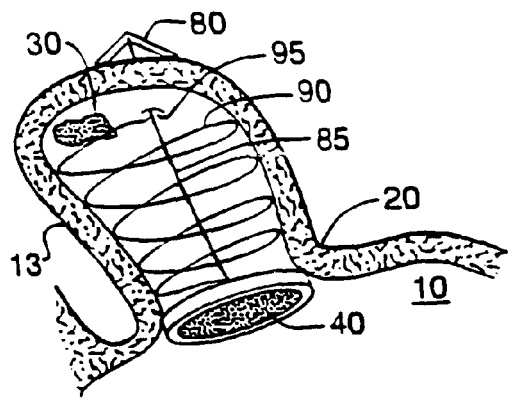
FIG. 12 is the same as FIG. 11 with the spring filling the atrium to help hold the filtering membrane in place in accordance with the invention.

FIG. 11 shows another embodiment of the invention wherein filtering membrane 40 has a spiral spring 90 in addition to the anchor 80. The spiral spring 90 can be used in conjunction with or separately from the tether 85 to pull the filtering membrane 40 against the ostium 20. Although a spiral spring 90 has been shown in FIG. 11 the shape used may be oval, cylindrical, oblong, or other shape to connect the anchor 80 to the filtering membrane 40. In another embodiment shown in FIG. 12 the spiral spring 90 may fill the volume of the left atrial appendage 13 securing the filtering membrane 40 to the ostium 20. The spiral spring 90 filling the left atrial appendage 13 may also have an anchor 80 and tether 85 to help secure the filtering membrane 40 to the ostium 20. Alternatively centering rim 65 may be used as shown in FIG. 11 to center the filtering membrane 40 over ostium 20 of left atrial appendage 13. Centering cables 66 connected to spring 90 and either filtering membrane 40 or centering rim 65 may also be used to center the filtering membrane 40 across or over the ostium 20.

Figure 13:
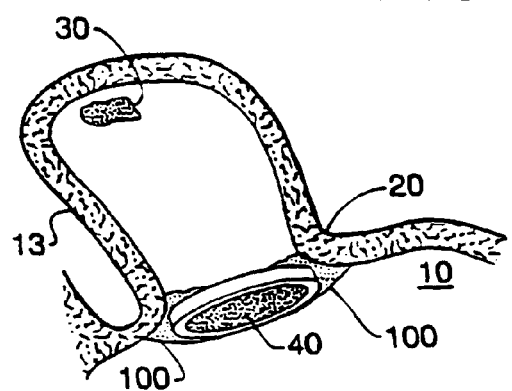
FIG. 13 is a partial cross sectional view of a portion of a heart showing an atrium and its associated atrial appendage with the filtering membrane adhesively being held in place in accordance with the invention.

FIG. 13 shows yet another means of securing the filtering membrane 40 across or over the ostium 20. In this embodiment filtering membrane 40 is directly attached to the ostium 20 by an adhesive 100.

Figure 14:
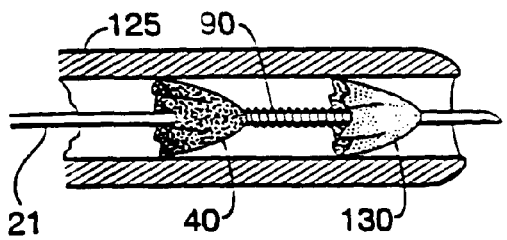
FIG. 14 is a partial cross sectional view of a delivery catheter having a disk, a spring and filtering membrane therein in accordance with the invention.
Figure 15:
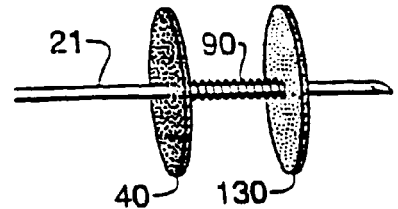
FIG. 15 is a schematic view of a disk, spring and filtering membrane after being expanded out of the delivery catheter of FIG. 11 in accordance with the invention.

FIG. 14 shows a delivery catheter 125 containing a collapsed permeable filtering membrane 40 and a collapsed disk 130 connected to the permeable filtering membrane 40 by a spring 90 on catheter 21. The disk 130 may be made of a flexible woven metal or a flexible woven metal with a thin permeable polymer sandwiched inside. Disk 130 may also be a polymer weave. The disk 130 is flexible and compresses or folds so it fits into the delivery catheter 125 and expands to its desired shape after release from the delivery catheter 125. Similarly, filtering membrane 40 compresses or folds to fit into the delivery catheter 125 and expands to its desired shape after release. FIG. 15 shows the permeable filtering membrane 40, disk 130 and spring 90 from FIG. 14 in an expanded configuration outside of the delivery catheter 125.

FIG. 15 shows the spring 90 connecting the permeable filtering membrane 40 and the disk 130 for urging them together. In other embodiments an elastic tether or a tether with teeth and a pawl on the permeable filtering membrane 40 to form a ratchet can also be used to pull the permeable filtering membrane 40 and the disk 130 together.

Figure 16:
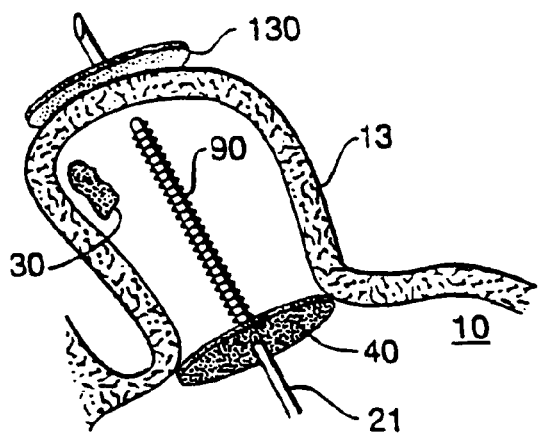
FIG. 16 is a partial cross sectional view of a portion of a heart showing an atrium and its associated atrial appendage having a disk, a filtering membrane and a spring therebetween in accordance with the invention.

FIG. 16 shows the device of FIG. 15 applied to the left atrial appendage 13 having thrombus 30. After the device is applied, the spring 90 pulls the disk 130 toward the permeable filtering membrane 40, collapsing the left atrial appendage 13 and trapping the thrombus 30 therein as shown in FIG. 17.

Figure 17:
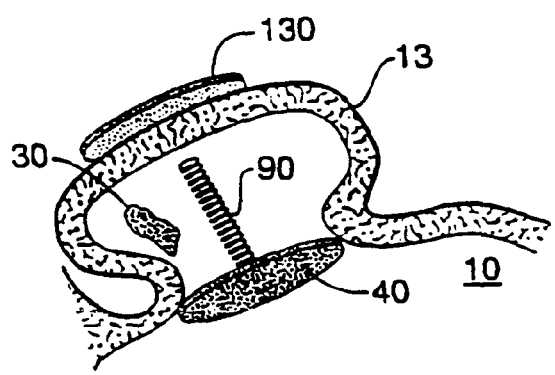
FIG. 17 is a partial cross sectional view of a portion of a heart showing an atrium and its associated atrial appendage shown in a collapsed position in accordance with the invention.
Figure 18:
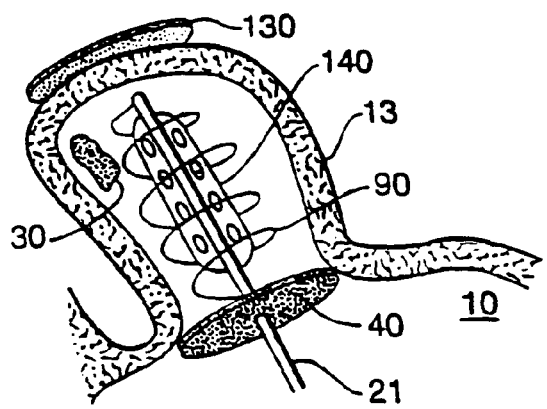
FIG. 18 is a partial cross sectional view of a portion of a heart showing an atrium and its associated atrial appendage having a disk, a spring, a filtering membrane and vacuum in the catheter in accordance with the invention.

FIG. 18 shows an alternate embodiment of the device in FIGS. 16 and 17 wherein the catheter 21 is equipped with a vacuum 140 for sucking out blood and thrombosis 30 found in the left atrial appendage 13. The vacuum 140 will help collapse the left atrial appendage 13 such that spring 90 need not be as large as in FIG. 16.

Figure 19:
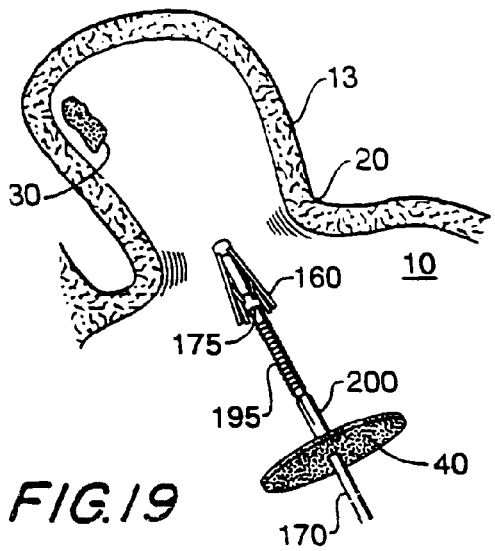
FIG. 19 is a partial cross sectional view of a portion of a heart showing an atrium and its associated atrial appendage showing an umbrella folded for entering the atrial appendage in accordance with the invention.
Figure 20:
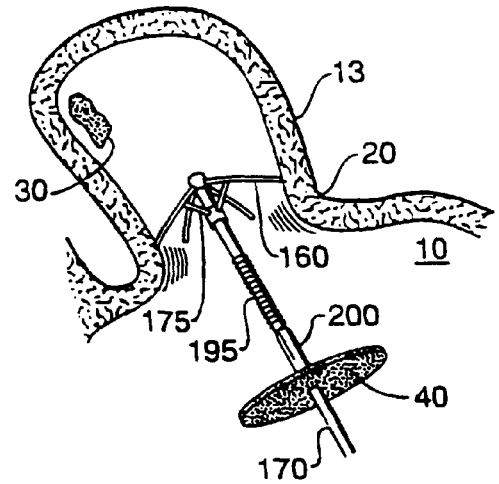
FIG. 20 is a partial cross sectional view of a portion of a heart showing an atrium and its associated atrial appendage showing the umbrella opened in the atrial appendage to secure the umbrella into the wall of the atrial appendage in accordance with the invention.
Figure 21:
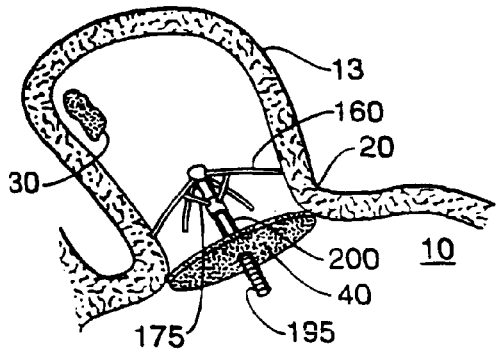
FIG. 21 is a partial cross sectional view of a portion of a heart showing an atrium and its associated atrial appendage showing the umbrella and filtering membrane positioned across the ostium of the atrial appendage in accordance with the invention.

FIGS. 19-21 show another embodiment of the invention using an umbrella principle for securing the filtering membrane 40 against the ostium 20. FIG. 19 shows closed umbrella struts 160 entering the ostium 20 of left atrial appendage 13. The filtering membrane 40 is some distance back from the umbrella struts 160 at the bottom of the range of teeth 195 on pole 170. FIG. 20 shows the umbrella struts inside of the left atrial appendage 13 with the struts 160 open. Umbrella opening structure 175 on pole 170 pushes the struts out to the umbrella open position. The umbrella opening structure 175 can be pushed to the open position or have a spring loaded mechanism to push the struts 160 to the open position. The ends of the umbrella struts 160 engage the left atrial appendage wall around the ostium 20 and prevent the umbrella from being withdrawn from the left atrial appendage 13. The ends of the umbrella struts 160 that engage the atrial appendage wall may be blunted or have bulbs on the tips or have padding so as not to puncture the left atrial appendage 13. FIG. 21 shows the filtering membrane 40 drawn up against the ostium 20 by ratcheting the filtering membrane along pole 170. The pawl mechanism 200 engages teeth 195 on pole 170 and is moved forward to snugly position the filtering membrane 40 across the ostium 20.

Figure 22:
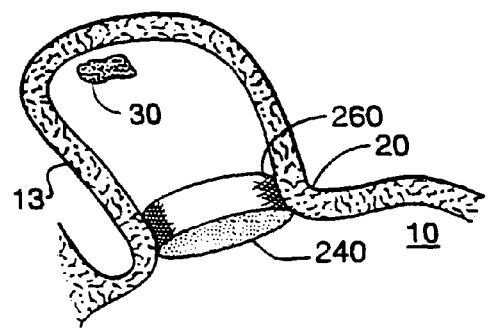
FIG. 22 is a partial cross sectional view of a portion of a heart showing an atrium and its associated atrial appendage showing a support portion having a filtering membrane positioned across the ostium of the atrial appendage in accordance with the invention.

FIG. 22 shows a support structure 260 applied to the ostium 20 of left atrial appendage 13. The support structure 260 expands after leaving a delivery catheter such that the wall of the support structure secures the support structure by pressure to the ostium 20. Filtering membrane 240 folds or is compressed into the delivery catheter and expands as the support structure 260 expands and lodges in the ostium 20 of the left atrial appendage 13.

Figure 23:
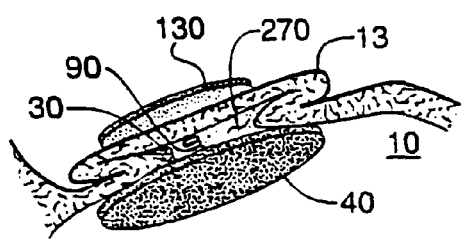
FIG. 23 is a partial cross sectional view of a portion of a heart showing an atrium and its associated atrial appendage showing the atrial appendage reduced to a minimum volume by a disk and spring squeezing the appendage against a filtering membrane in accordance with the invention.

FIG. 23 shows the left atrial appendage 13 compressed such that the volume of the atrial appendage is reduced to almost nothing. With the volume reduced the atrial appendage will not have a large volume of blood which can produce a thrombus. In the embodiment shown disk 130 and spring 90 pull the left atrial appendage 13 toward filtering membrane 40. Although FIG. 23 shows the use of a disk 130 and spring 90 to act on the left appendage, any method to reduce the volume of the atrial appendage as much as possible may be used.

As shown in FIG. 23 the filtering membrane 40 is much larger than the ostium 20. The oversized filtering membrane 40 may alternatively be used in all embodiments to ensure that the ostium 20 is completely covered. The filtering membrane 40 has a permeable structure which allows blood to flow therethrough, but which blocks or substantially inhibits thrombus, clots or emboli from entering the atrium, and eventually, the bloodstream of the patient.

Figure 24:
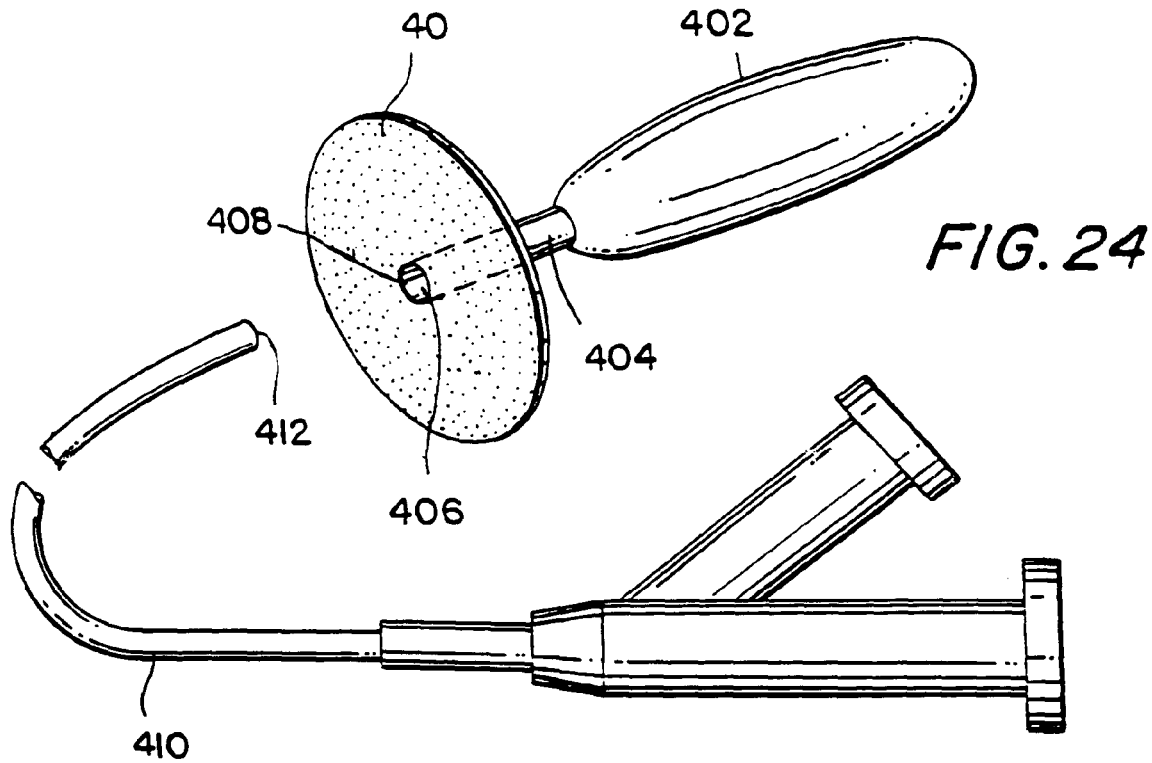
FIG. 24 is a perspective view of another embodiment of a filtering membrane and apparatus for installing the filtering membrane in accordance with the invention.
Figure 25:
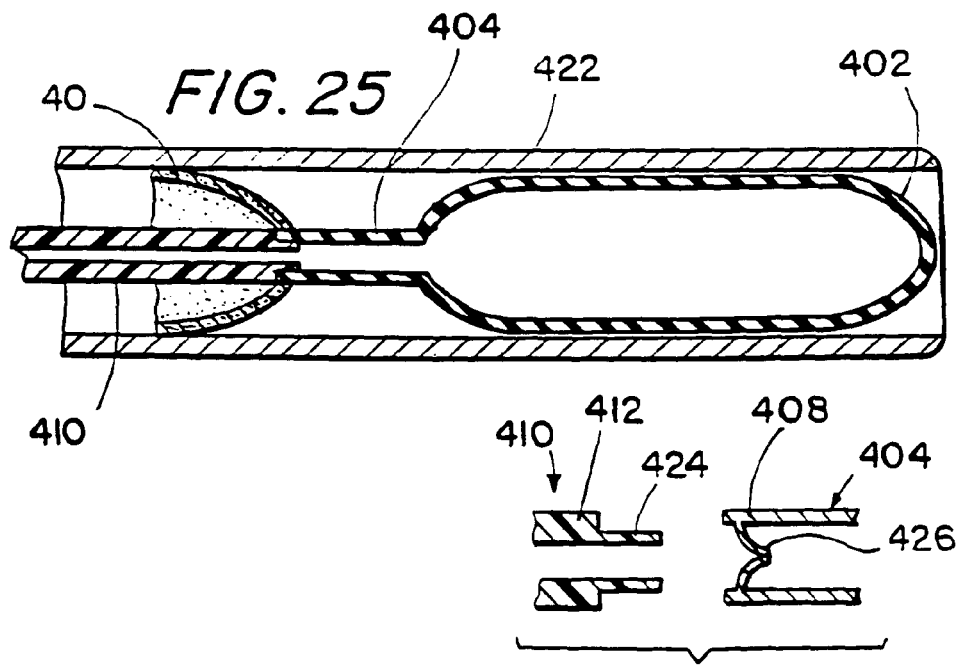
FIG. 25 is a sectional view of the filtering membrane and apparatus illustrated in FIG. 24, in accordance with the invention.

FIGS. 24-28 show another embodiment of the invention wherein the filtering membrane 40 is retained in position across the ostium 20 by an expandable structure, such as balloon structure 402. As illustrated in FIG. 25, balloon structure 402 may be manufactured from polymeric materials or similar materials known in the art. Tube 404 communicates with the internal cavity of balloon structure 402 for introducing saline or other appropriate fluid into the balloon structure 402. Filtering membrane 40 is attached to tube 404 in any appropriate manner, such as adhesive, sutures, or other means, and is provided with an aperture 406 which permits access to an end portion of tube 404, which acts as a balloon introduction port 408 to allow the introduction of fluid into the balloon structure 402.

FIG. 24 also illustrates a structure for introducing fluid into the balloon structure 402, such as catheter apparatus 410. Catheter apparatus 410 includes an outlet port 412 at its distal end portion for ejecting fluid from the catheter apparatus 410. Outlet port 412 may be connected to the balloon introduction port 408, which in turn communicates with the internal lumen of tube 404 and the interior of balloon structure 402.

Figure 26:
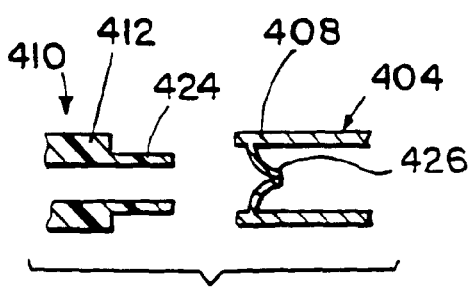
FIG. 26 is an enlarged view of a portion of the apparatus of FIG. 25 in accordance with the invention.

FIG. 25 illustrates the filtering membrane 40, the balloon structure 402, the tube 404, together with the catheter 410 attached to the tube 404, in a compacted configuration within a delivery tube 422. More particularly, balloon structure 402 is in its collapsed state and filtering membrane 40 is flexible and compressed or folded to fit into the delivery tube 422. Filtering membrane 40 is designed to expand into a disc-like shape after release from tube 422. FIG. 26 illustrates the certain structures pertinent to the interconnection of catheter 410 with tube 404. More particularly, outlet port 412 of catheter 410 may be provided with narrow tube 424 which is received within balloon introduction port 408 and maintains a valve 426 in an open position when outlet port 412 is connected to inlet port 408. When outlet port 412 is removed from balloon introduction port 408, valve 426 may close to prevent fluid from leaving balloon structure 402, as shown in FIG. 26.

Delivery tube 422 may be introduced into the venous or arterial system at an appropriate location, and advanced to into the atrium of the heart with appropriate steering and visualization apparatus (not shown).

Figure 27:
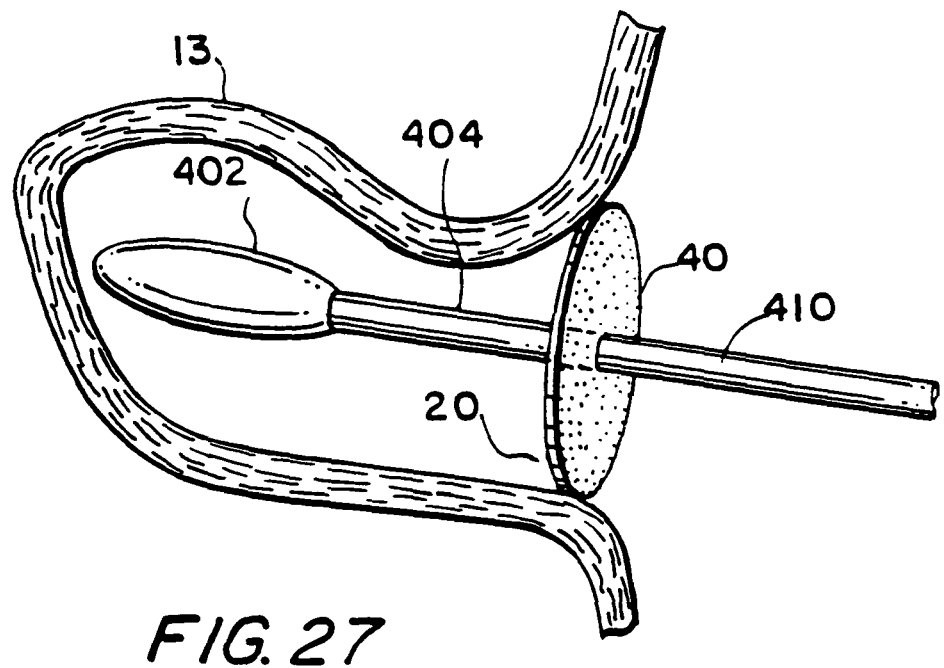
FIG. 27 is a partial cross-sectional view illustrating an early stage in the installation of the apparatus of FIG. 24, in accordance with the invention.
Figure 28:
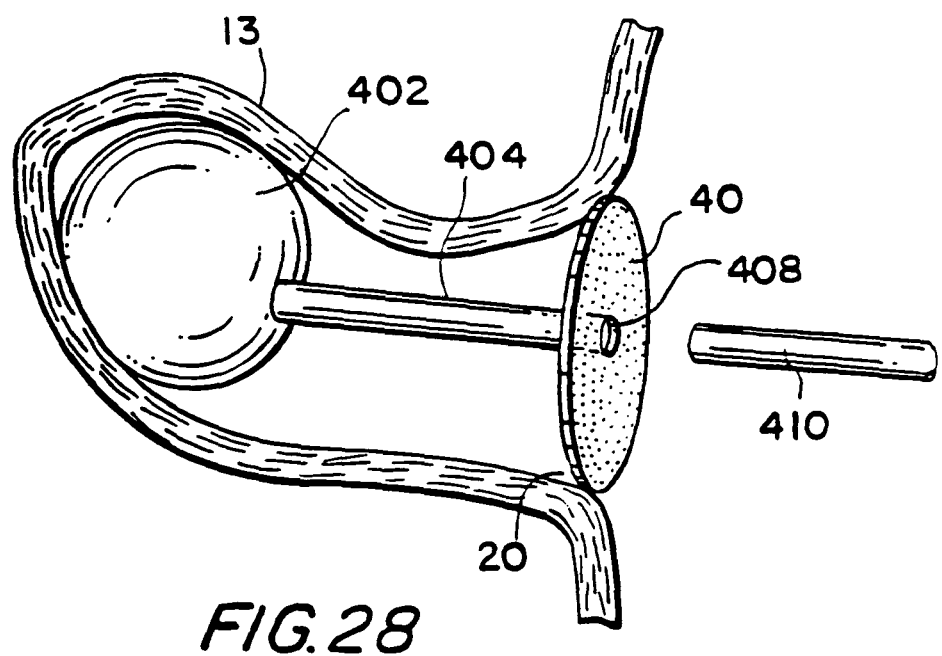
FIG. 28 is a partial cross-sectional view similar to FIG. 27, illustrating a later stage in the procedure in accordance with the invention.

FIG. 27 illustrates a later stage in the installation procedure wherein the filtering membrane 40, the balloon structure 402, the tube 404, and the catheter 410 have been advanced from the delivery tube 422 (not shown in FIG. 27). The balloon structure 402 is positioned within the left atrial appendage 13 such that the filtering membrane 40 is positioned about the ostium 20. Fluid is subsequently introduced into the catheter 410 which passes through tube 404 to expand the balloon structure 402, as illustrated in FIG. 28. The balloon structure 402 expands within the atrial appendage 13 and secures the filtering membrane 40 in position. The valve mechanism 426 (not shown in FIG. 28) of balloon introduction port 408 prevents the fluid from passing out of the balloon structure 402 when the catheter 410 is detached from the balloon port 408 and subsequently removed from the atrium. As described above, filtering membrane 40 has a permeable structure which allows blood to flow therethrough but which blocks or substantially inhibits thrombi, clots or emboli from exiting the atrial appendage 13, and entering the bloodstream of the patient.

FIGS. 29-40 illustrate yet another embodiment for attaching the filtering membrane across the ostium 20 of the left atrial appendage 13. FIG. 29 illustrates the filtering membrane 40, the attachment apparatus 440 for securing the filtering membrane 40 across the ostium 20 of the atrial appendage 13, and catheter apparatus 442 for installing the attachment apparatus 440 and filtering membrane 40. As FIG. 30 illustrates, attachment apparatus 440 and filtering membrane 40 may be initially in a compacted configuration. Attachment apparatus 440 is preferably an expandable tubular apparatus having an initial diameter 444 of about 1-3 mm and an initial length 446 of about 0.5-6 cm. Attachment apparatus is preferably manufactured from a flexible material such as stainless steel, nitinol, nylon, polyester, PET, or polyethylene.

Filtering membrane 40 is attached to attachment apparatus 440 at the proximal end thereof, in a loosely fitted, somewhat conical configuration and defines a central opening 448, which allows the catheter 450 of catheter apparatus 442 to pass through membrane 40, as will be described in greater detail herein. Alternatively, filtering membrane 40 may also cover a greater portion of the length 446 of the attachment apparatus 440, or filtering membrane 40 may cover the entire attachment apparatus 440 in a substantially sock-like fashion. Filtering membrane 40 may be fabricated from a material that also has elastic characteristics which may expand from a first size to a second size.

Catheter 450 supplies expansion fluid, such as saline or contrast medium, into expandable structure, such as balloon structure 452, which is positioned within the interior lumen of attachment apparatus 440 in order to radially expand attachment apparatus 440 when it is positioned within the atrial appendage 13. Balloon structure 452 may include a distal, atraumatic tip portion 454, e.g., a flexible helical coil or soft plastic tip.

Figure 31:
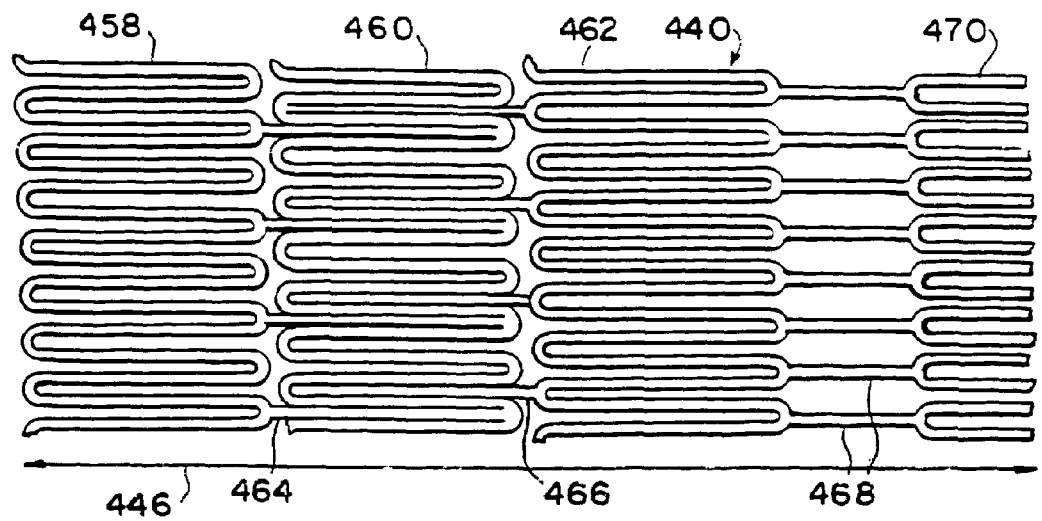
FIG. 31 is a planar development of the apparatus for attaching the filtering membrane illustrated in FIGS. 29-30 in accordance with the invention.
Figure 32:
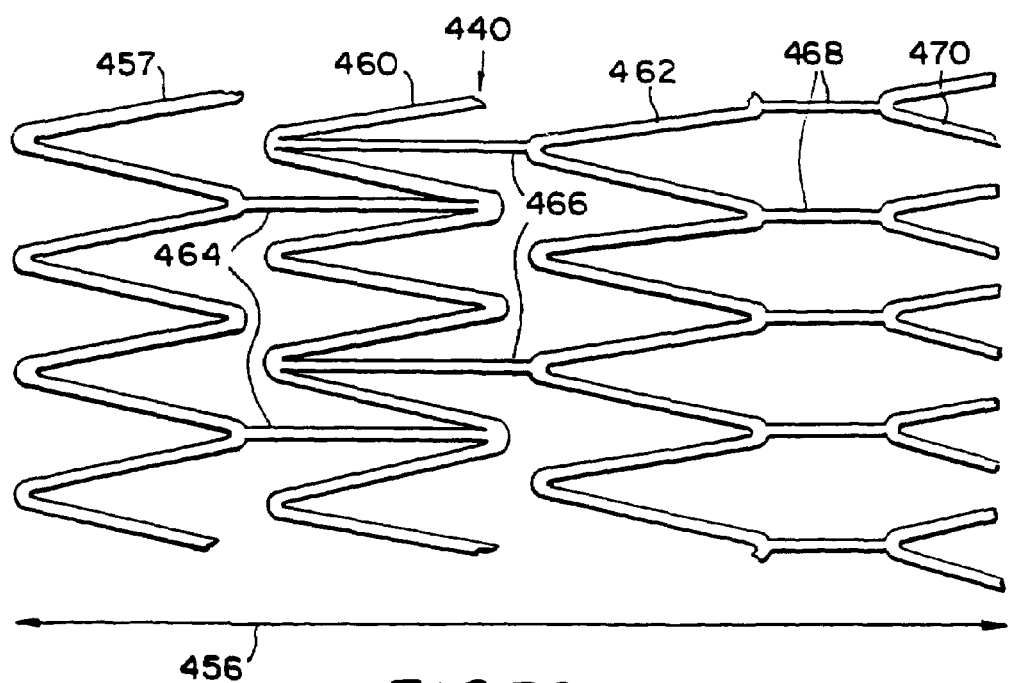
FIG. 32 is a planar development of the apparatus depicted in FIG. 31 in an expanded configuration, in accordance with the invention.

FIGS. 31 and 32 illustrate planar developments of attachment apparatus 440. The structure of attachment apparatus 440 preferably allows the length 446 of the apparatus in its initial configuration (FIG. 31) to remain substantially constant with respect to the length 456 in its expanded configuration (FIG. 32). In order to achieve this expansion while maintaining substantially constant length, attachment apparatus 440 is provided with a configuration having several serpentine segments 458, 460, and 462. Adjacent serpentine segments are interconnected by a plurality of longitudinal struts, e.g., rings 457 and 460 are interconnected by struts 464 and rings 460 and 462 are interconnected by struts 466. A plurality of U-shaped members 470 at the distal end portion of apparatus 440 provide an attachment point for the filtering membrane 40.

Figure 33:
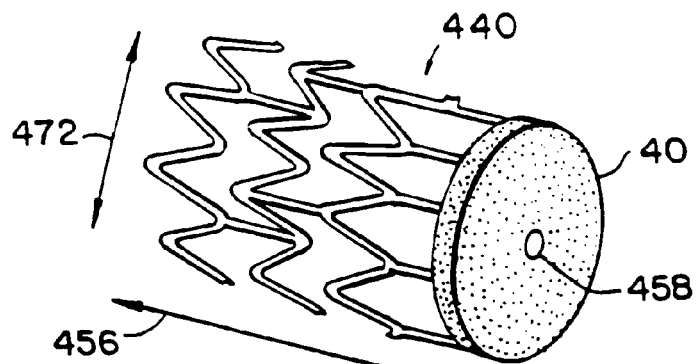
FIG. 33 is a perspective view of the filtering membrane and apparatus for attaching the filtering membrane of FIG. 30, illustrated in an expanded configuration in accordance with the invention.

FIG. 33 illustrates attachment member 440 in an expanded configuration, wherein length 456 remains substantially constant with respect to the length 446 of the configuration illustrated in FIG. 30. Diameter 472 is substantially larger than diameter 444 (FIG. 30) in order to secure filtering membrane 40 with the atrial appendage 13, as will be described herein.

FIGS. 34-37 illustrate several embodiments of the filtering membrane 40. As described above, catheter 450 passes through opening 458 in filtering membrane 40 in order to supply expansion fluid to expandable balloon structure 452. After balloon structure 452 has expanded the attachment apparatus 440 to the expanded configuration illustrated in FIG. 33, it may be necessary to remove balloon structure 452 by passing the balloon structure 452 proximally through filtering membrane 40, and more particularly, through opening 458. The embodiments of filtering membrane 40 illustrated in FIGS. 34-37 may facilitate the passage of balloon structure 452, or other interventional devices therethrough.

Figure 34:
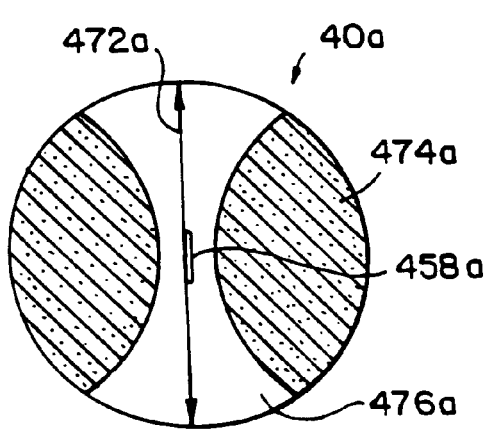
FIG. 34 is an elevational view of an embodiment of the filtering membrane in accordance with the invention.
Figure 35:
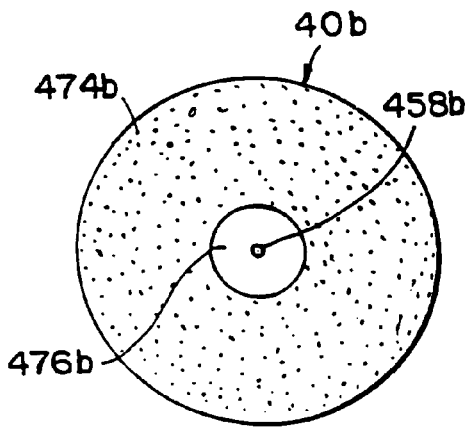
FIG. 35 is an elevational view of another embodiment of the filtering membrane in accordance with the invention.
Figure 36:
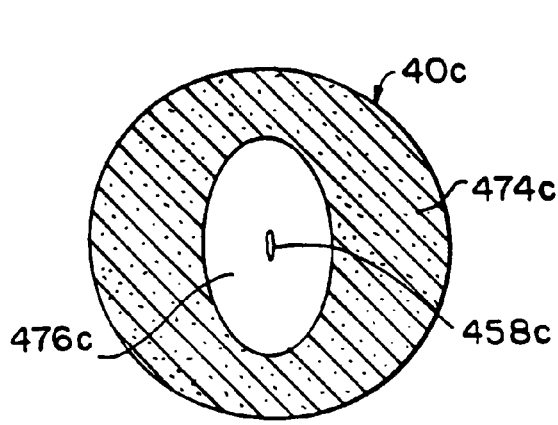
FIG. 36 is an elevational view of yet another embodiment of the filtering membrane in accordance with the invention.
Figure 37:
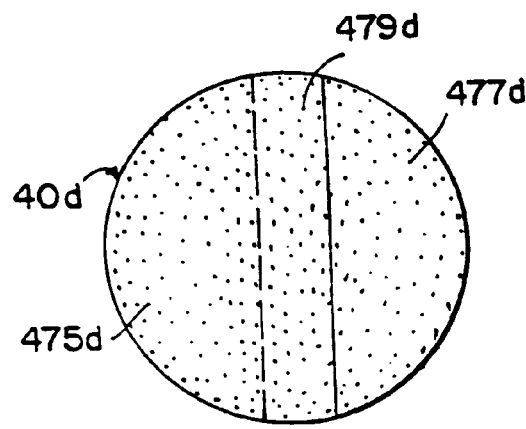
FIG. 37 is an elevational view of a further embodiment of the filtering membrane in accordance with the invention.

FIG. 34 illustrates filtering membrane 40a having a composite construction comprising filtering section 474a and elastic section 476a. The filtering section 474a is fabricated from a filtering material that provides the function of filtering the blood to allow the blood to pass therethrough while blocking or substantially inhibiting the passage of clots, thrombus or emboli therethrough, as described above. The elastic section 476a is fabricated from an elastic material, e.g., silicone, urethane or other similar material, that stretches to enlarge opening 458a to allow the balloon structure 452 or other intervention devices, such as, e.g., wires, catheters or the like, to pass therethrough and to subsequently return to its initial size. The initial size of aperture 458a provides similar characteristic to inhibit clots, thrombus or emboli from passing through 458a as filtering material of filtering section 474a. In this configuration, elastic material 476a extends substantially across the entire diameter 472a of the filtering membrane 40a.

Filtering membrane 40b (FIG. 35) is constructed with a filtering section 474b (i.e., the same material as filtering section 474a) and an elastic section 476b (i.e., the same elastic material as elastic section 476a). In filtering membrane 40b, the filtering section 474b substantially concentrically surrounds the elastic section 476b. The elastic section 476b is provided with an opening 458b that expands to allow the balloon structure 452 or other interventional devices to pass therethrough and to return to initial size in order to provide substantially the same characteristic of inhibiting the passage of thrombus, clots and emboli from passing therethrough as the filtering material of the filtering section 474b.

Filtering membrane 40c (FIG. 36) is constructed with a filtering section 474c (i.e., the same material as filtering section 474a) and an elastic section 476c (i.e., the same elastic material as elastic section 476a). In filtering membrane 40c, the filtering section 474c substantially concentrically surrounds an elastic section, such as substantially elliptical section 476c. The elastic section 476c is provided with an aperture, such as a slit 458c that expands to allow the balloon structure 452 or other interventional devices to pass therethrough and to return to initial size to provide substantially the same characteristic of inhibiting the passage of thrombus, clots and emboli from passing therethrough as the filtering material of the faltering section 474b.

Filtering membrane 40d (FIG. 37) may be fabricated from the same material as filtering section 474a, above, in several sections, such as sections 475d and 477d, which overlap at region 479d to form an opening therethrough for balloon structure 452 or other interventional devices. It is further contemplated that three or more sections of filtering material may be used in an overlapping configuration, in a manner similar to, for example, the "aperture" configuration of an optical device. The balloon structure 452 may be passed through the opening between sections 475d and 477d. After the balloon structure 452 is removed, the overlapping structure substantially closes the opening and provides substantially the same characteristic of inhibiting the passage of thrombus, clots and emboli from passing therethrough as the filtering material of the filtering sections 475d and 477d.

Figure 38:
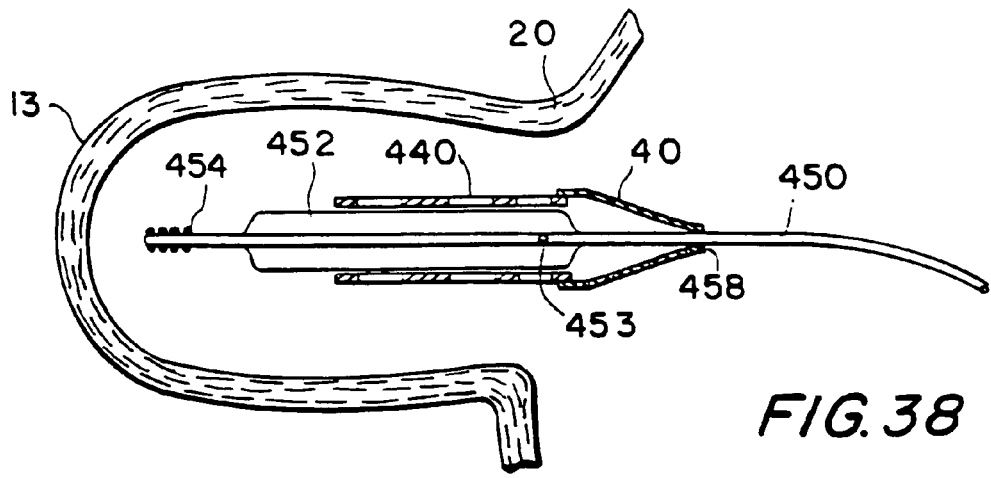
FIG. 38 is a partial cross-sectional view illustrating an early stage in the procedure of installing of the filtering membrane of FIGS. 29-37 in accordance with the invention.
Figure 39:
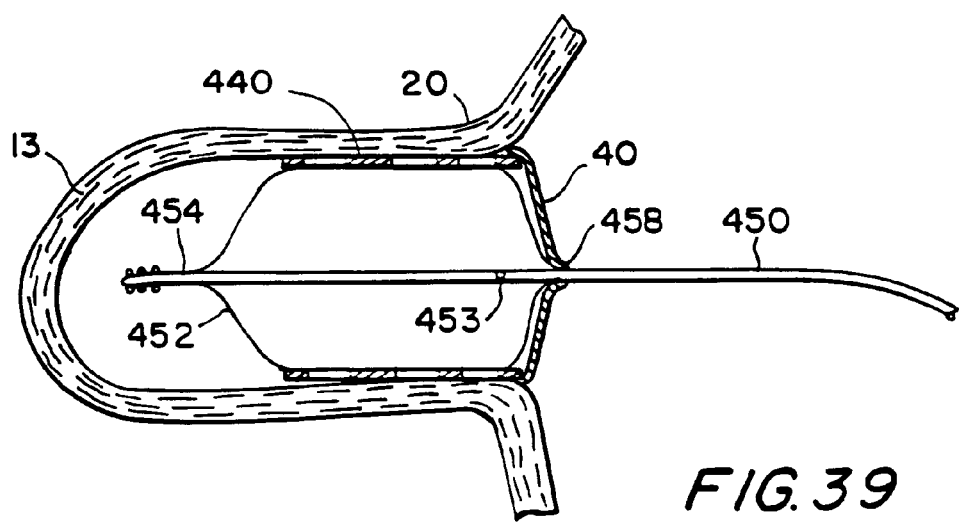
FIG. 39 is a partial cross-sectional view similar to FIG. 39 illustrating a later stage in the procedure in accordance with the invention.
Figure 40:
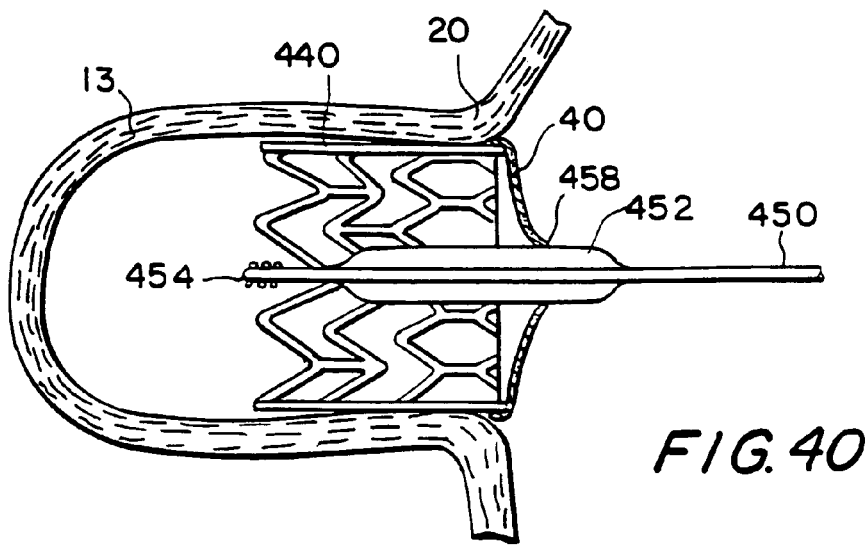
FIG. 40 is a partial cross-sectional view similar to FIG. 39 illustrating a still later stage in the procedure in accordance with the invention.

FIGS. 38-40 illustrate the procedure for installing attachment apparatus 440 and filtering membrane 40 in the atrial appendage 13. In an initial step (FIG. 38), balloon structure 452, along with attachment apparatus 440 are inserted into the atrial appendage 13 in its initial, compact configuration. In FIG. 39, expansion fluid is passed through catheter 450 and exits through port 453 to fill the interior of balloon structure 452. Balloon structure 452 expands, thereby radially enlarging attachment apparatus 440, as described with respect to FIGS. 31-33, above. As illustrated in FIG. 40, attachment apparatus engages the interior of the atrial appendage 13, thereby securing filtering membrane 40 in position across the ostium 20. Balloon structure 452 may be removed from the atrial appendage 13 by returning the balloon structure 452 to its initial compact configuration (e.g., by draining the expansion fluid therefrom) and withdrawing the balloon structure proximally through opening 458. As described above with respect to FIGS. 34-37, the filtering membrane may be fabricated with an elastic portion which expands to permit the withdrawal of the balloon structure therethrough, and which subsequently reduces in size to inhibit the passage of thrombi, clots and emboli therethrough into the atrium. The catheter structure 442 may be subsequently removed from the patient. Alternatively, the balloon structure 452 may remain within the atrial appendage 13 following expansion of attachment apparatus 440 and subsequent return of the balloon structure 452 to its initial compact configuration. For example, catheter 450 may be detachable from balloon structure 452 in a manner similar to the configuration of catheter 410 and tube 404 (FIG. 26).

Figure 41:
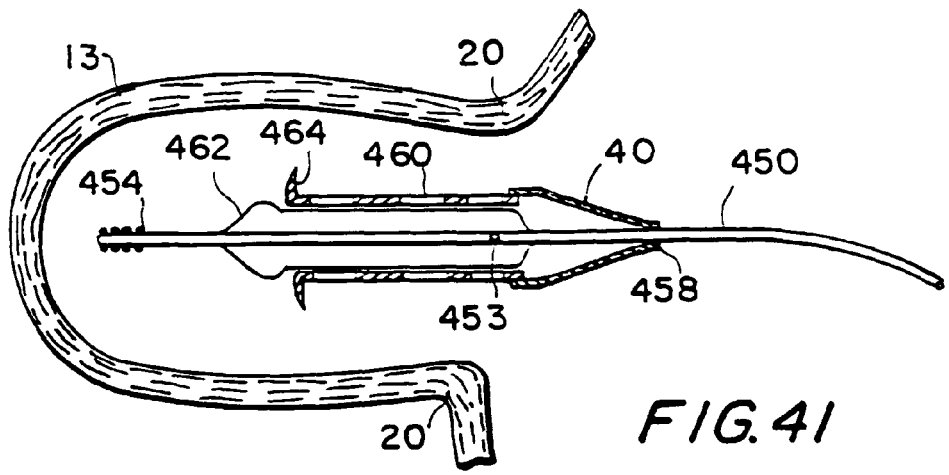
FIG. 41 is a view similar to FIG. 38 illustrating an alternative embodiment of the apparatus illustrated in FIGS. 29-32.
Figure 42:
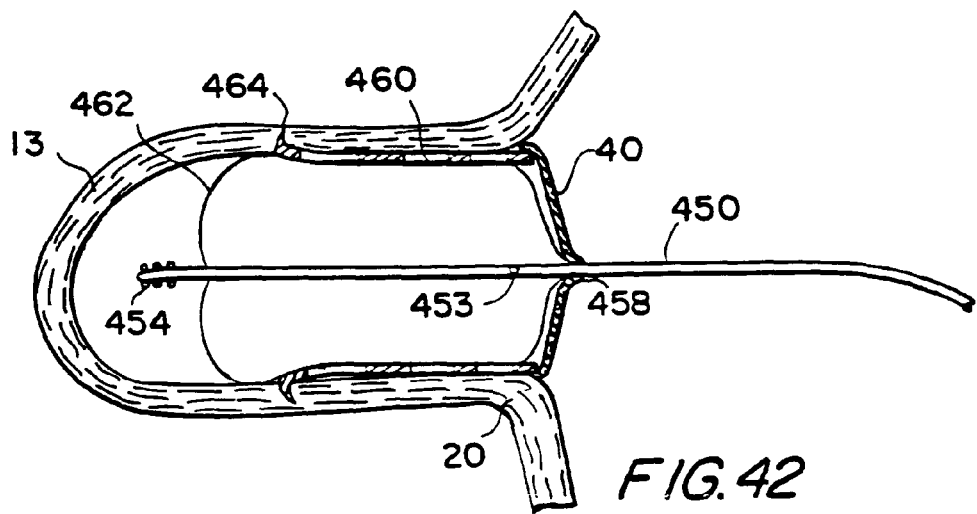
FIG. 42 is a partial cross-sectional view similar to FIG. 41 illustrating a later stage in the procedure in accordance with the invention.
Figure 43:
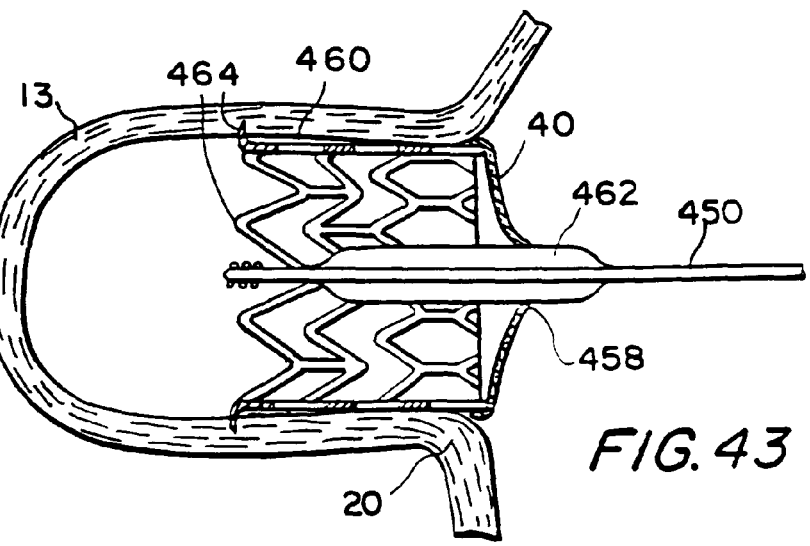
FIG. 43 is a partial cross-sectional view similar to FIG. 42 illustrating a still later stage in the procedure in accordance with the invention.

FIGS. 41-43 illustrate another embodiment of the invention. Attachment apparatus 460 and balloon apparatus 462 are substantially the same as attachment apparatus 440 and balloon apparatus 452, described hereinabove, with the differences noted below. Attachment apparatus 460 may be provided with a plurality of engagement members 464, such as prongs, hooks, or the like, in order to engage and/or pierce the wall of the atrial appendage to provide additional securement of the attachment apparatus 460. Balloon structure 452 may be used in connection with attachment apparatus 460. Alternatively, balloon structure 462 may be provided having a distal end portion which is configured to expand to a greater extent than the proximal portion thereof (FIG. 42). This greater expansion of the balloon structure 462 provides additional force in the area of the engagement members 464 to drive them into the wall of the atrial appendage 13 (FIG. 43).

Figure 44A:
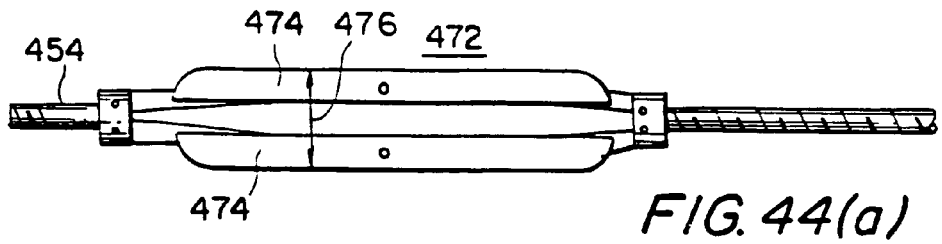
FIG. 44(a) illustrates an alternative embodiment of the apparatus illustrated in FIG. 30 in accordance with the invention.
Figure 44B:
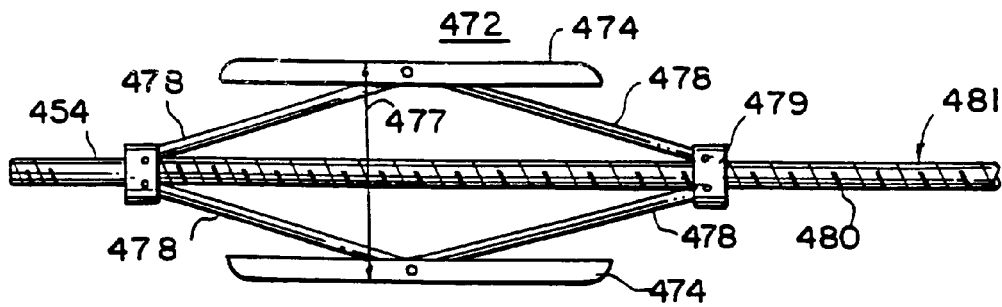
FIG. 44(b) illustrates the apparatus illustrated in FIG. 44(a) in an expanded configuration in accordance with the invention.
Figure 45:
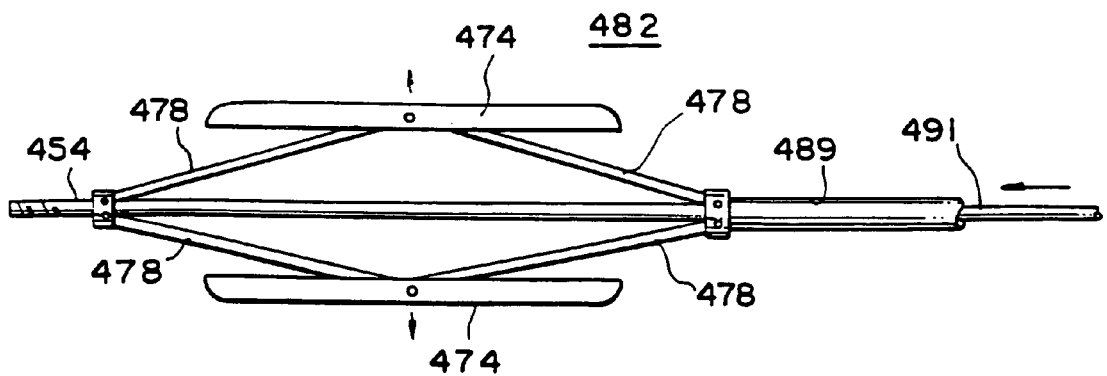
FIG. 45 is a view similar to FIG. 44 illustrating another embodiment in accordance with the invention

FIGS. 44-45 illustrate additional embodiments of expandable structures for radially enlarging the attachment apparatus 440 (or 460) within the atrial appendage. Instead of, or in addition to balloon structures (such as balloon structure 452), it is also contemplated that mechanical expansion structures may be particularly useful. FIGS. 44(a)-(b) illustrate a mechanical expansion structure 472 which may be used to radially expand attachment apparatus 440. As shown in FIG. 44(a), mechanical expansion structure 472 may have a compact configuration wherein a plurality of contact members 474 define a diameter 476 that enables the structure to be inserted within the attachment apparatus 440. As illustrated in FIG. 44(b), mechanical expansion structure 472 also has an expanded configuration, wherein contact members 474 are further spaced apart to define a larger diameter 477 which radially enlarges the attachment apparatus to the configuration illustrated in FIGS. 32-33 and 39-40. A linkage configuration may include linkage members 478 and sleeve 479. Sleeve 479 is provided with internal threading (not shown) which engages external threading 480 on a portion of drive screw 481. Angular rotation of drive screw 481 (as indicated by the arrow) provides longitudinal movement of sleeve 479 which cooperates with linkage members 478 to controllably move the contact members 474 between the compact and expanded configurations.

FIG. 45 illustrates mechanical expansion structure 482, which is substantially identical to mechanical expansion structure 472. Sleeve 489 interacts with linkage members 478 to controllably move contact members 474, as described above with respect to sleeve 479. Sleeve 489 is longitudinally slidable with respect to elongated member 491. A locking structure (not shown) may also be provided to fix the position of sleeve 489 (and thus contact members 474) with respect to elongated member 491.

Mechanical expansion structures 472 and 482 may remain in the atrial appendage 13 following the expansion of attachment apparatus 440 (or 460). A portion of the drive screw 481 or elongated member 491 may be detachable from the expansion structures 472 or 482, respectively (not shown). Alternatively, apparatus substantially similar to mechanical expansion structures 472/482 may be useful as supporting structures for filtering membrane 40. According to this embodiment, filtering membrane 40 may be attached to an end portion of structure 472/482, e.g., by attaching filtering membrane 40 to end portions of contact members 474 or by substantially enclosing contact members 474 and linkage members 478. The structure 472/482 may be positioned in the atrial appendage 13 and expanded as described above, such that filtering membrane 40 extends across the ostium 20 to allow blood to pass therethrough while inhibiting the passage of thrombus through the filtering membrane 40. Drive screw 481 or elongated member 491 may be subsequently detached from the apparatus 472/482.

Figure 46:
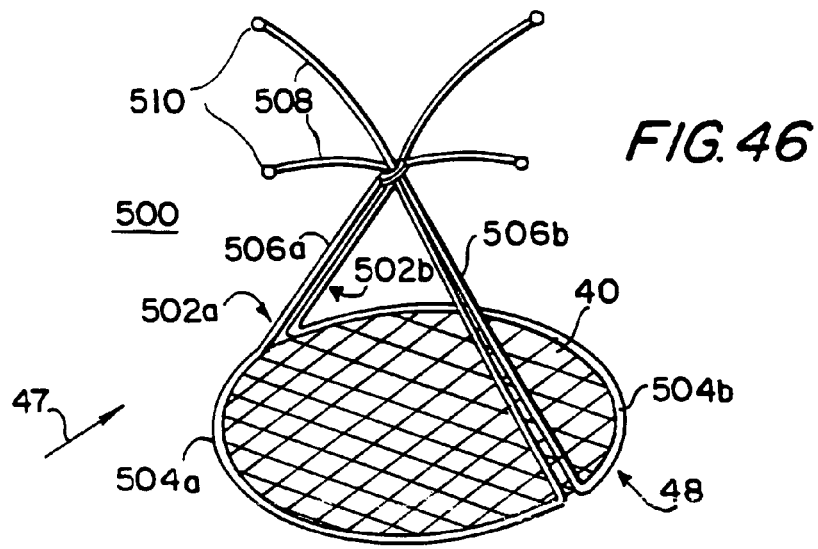
FIG. 46 illustrates yet another embodiment of the filtering membrane and apparatus for attaching the filtering membrane in accordance with the invention.
Figure 47:
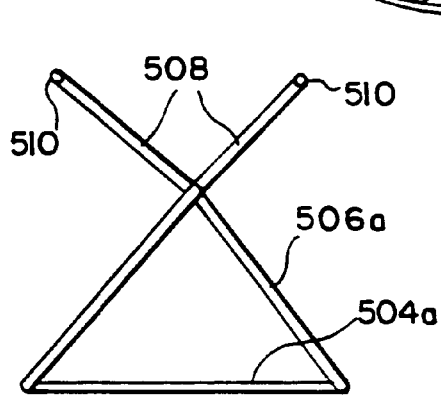
FIG. 47 is an elevational view taken from direction 47 of FIG. 41 in accordance with the invention.
Figure 48:
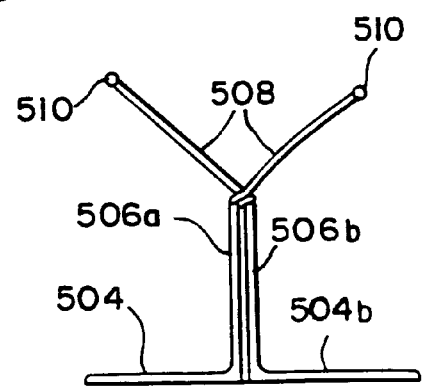
FIG. 48 is elevational view taken from direction 48 of FIG. 41 in accordance with the invention.

FIGS. 46-48 illustrate another embodiment of the invention. Filtering membrane 40 may be installed in the atrial appendage 13 and held therein by attachment apparatus 500, which preferably consists of a pair of flexible wire portions 502a and 502b, which are preferably constructed of a material such as nitinol or Elgiloy or stainless steel and having a wire diameter of approximately 0.005 to 0.020 inch. Each wire portion 502a/502b may include a curved portion 504a/504b, a pair of support members 506a/506b and a plurality of engagement members 508. The curved portions 504a/504b define a substantially closed portion for mounting the filtering membrane 40. The filtering membrane 40 is attached with sutures, adhesive, or other appropriate means. The engagement members 508 are configured to engage the interior of the atrial appendage 13 to secure the filtering membrane 40 in position across the ostium 20, as will be described herein. The engagement members 508 may be provided with atraumatic end portions 510.

Figure 49:
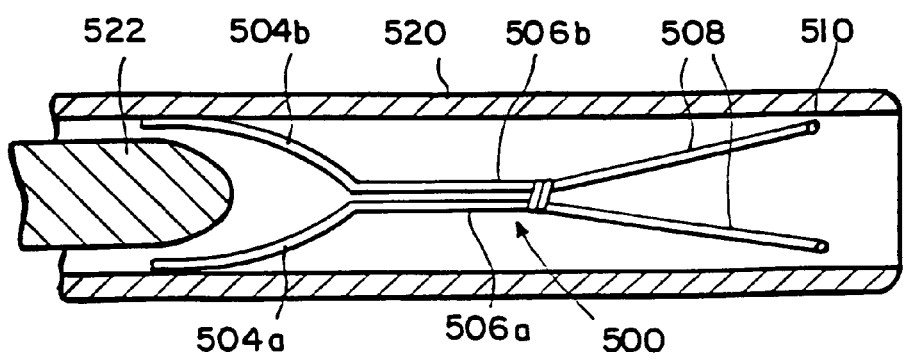
FIG. 49 is a sectional view illustrating the apparatus of FIG. 46 along with additional apparatus in accordance with the invention.

FIG. 49 illustrates attachment apparatus 500 and filtering membrane 40 in a compacted configuration for installation in the atrial appendage 13. Preferably, a delivery catheter apparatus 520 is used to introduce the attachment apparatus 500 and filtering membrane 40 to the atrial appendage. The curved portions 504a/504b are deflected proximally toward parallelism with the longitudinal axis of the catheter 520, and the engagement members 508 are deflected distally toward parallelism with the longitudinal axis. An inner member 522 is slidably received within the interior of catheter 520 and may be moved relatively longitudinally with respect to catheter apparatus 520 in order to deploy and install the attachment apparatus 500 and filtering membrane 40.

Figure 50:
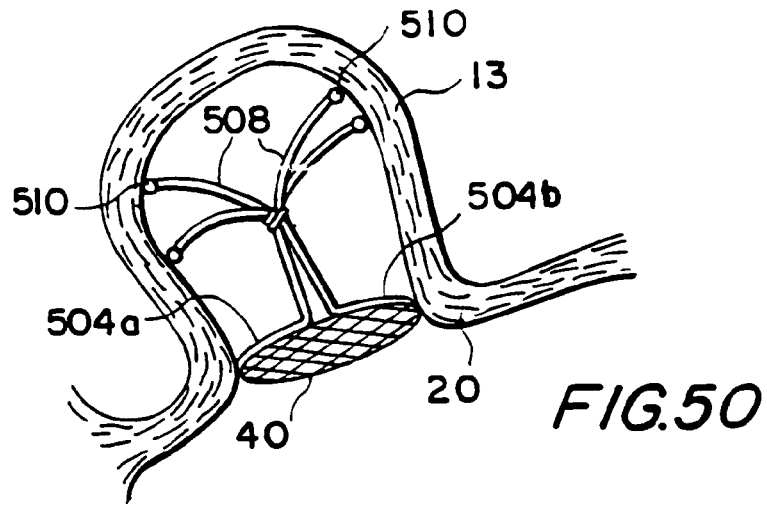
FIG. 50 is a partial cross-sectional view illustrating a first installed configuration of the apparatus of FIG. 46 in accordance with the invention.
Figure 51:
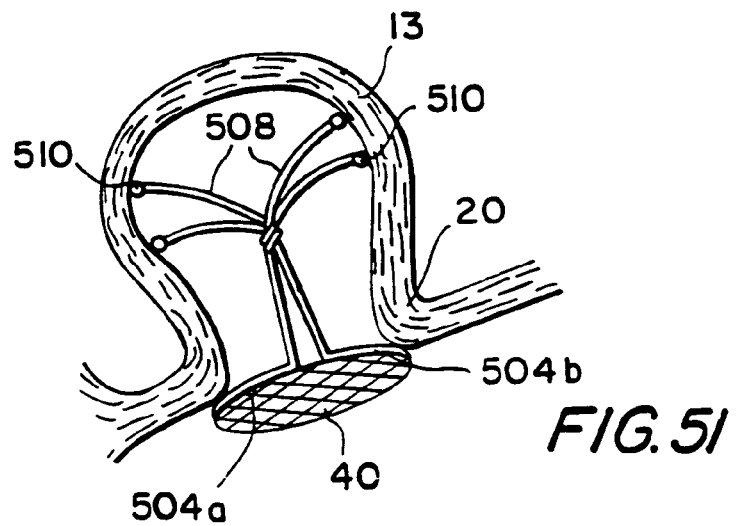
FIG. 51 is a partial cross-sectional view similar to FIG. 50 illustrating a second installed configuration of the apparatus of FIG. 46 in accordance with the invention.
Figure 52:
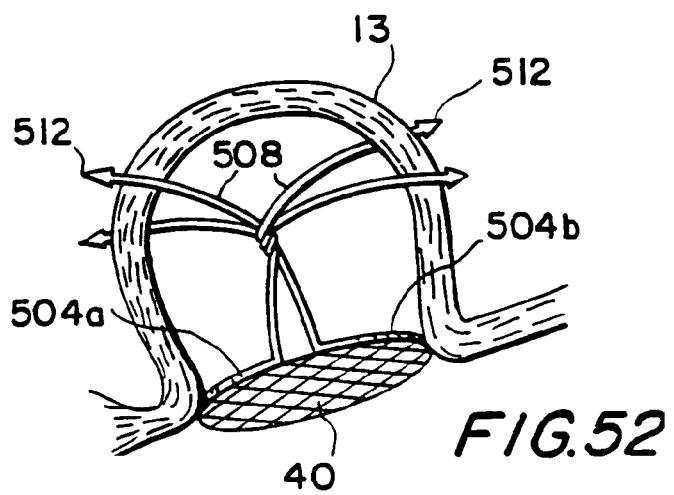
FIG. 52 is a partial cross-sectional view illustrating another embodiment of the apparatus in accordance with the invention.

FIGS. 50-52 illustrated several options for installing the filtering membrane across the ostium 20. As illustrated in FIG. 50, the curved portions 504a/504b are positioned within the walls of the ostium 20 itself. The engagement members 508 provide additional support by engaging the interior of the atrial appendage. Alternatively, the curved portions 504a/504b are positioned outside the ostium within the atrium. Engagement members 508 retain the filtering membrane 40 in position. According to yet another alternative embodiment, engagement member 508 are provided with sharpened barb end portions 512 which engage and/or pierce the wall of the atrial appendage to secure the filtering membrane in position (FIG. 52).

Figure 53:
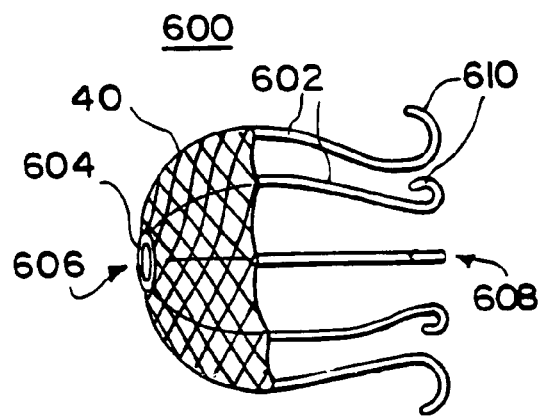
FIG. 53 illustrates yet another embodiment of the apparatus in accordance with the invention.
Figure 54:
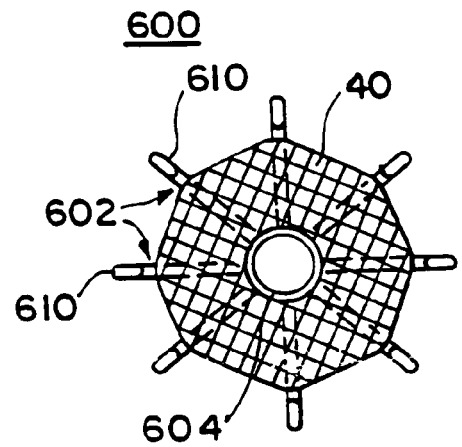
FIG. 54 is an end view of the apparatus of FIG. 53 in accordance with the invention.

FIGS. 53-54 illustrate another embodiment of the invention. Attachment apparatus 600 provides a plurality of strut wires 620, e.g., six to 12 strut wires, that extend radially outward from a support ring 604. The strut wires 602 may be constructed from an alloy, such as nitinol, having shape memory characteristics. The support ring 604 maintains the strut wires 602 in the proper configuration and may be made of radiopaque materials, such as, e.g., platinum to provide fluoroscopic imaging of the device position. The support ring 604 is adjacent the proximal end portion 606 of the apparatus 600, and the strut wires 602 extend distally therefrom toward the distal end portion 608. The strut wires may be provided with barbs 610 or other methods for attachment to the interior of the atrial appendage. The proximal portion of the struts 602 provide a bulb shape to conform to the ostium and/or the internal wall of the atrial appendage.

The filtering membrane 40 is attached to strut wires 602 adjacent the proximal portion 606 and provides the characteristics described above, wherein blood is allowed to pass through the filtering membrane 40, but thrombi, clots, and emboli are inhibited from passing therethrough. The filtering membrane 40 may be connected to the strut wires 602 using adhesive, sutures, encapsulation or other means.

Figure 55:
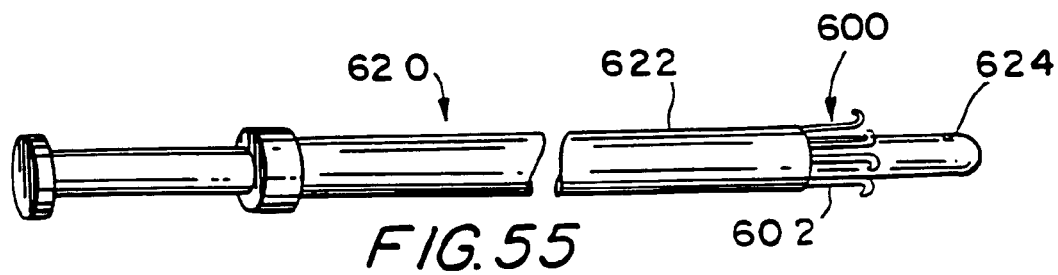
FIG. 55 illustrates additional apparatus for installing the apparatus of FIG. 53 in accordance with the invention.
Figure 56:
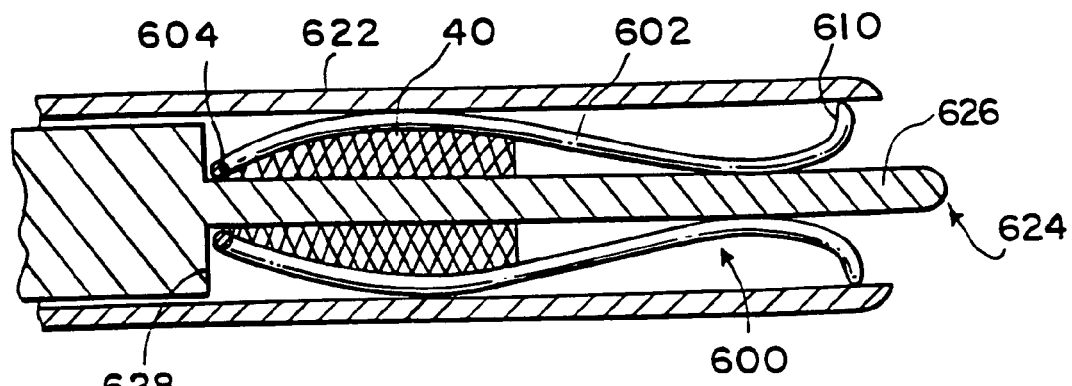
FIG. 56 is an enlarged sectional view of the apparatus of FIG. 53 and FIG. 55 in a compacted configuration, in accordance with the invention.

FIGS. 55-56 illustrate apparatus for delivering and installing the attachment apparatus 600 and filtering membrane 40. The catheter apparatus 620 includes an outer sheath 622 and an inner member 624 slidably received within the interior of outer sheath 622. The outer sheath 622 and inner member 624 may be fabricated from materials, such as polymers, that are sufficiently flexible to negotiate the anatomy, yet sufficiently rigid for relative longitudinal movement to deploy and position the attachment apparatus 600. Inner member 624 may have a distal end portion 626 and a shoulder portion 638. Support ring 604 is sized to provide a slide fit over the distal portion 626, and is engaged by the shoulder portion 608. The aperture in support ring 604 is sufficiently small to inhibit clots from passing through. (Alternatively, the aperture in support ring is provided with an elastic material such as elastic section 476b illustrated in FIG. 35 to prevent the passage of clots therethrough.) When positioned about distal end portion 626, strut wires 602 are deflected distally toward parallelism with the longitudinal axis of the catheter device 622 and retained in the deflected configuration by the outer sheath 622. In order to deploy the attachment apparatus 600, the outer sheath 622 is moved longitudinally relative to the inner member 626. The shoulder portion 628 retains the attachment apparatus 600 in position. Upon retraction of the outer sheath 622, the shape memory characteristics of the strut wires 602 causes the apparatus to return to a shape approximating that of FIG. 53.

Figure 57:
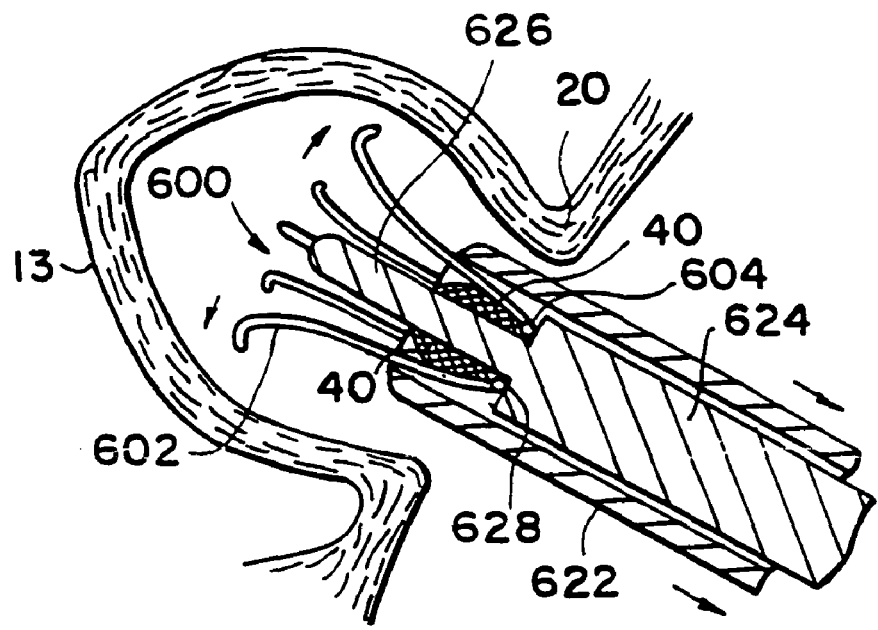
FIG. 57 is a partial cross-sectional view of the apparatus of FIG. 56 illustrating an early stage in the procedure in accordance with the invention.
Figure 58:
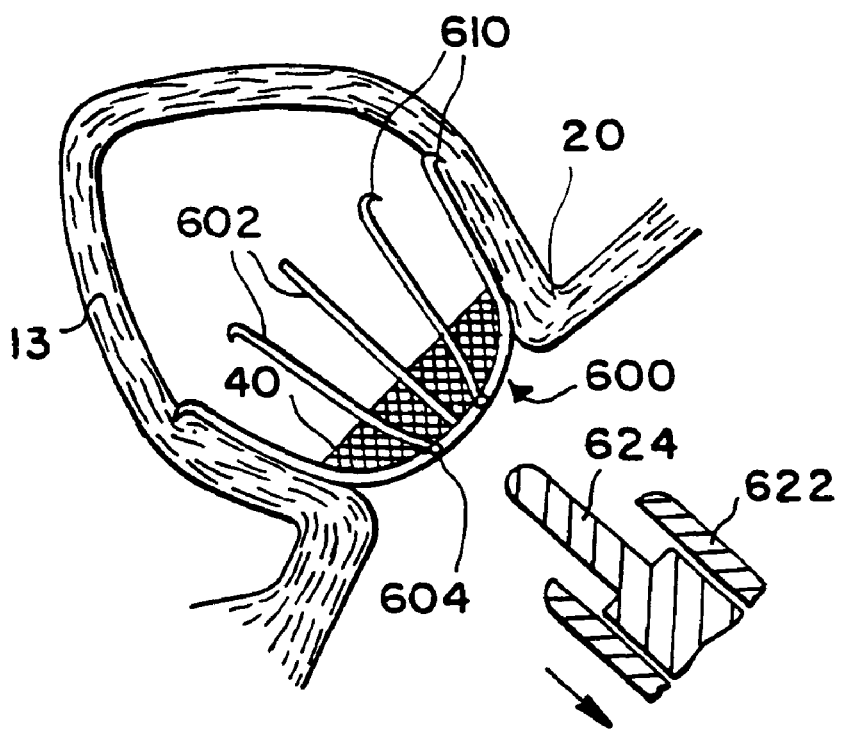
FIG. 58 is a partial cross-sectional view similar to FIG. 57 illustrating a later stage in the procedure in accordance with the invention.

FIGS. 57-58 illustrate the installation of attachment apparatus 600 and filtering membrane 40 in greater detail. As illustrated in FIG. 57, the catheter device 620 is advanced partially within the atrial appendage 13. The outer sheath 622 may be retracted proximally, which permits the strut wires 602 to extend radially outwardly. The physician may use the radiopaque characteristics of the ring 604 in order to properly position the ring 604 within the ostium 20. Further proximal retraction of the outer sheath 622 allows the strut wires 602 to extend further radially outward to engage the interior of the atrial appendage 13 (FIG. 58). The barbs 610 may engage and/or pierce the wall of the atrial appendage to provide increased stability of the attachment apparatus 600. The filtering membrane 40 is consequently positioned across the ostium 20 in order to allow blood to pass through the filtering membrane, while substantially inhibiting thrombi, clots, and emboli from exiting the atrial appendage 13.

FIGS. 59-60 illustrate another embodiment of the invention. Attachment apparatus 650 provides a first plurality of strut wires 652 that extend distally and radially outward from a support ring 654 toward the distal end portion 656 of the attachment apparatus 650, and a second plurality of strut wires 658 that extend proximally and radially outward from support ring 654 toward the proximal end portion 660. The strut wires 652/658 may be constructed from an alloy, similar to material used for strut wires 602, above. The support ring 654 maintains the strut wires 652/658 in the proper configuration and is substantially similar to support ring 604, above. The strut wires 652 may be provided with barbs 662 or other methods for attachment to the interior of the atrial appendage. The struts 652/658 are configured to engage the walls of the ostium on the inner and outside sides thereof, respectively.

The strut wires 658 may serve as a membrane mounting structure. The filtering membrane 40 is attached to strut wires 658 and provides the characteristics described above, wherein blood is allowed to pass through the filtering membrane 40, but thrombi, clots, and emboli are inhibited from passing therethrough. The filtering membrane 40 may be connected to the strut wires 602 using adhesive, sutures, encapsulation or other means.

Another embodiment of the invention is illustrated in FIG. 61. Attachment apparatus 670 is constructed of braided or woven mesh material rather than the strut wires 652/658 described with respect to FIGS. 59-60. The distal portion 672 is configured to engage the wall of the atrial appendage adjacent the inner portion of the ostium, and the proximal portion 676 is configured to engage the outer portion of the ostium, and the neck portion 674 is disposed therebetween. The braided or woven self-expanded mesh material of attachment apparatus 670 has similar filtering characteristics as filtering membrane 40, or alternatively, a filtering membrane is attached to the mesh material to provide those characteristics.

FIGS. 62-63 illustrate apparatus for delivering and installing the attachment apparatus 650 and filtering membrane 40 and/or attachment apparatus 670. The catheter apparatus 620 is described above with respect to FIG. 55. Strut wires 652 of apparatus 650 (or distal portions 672 of apparatus 670) are deflected distally toward parallelism with the longitudinal axis of the catheter device 620 and retained in the deflected configuration by the outer sheath 622. Similarly, strut wires 658 (or proximal portions 676) are deflected proximally toward parallelism with the longitudinal axis and retained in this configuration by the outer sheath 622. In order to deploy the attachment apparatus 600, the outer sheath 622 is moved longitudinally relative to the inner member 626. The shoulder portion 628 retains the attachment apparatus 650/670 in position. Upon retraction of the outer sheath 622, the shape memory characteristics of the strut wires 652/658 (or portions 672/676) cause the apparatus to return to a shape approximating that of FIG. 59 (or FIG. 61).

Figure 64:
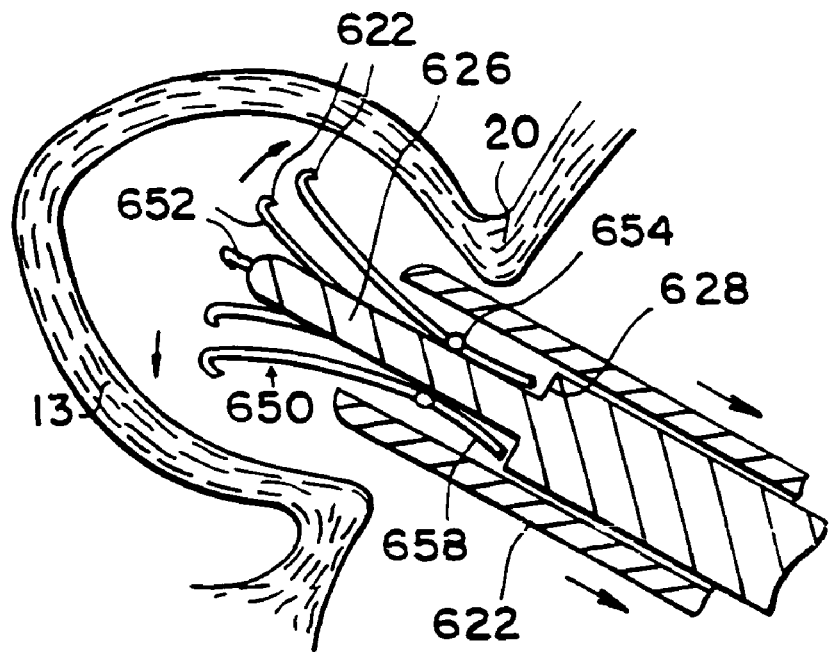
FIG. 64 is a partial cross-sectional view of the apparatus of FIG. 63 illustrating an early stage in the procedure in accordance with the invention.
Figure 65:
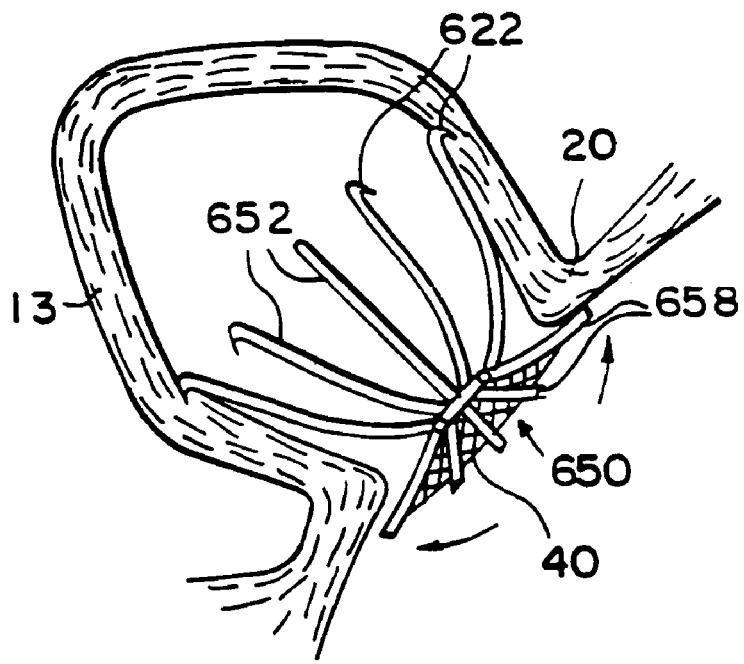
FIG. 65 is a partial cross-sectional view similar to FIG. 64 illustrating a later stage in the procedure in accordance with the invention.

FIGS. 64-65 illustrate the installation of attachment apparatus 650/670 and filtering membrane 40 in greater detail. As illustrated in FIG. 64, the catheter device 622 is advanced partially within the atrial appendage 13. The outer sheath 622 may be retracted proximally, which permits the strut wires 652 to extend radially outwardly. The physician may use the radiopaque characteristics of the ring 654 in order to properly position the ring 654 within the ostium 20. Further proximal retraction of the outer sheath 622 allows the distal strut wires 652 and the proximal strut wires 658 to extend radially outward and engage the interior of the atrial appendage 13 (FIG. 65). The barbs 662 may engage and/or pierce the wall of the atrial appendage to provide increased stability of the attachment apparatus 600. The filtering membrane 40 is consequently positioned across the ostium 20 in order to allow blood to pass through the filtering membrane, while substantially inhibiting thrombi, clots, and emboli from exiting the atrial appendage 13.

FIGS. 66-67 illustrate yet another embodiment of the invention. Attachment apparatus 700 provides a plurality of strut wires 702 that extend radially outward from a support ring 704. A first portion 706 of each strut wire 702 extends towards the proximal end portion 708 of the attachment apparatus 700, and a second portion 710 of each strut wire 702 extends towards the distal end portion 712. The distal portion 710 of each strut wire 702 may be provided with a sharpened barb tip 714 or other methods for attachment to the interior of the atrial appendage. The strut wires 702 are constructed from an alloy, similar to material used for strut wires 602, above. The support ring 704 maintains the strut wires 702 in the proper configuration and is substantially similar to support ring 604, above. The proximal portions 706 and distal portions 710 of strut wires 702 are configured to engage the walls of the ostium on the outer and inner sides thereof, respectively.

The filtering membrane 40 is attached to proximal portions 706 of strut wires 702 and provides the characteristic described above, wherein blood is allowed to pass through the filtering membrane 40, but thrombi, clots, and emboli are inhibited from passing therethrough. The filtering membrane 40 may be connected to the strut wires 702 using adhesive, sutures, encapsulation or other means.

FIGS. 68-69 illustrate apparatus for delivering and installing the attachment apparatus 700 and filtering membrane 40. The catheter apparatus 620 is described above with respect to FIG. 55. Strut wires 702 are deflected towards parallelism with the longitudinal axis of the catheter device 620 and retained in the deflected configuration by the outer sheath 622. In order to deploy the attachment apparatus 700, the outer sheath 622 is moved longitudinally relative to the inner member 626. The shoulder portion 628 retains the attachment apparatus 700 in position. Upon retraction of the outer sheath 622, the shape memory characteristics of the strut wires 702 causes the apparatus to resume the shape approximating that of FIG. 66.

Figure 70:
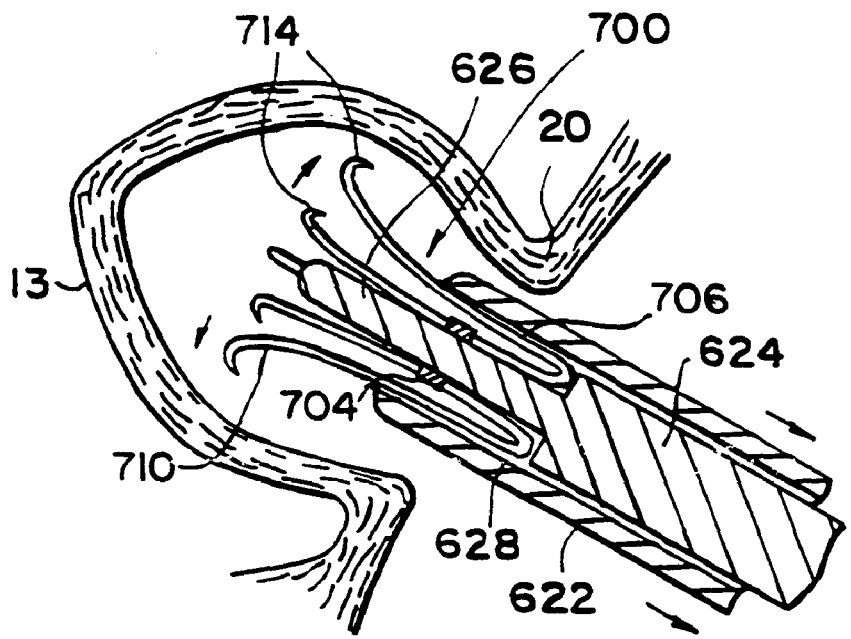
FIG. 70 is a partial cross-sectional view of the apparatus of FIG. 66 illustrating an early stage in the procedure in accordance with the invention.
Figure 71:
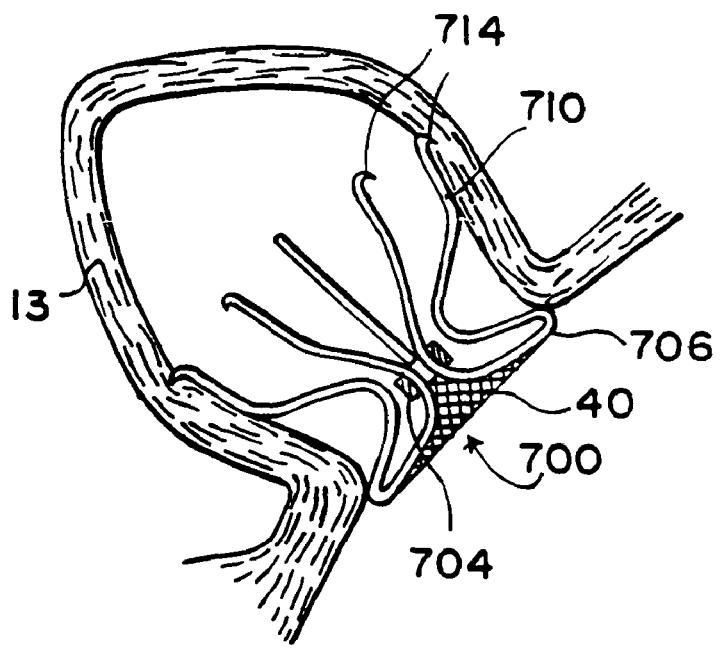
FIG. 71 is a partial cross-sectional view similar to FIG. 70 illustrating a later stage in the procedure in accordance with the invention.

FIGS. 70-71 illustrate the installation of attachment apparatus 700 and filtering membrane 40 in greater detail. As illustrated in FIG. 70, the catheter device 622 is advanced partially within the atrial appendage 13. The outer sheath 622 may be retracted proximally, which permits the distal portions 710 of strut wires 702 to extend radially outwardly. Further proximal retraction of the outer sheath 622 allows the distal portions 710 to engage the interior of the atrial appendage 13 and the proximal portions 706 to engage the outer portion of the ostium 20 (FIG. 71). The barbs 714 may engage and/or pierce the wall of the atrial appendage to provide increased stability of the attachment apparatus 700. The filtering membrane 40 is consequently positioned across the ostium 20 in order to allow blood to pass through the filtering membrane, while substantially inhibiting thrombi, clots, and emboli from exiting the atrial appendage 13.

Figure 72:
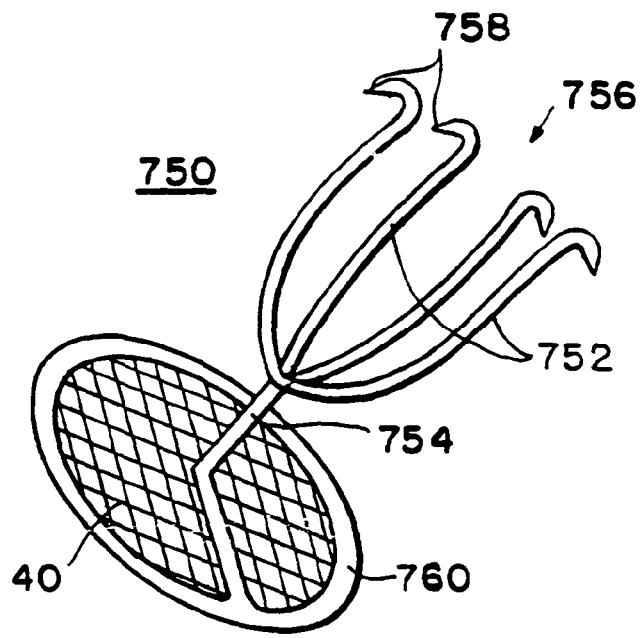
FIG. 72 illustrates another embodiment of the apparatus in accordance with the invention.
Figure 73:
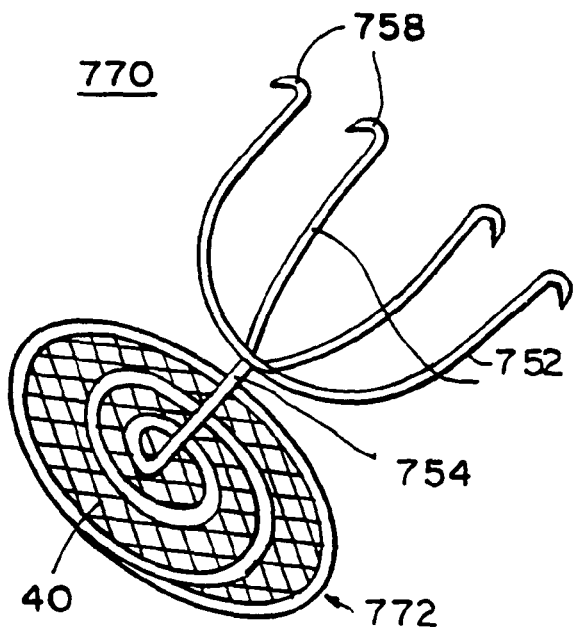
FIG. 73 illustrates yet another embodiment of the apparatus in accordance with the invention.

FIGS. 72-73 illustrate additional embodiments of the invention. Attachment apparatus 750 includes a plurality of strut wires 752 that extend radially outward and distally from a support member 754 towards the distal end portion 756. Each strut wire 752 may be provided with a sharpened barb tip 758 or other methods for attachment to the interior of the atrial appendage. The strut wires 702 are constructed from an alloy, similar to the material used for strut wires 602, above. The support member 754 maintains the strut wires 752 in the desired configuration.

The proximal end portion of support member 754 supports a curved membrane mounting structure 760 that defines a substantially closed curve. The filtering membrane 40 is attached to membrane mounting structure 760 and provides the characteristic described above, wherein blood is allowed to pass through the filtering membrane 40, but thrombi, clots, and emboli are inhibited from passing therethrough. The filtering membrane 40 may be connected to the membrane mounting structure 760 using adhesive, sutures, encapsulation or other means.

The attachment apparatus 770, illustrated in FIG. 73 is substantially identical to attachment apparatus 750, with the differences noted herein. For example, the proximal end portion of support member 754 supports a membrane mounting structure 772 having a spiral configuration. The filtering membrane 40 is attached to spiral mounting structure 772 substantially as described above with respect to membrane mounting structure 760, above. The spiral configuration may, e.g., assist in reducing the mounting structure to a compacted configuration during installation.

Figure 74:
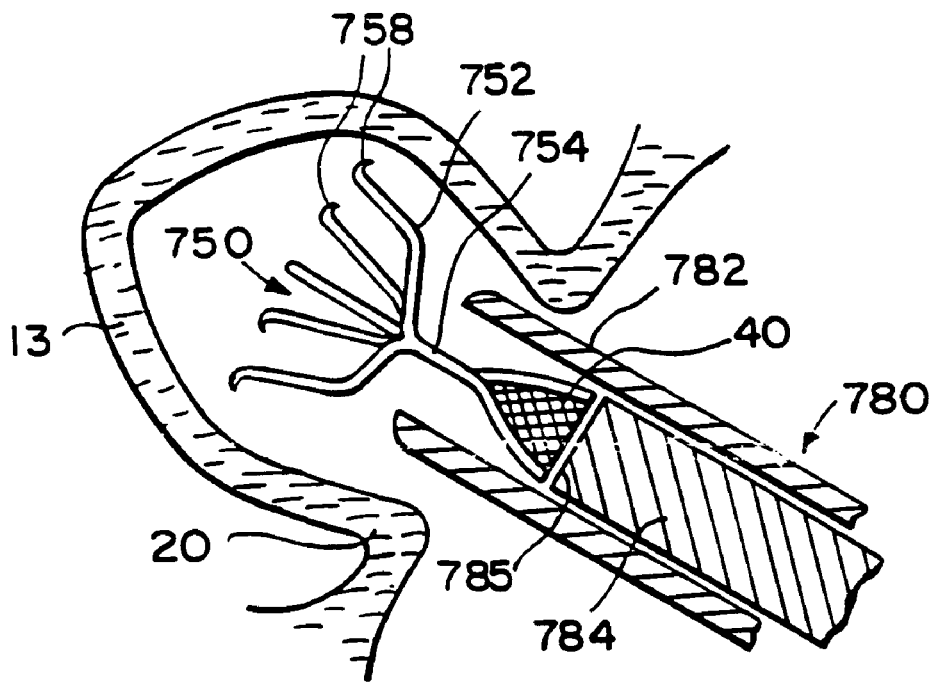
FIG. 74 is a partial cross-sectional view of the apparatus of FIG. 72 illustrating an early stage in the procedure in accordance with the invention.
Figure 75:
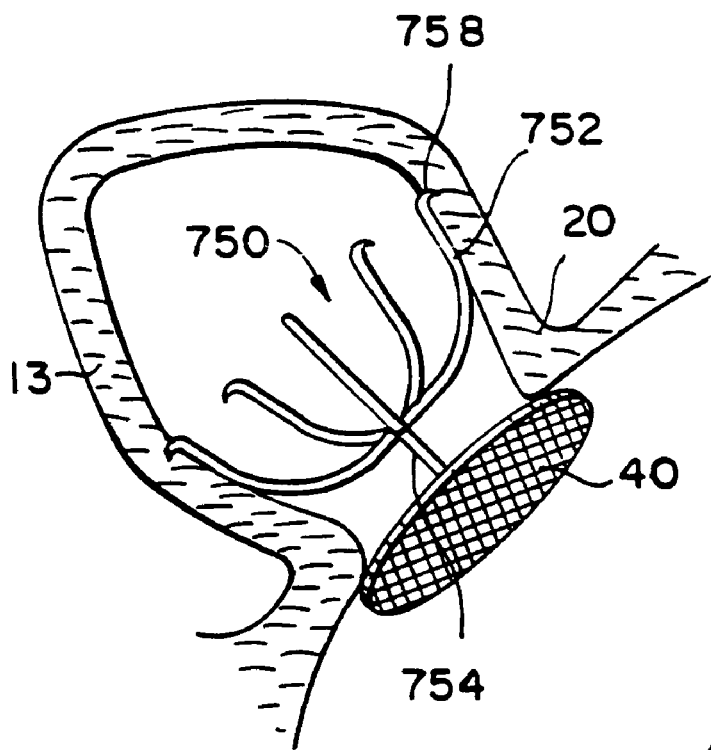
FIG. 75 is a partial cross-sectional view similar to FIG. 74 illustrating a later stage in the procedure in accordance with the invention.

FIGS. 74-75 illustrate the installation of attachment apparatus 750 (or 770) and filtering membrane 40 in the atrial appendage 13. Catheter apparatus 780 is provided for delivering and installing the attachment apparatus 750 and filtering membrane 40. The catheter apparatus 780 is similar to catheter apparatus 620 described above with respect to FIG. 55. Catheter apparatus 780 includes an outer sheath 782 and an inner member 784. Inner member 784 preferably has an engagement surface 785 on a distal end portion thereof. During installation, strut wires 752 are deflected towards parallelism with the longitudinal axis of the catheter device 780 and retained in the deflected configuration by the outer sheath 782 (not shown in FIG. 74). Similarly, the membrane mounting portion 760 (or 772) is folded, rolled or otherwise compacted inside outer sheath 782 as illustrated in FIG. 74.

In order to deploy the attachment apparatus 750, the catheter device 780 is advanced partially within the atrial appendage 13. The outer sheath 782 may be retracted proximally, which permits the strut wires 752 to extend radially outwardly due to its shape memory characteristics, as shown. The inner member 784 retains the attachment apparatus 750 in position.

As illustrated in FIG. 75, further proximal retraction of the outer sheath 782 allows the strut wires 752 to extend radially outward and engage the interior of the atrial appendage. The barbs 758 may engage and/or pierce the wall of the atrial appendage to provide increased stability of the attachment apparatus 700. The membrane mounting structure 760 (or 772) is likewise permitted to return to its disc-like configuration, such that filtering membrane 40 is positioned across the ostium 20 in order to allow blood to pass through the filtering membrane, while substantially inhibiting thrombi, clots, and emboli from exiting the atrial appendage 13.

Figure 77:
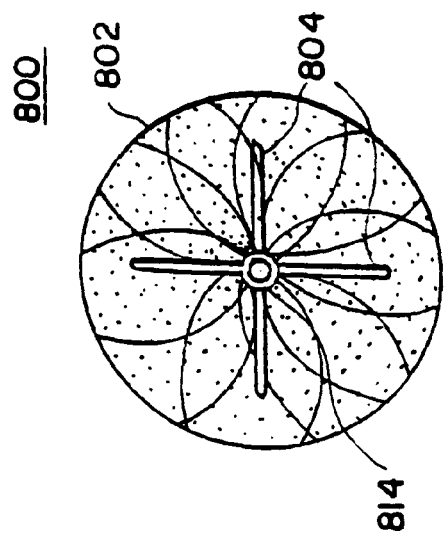
FIG. 77 is a distal end view of the apparatus of FIG. 76 in accordance with the invention.
Figure 76:
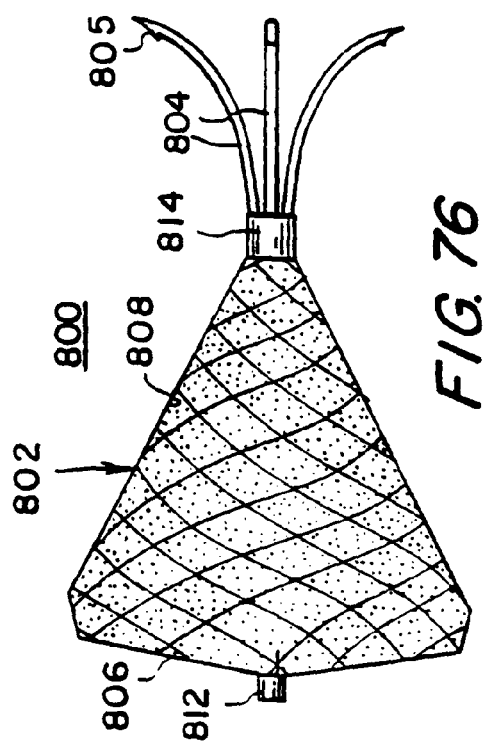
FIG. 76 illustrates yet another embodiment of the apparatus in accordance with the invention.

FIGS. 76-80 illustrate another embodiment of the invention. Attachment apparatus 800 has a braided or woven mesh portion 802 and a plurality of engagement members 804. Woven portion 802 defines a proximal portion 806 and distal portion 810. Woven portion 802 is fabricated from a material having shape memory characteristics, such as nitinol or an elastic polymeric material. Woven portion 802 is fabricated such that proximal portions 806 and distal portions 810 are normally biased to extend radially outward from support rings 812 and 814, respectively. The configuration of the woven portion 802 illustrated in FIGS. 76-77 is intended to conform to the ostium of the atrial appendage. The braided or woven self-expanding mesh material of woven portion 802 also has similar filtering characteristics as filtering membrane 40, which allows blood to pass therethrough while substantially inhibiting the passage of thrombus. Alternatively, a filtering membrane is attached to the woven material to provide these characteristics.

A plurality of engagement members 804 extend distally from support ring 814. The end portions of engagement members 804 may be provided with a barbed configuration to engage and/or pierce the wall of the atrial appendage and retain the engagement member in the wall. Engagement members 804 are similarly constructed from material having shape memory characteristics, such as nitinol.

Figure 78:
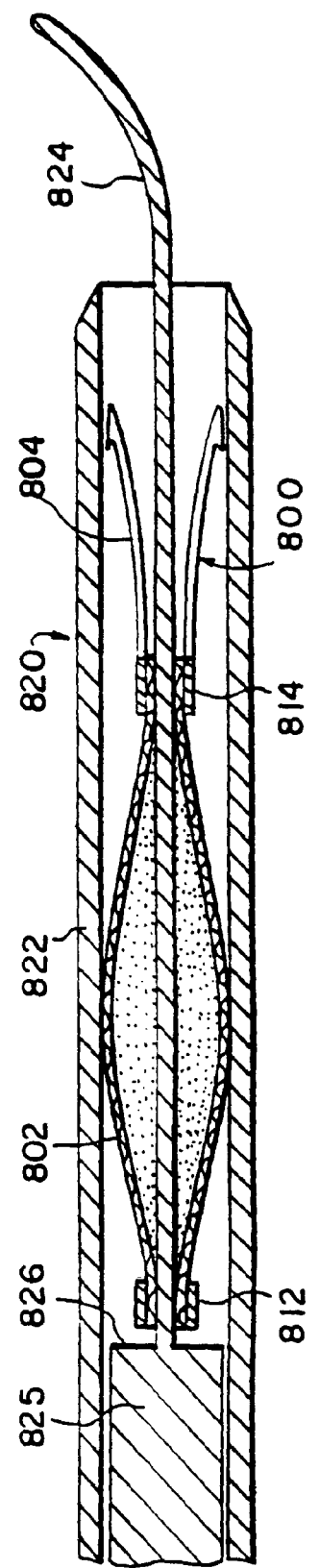
FIG. 78 is an enlarged sectional view of additional apparatus for use with the apparatus of FIGS. 76-77 in accordance with the invention.

FIG. 78 illustrates apparatus for delivering and installing the attachment apparatus 800 and filtering membrane 40. The catheter apparatus 820 is similar to that described above with respect to catheter apparatus 520 (FIG. 55). Inner member 825 may include a guide wire 824 and shoulder portion 826. Guide wire 824 may extend through support rings 812 and 814. When apparatus 800 is positioned on catheter apparatus 820, woven portion 802 is deflected towards parallelism with the longitudinal axis of the catheter device 820 and retained in the deflected configuration by the outer sheath 822. Similarly, the engagement members 804 are deflected towards parallelism and retained in such position by the outer sheath 822. In order to deploy the attachment apparatus 800, the outer sheath 822 is moved longitudinally relative to the inner member 626, while the shoulder portion 826 retains the attachment apparatus 800 in position. Upon retraction of the outer sheath 822, the shape memory characteristics of the woven portion 802 cause the apparatus to return to the shape approximating that of FIGS. 76-77.

Figure 79:
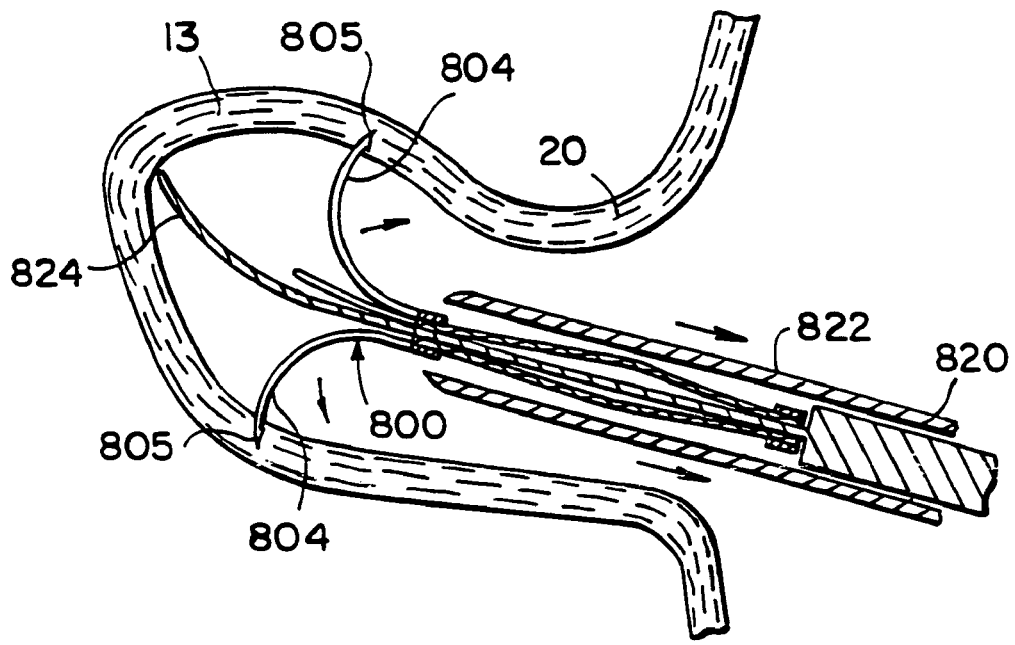
FIG. 79 is a partial cross-sectional view of the apparatus of FIGS. 76-77 illustrating an early stage in the procedure in accordance with the invention.
Figure 80:
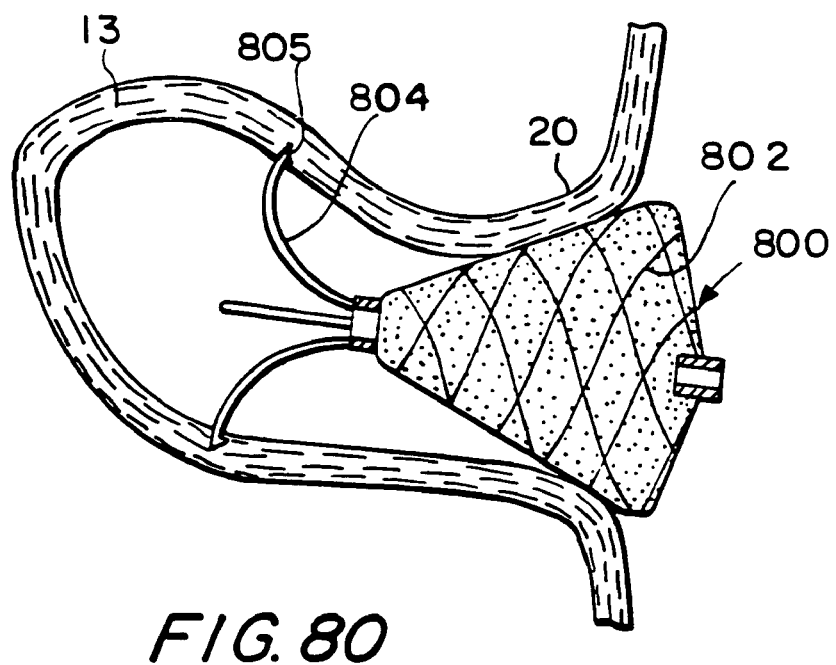
FIG. 80 is a partial cross-sectional view similar to FIG. 79 illustrating a later stage in the procedure in accordance with the invention.

As illustrated in FIG. 79, attachment apparatus 800 is partially inserted into the atrial appendage 13. Guide member 824 may be used to assist in the placement of attachment apparatus 800 with the atrial appendage by providing visual or tactile indication to the physician. Outer sheath 822 may be retracted proximally, which allows engagement members 804 to deflect radially outwardly, thereby engaging the interior wall of the atrial appendage. The barbs 805 may engage and/or pierce the wall of the atrial appendage to provide increased stability of the attachment apparatus 800. Outer sheath 822 may be further retracted proximally, thereby exposing woven portion 802, which expands radially outwardly to conform to the ostium 20 of the atrial appendage. The filtering membrane 40 (or the woven portion 802 having such filtering characteristics) is consequently positioned across the ostium 20 in order to allow blood to pass through the filtering membrane, while substantially inhibiting thrombi, clots, and emboli from exiting the atrial appendage 13.

FIGS. 81-86 illustrate another embodiment of the invention. Attachment apparatus 850 has a support structure including a plurality of struts 852 and an anchor structure 854. Struts 852 each define a proximal portion 856 and a distal portion 858. Struts 852 are fabricated from a material having shape memory characteristics, such as nitinol or an elastic polymeric material. Struts are fabricated such that proximal portions 856 and distal portions 858 are normally biased to extend radially outwardly. The configuration of the struts 852 illustrated in FIG. 78 conforms to the ostium of the atrial appendage when installed, as described herein. Filtering membrane 40 substantially covers struts 802, and provides the filtering characteristics described above, which allows blood to pass therethrough but substantially inhibits the passage of clots, thrombus, or emboli. Anchor structure 854 extends distally from struts 802 and includes a stylet tip 860 and two or more barbs 862.

FIG. 83 illustrates apparatus for delivering and installing the attachment apparatus 850 and filtering membrane 40. The catheter apparatus 880 is similar to that described above with respect to catheter apparatus 780 (FIG. 74). An outer sheath 882 and inner member 884 having an engagement surface 888 are provided. Struts 852 are deflected towards parallelism with the longitudinal axis of the catheter device 880 and retained in the deflected configuration by the outer sheath 882. Barbs 862 of the anchor portion are deflected towards parallelism by the distal nose portion 883 of the outer sheath 882. In order to deploy the attachment apparatus 850, the inner member 884 is moved longitudinally relative to the outer sheath 882. The engagement surface 888 of the inner member 884 urges the attachment apparatus 850 out of the outer sheath 882. Upon deployment from the outer sheath 882, the shape memory characteristics of the material causes the apparatus to return to the shape approximating that of FIG. 81.

Figure 84:
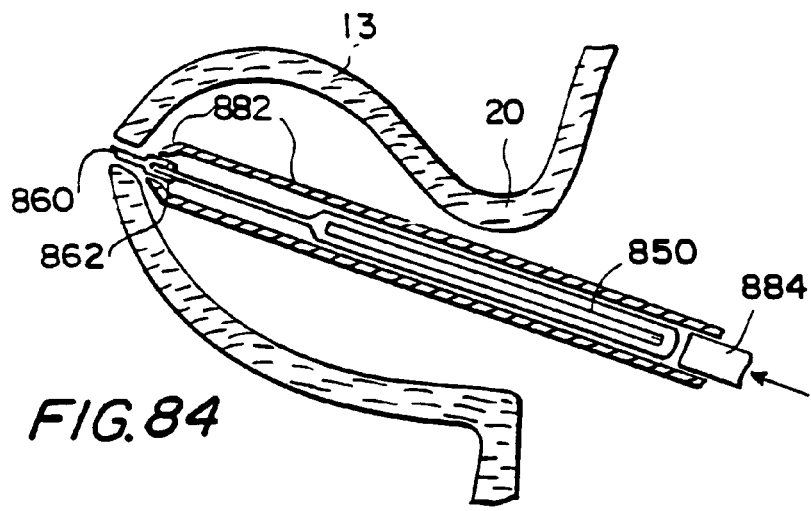
FIG. 84 is a partial cross-sectional view of the apparatus of FIGS. 81-82 illustrating an early stage in the procedure in accordance with the invention.
Figure 85:
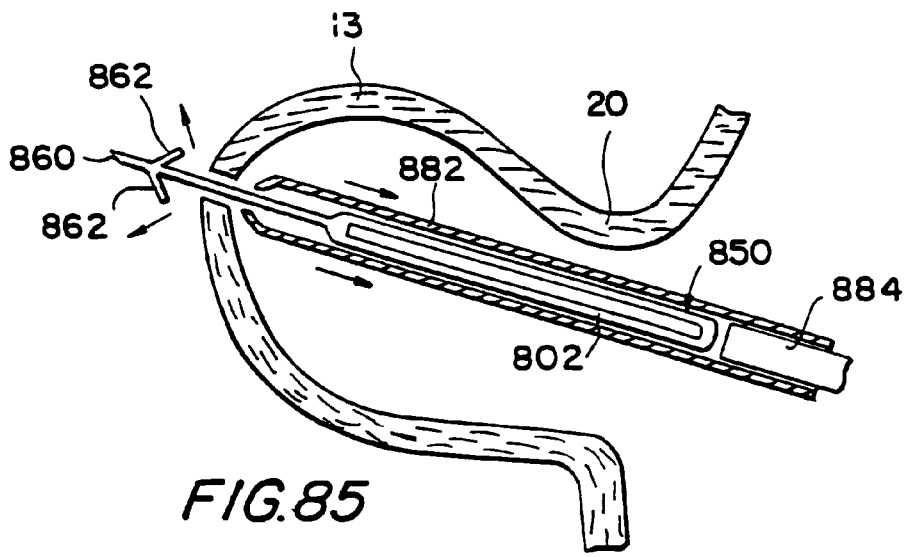
FIG. 85 is a partial cross-sectional view similar to FIG. 84 illustrating a later stage in the procedure in accordance with the invention.

As illustrated in FIG. 84, attachment apparatus 800 is partially inserted into the atrial appendage 13. The stylet tip 860 is exposed from outer sheath 882 and pierces the wall of the atrial appendage. The distal nose portion 883 of the outer sheath 882 retains the barbs 862 towards parallelism with the longitudinal axis, thereby enabling these barbs 862 to pass through the wall of the atrial appendage. Once the barbs 862 have passed through the wall, the barbs 862 may deflect radially outwardly, thereby preventing the anchor structure from being withdrawn proximally back through the wall (FIG. 85).

Figure 86:
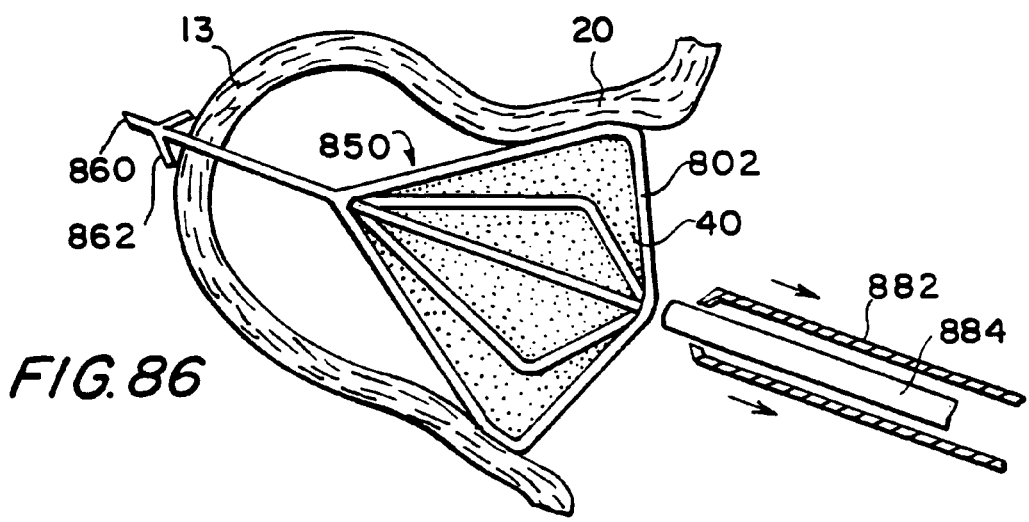
FIG. 86 is a partial cross-sectional view similar to FIG. 85 illustrating a still later stage in the procedure in accordance with the invention.

As illustrated in FIG. 86, outer sheath 882 may be retracted proximally, thereby exposing struts 852, which expand radially outwardly to conform to the ostium 20 of the atrial appendage. The filtering membrane 40 (or the woven portion 802 having such filtering characteristics) is consequently positioned across the ostium 20 in order to allow blood to pass through the filtering membrane, while substantially inhibiting thrombi, clots, and emboli from exiting the atrial appendage 13.

Figure 87:
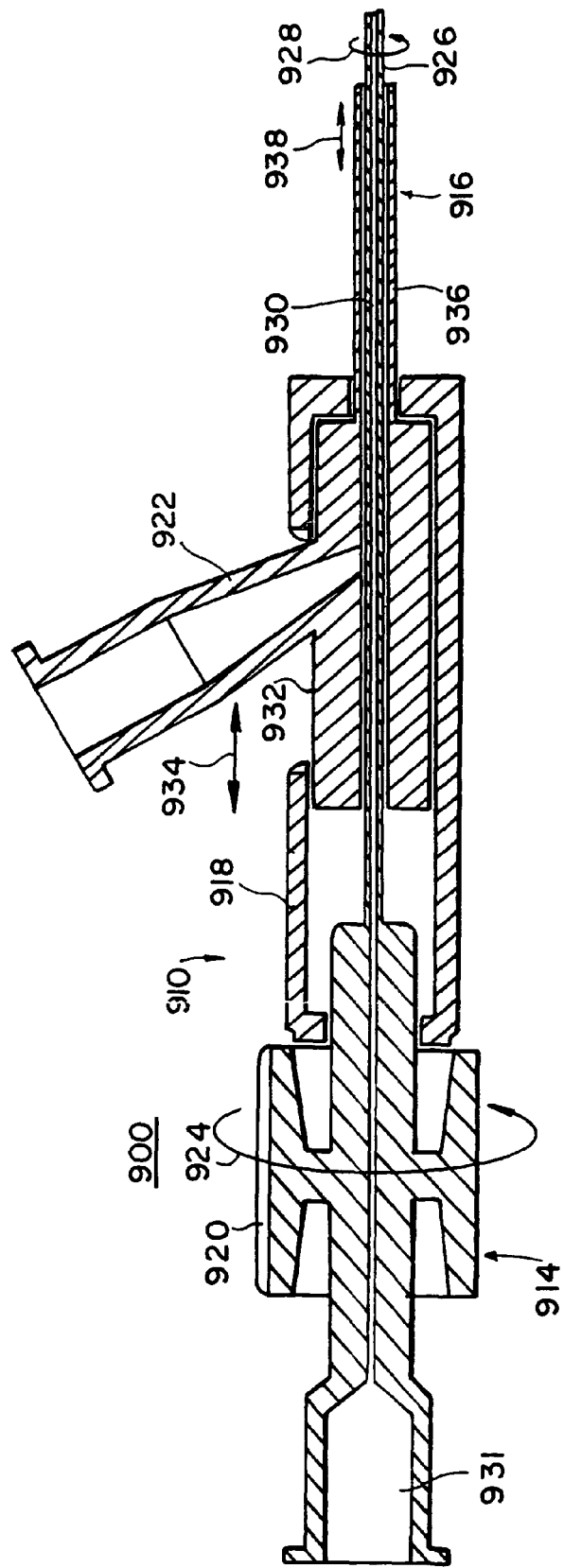
FIG. 87 is a sectional view of a proximal portion of another embodiment in accordance with the invention.

Another embodiment is illustrated in FIGS. 87 and 88 and is denoted generally by reference number 900. This embodiment may comprise a deployment apparatus 910 for installing attachment apparatus 912, thereby securing the filtering membrane 40 across the ostium 20 of the atrial appendage 13.

Deployment apparatus 910 has a proximal handle portion 914 and an elongated shaft portion 916. Elongated shaft portion 916 is preferably flexible for introducing the apparatus in the patient's vascular system and advancing the attachment apparatus into the atrium of the heart and adjacent the atrial appendage 13. Proximal handle portion 910 may comprise a body portion 918, which supports the elongated shaft portion 916 (consisting of a drive tube 926 and an outer tube 936). Body portion 918 also supports a rotation knob 920 and a longitudinal slide 922. The rotation knob 920 is configured to rotate angularly about the longitudinal axis of the body portion 918 (as indicated by arrow 924). Drive tube 926 is connected to rotation knob 920, such that rotation of the rotation knob 920 also rotates drive tube 926 about the longitudinal axis of (as indicated by arrow 928). Drive tube 926 may be provided with an internal lumen 930 to permit a guide wire (not shown) to be used in connection with this procedure.

Longitudinal slide control 922 may be slidable within a slot 932 in the body portion 918 (as indicated by arrow 934). Slide control 922 is connected to outer tube 936, and is longitudinally slidable therewith (as indicated by arrow 938).

As FIG. 88 illustrates, attachment apparatus 912 is configured for attachment to the distal end of elongated shaft portion 910. Attachment apparatus 912 is initially in the compacted configuration shown in FIGS. 88 and 89. As FIG. 89 illustrates, attachment apparatus 912 may comprise an outer portion 941 having an initially cylindrical configuration with a diameter 940 of about 2.0 mm and an initial length 942 of about 2.5 cm. Outer portion 941 is preferably manufactured from a flexible material such as stainless steel, nitinol, or Elgiloy®. Outer portion 941 has a plurality of longitudinal struts 946 defined elongated slots 944. Longitudinal struts 946 are configured to enlarge radially outwardly to engage the ostium of the left atrial appendage, as will be described herein.

Filtering membrane 40 is attached to outer portion 941 preferably about the proximal portions of the longitudinal struts 946 and has an initially cylindrical configuration. Filtering membrane 40 may be fabricated in a tapered configured and folded about the outer portion 941. Alternatively, membrane 40 may be fabricated from a material that has elastic characteristics which allow expansion from the initial cylindrical configuration to a substantially tapered configuration (see, FIG. 90).

Figure 90:
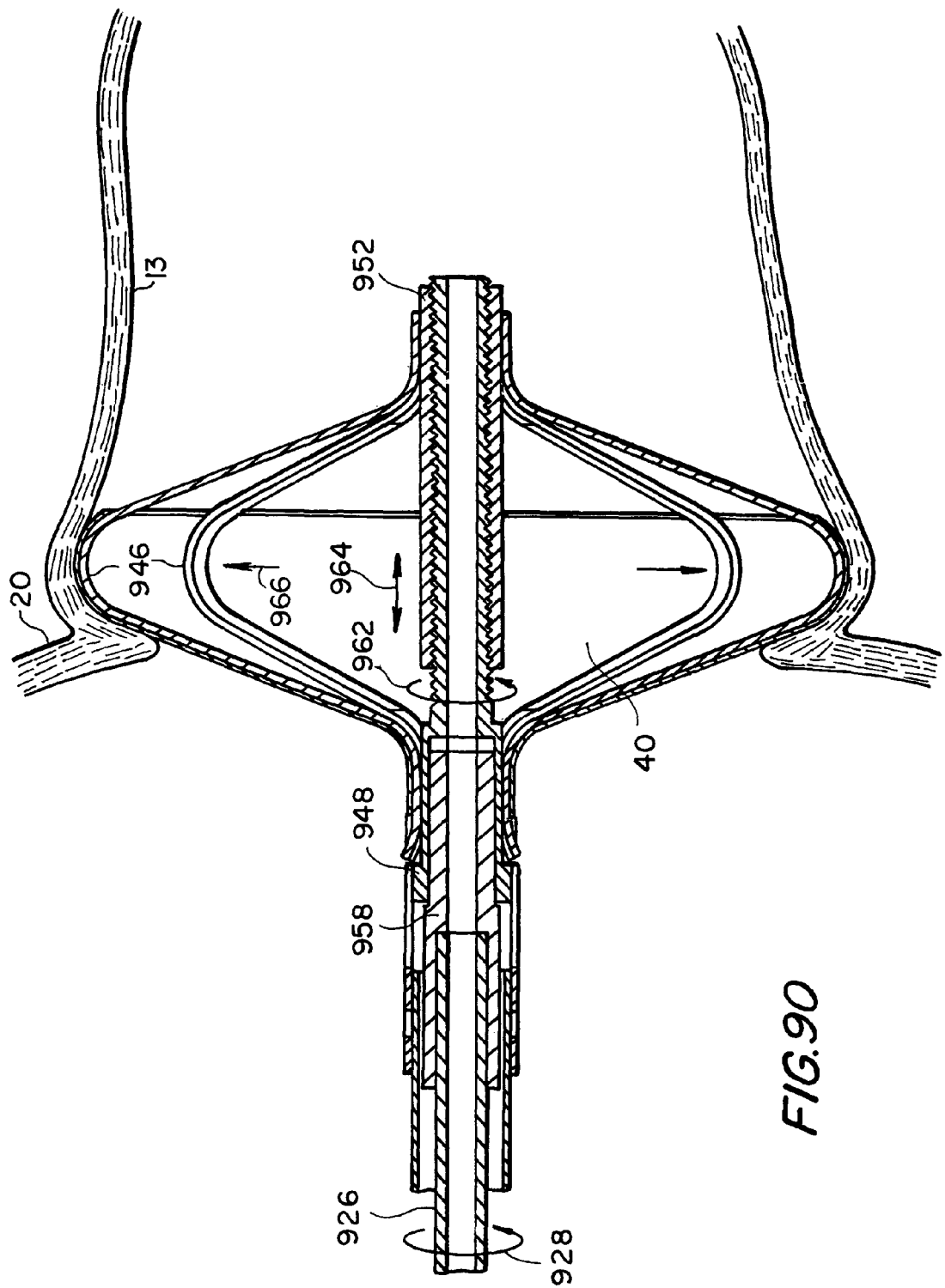
FIG. 90 is a sectional view of an early stage of a procedure in accordance with the invention.
Figure 91:
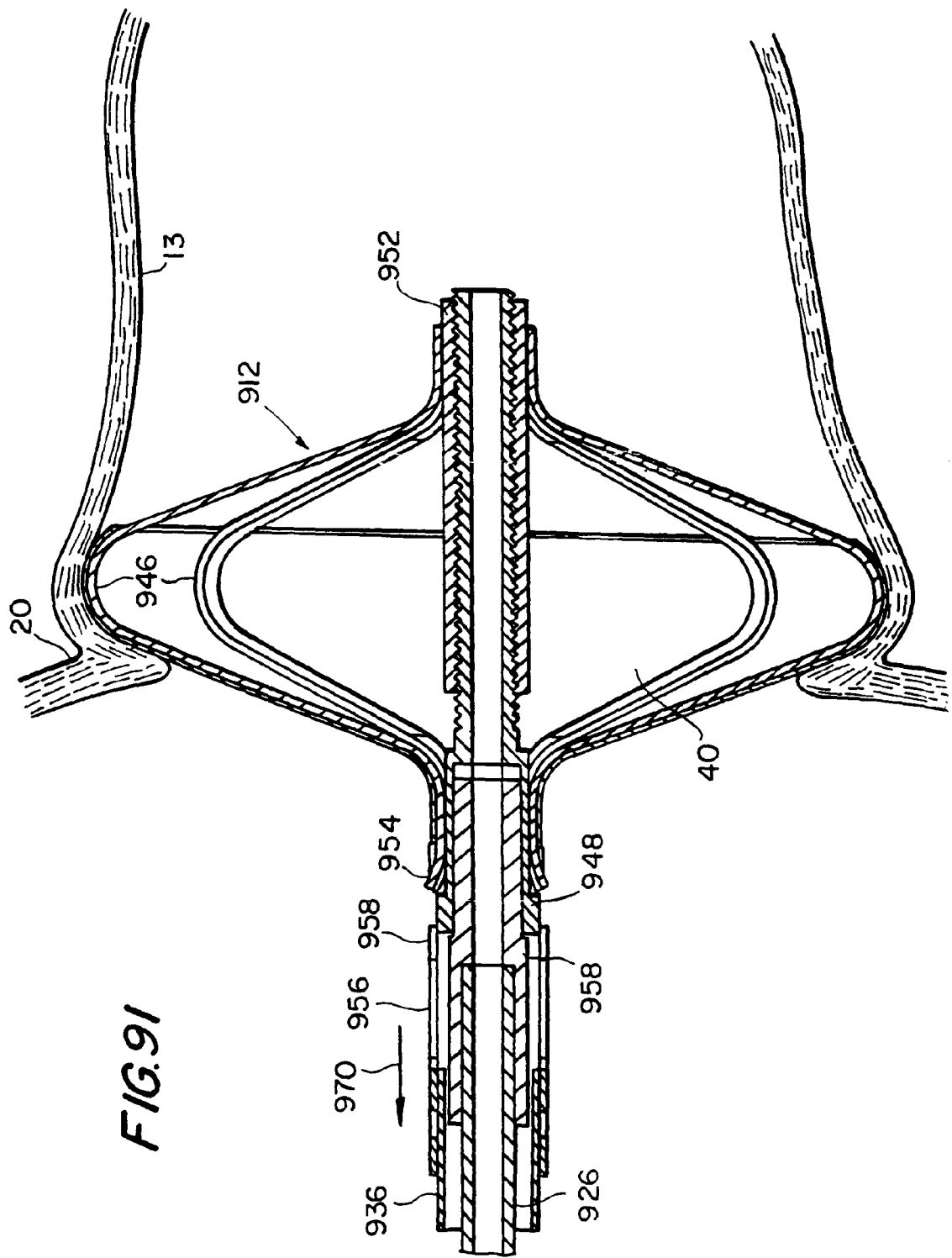
FIG. 91 is a sectional view similar to FIG. 90, illustrating a further stage in a procedure in accordance with the invention.

With reference to FIG. 88, attachment apparatus 912 may also comprise a male threaded member 948 defining outer threads 950, and a female threaded member 952 defining inner threads 953 cooperating with outer threads 950. Male threaded member 948 is longitudinally fixed adjacent the proximal portion of outer portion 941, and female threaded member 952 is longitudinally fixed adjacent the distal portion of outer portion 914. As male threaded member 948 and female threaded member 952 are longitudinally approximated by relative angular rotation therebetween, the medial portion of the longitudinal struts 946 deflect radially outwardly in a toggle-like fashion (as illustrated in FIG. 90). The cooperating threaded configuration of members 948 and 952 provides additional resistance against the longitudinal struts 946 returning to the compacted configuration of FIG. 89. A plurality of locking tabs 954 are provided adjacent the proximal portion of attachment apparatus 912, as will described herein.

The proximal end portion of elongated shaft portion 910 is configured for attachment to, and subsequent removal from, the attachment apparatus 912. More particularly, a collet 956 is attached to the distal end of outer tube 936. Collet 956 may be provided with a plurality of apertures 959, which receive locking tabs 954 therein. Driver 958 may be attached to the distal end of drive tube 926. Driver 958 preferably has a locking arrangement with respect to a longitudinal bore 960 in male threaded member 948. For example, driver 958 may have a faceted outer surface defining six planar surfaces which is received in bore 960 defining a complementary faceted surface that allows relative longitudinal movement between driver 958 and male threaded member 948, while inhibiting relative angular rotation therebetween.

Attachment apparatus 912 is positioned at least partially within the atrial appendage 13 in the compacted configuration as illustrated in FIGS. 88 and 89.

A next stage in the procedure for installing the attachment apparatus 912 and filtering membrane 40 is illustrated in FIG. 90. Once the physician has determined that the attachment apparatus 912 is properly positioned, the rotation knob 920 may be rotated in the direction indicated by arrow 924 (see, FIG. 88). Rotation of rotation knob 920 causes drive tube 926, along with driver 958, to also rotate angularly. The cooperating relationship of driver 958 within male threaded member 948 causes male threaded member 948 to rotate angularly (as indicated by arrow 962). The outer threads 950 and inner threads 953 are configured such that rotation of male threaded member 948 causes longitudinal motion of female threaded member 952 (i.e., in the direction indicated by arrow 964). To deploy the attachment apparatus 912, the male threaded member 948 is rotated to cause the female threaded member 952 to move proximally, thereby deflecting the longitudinal struts 946 radially outwardly (as indicated by arrow 966). Further rotation of the male threaded member 948 deflects the longitudinal struts 946 radially outwardly until they engage the ostium 20 or the interior wall of the atrial appendage 13.

Figure 92:
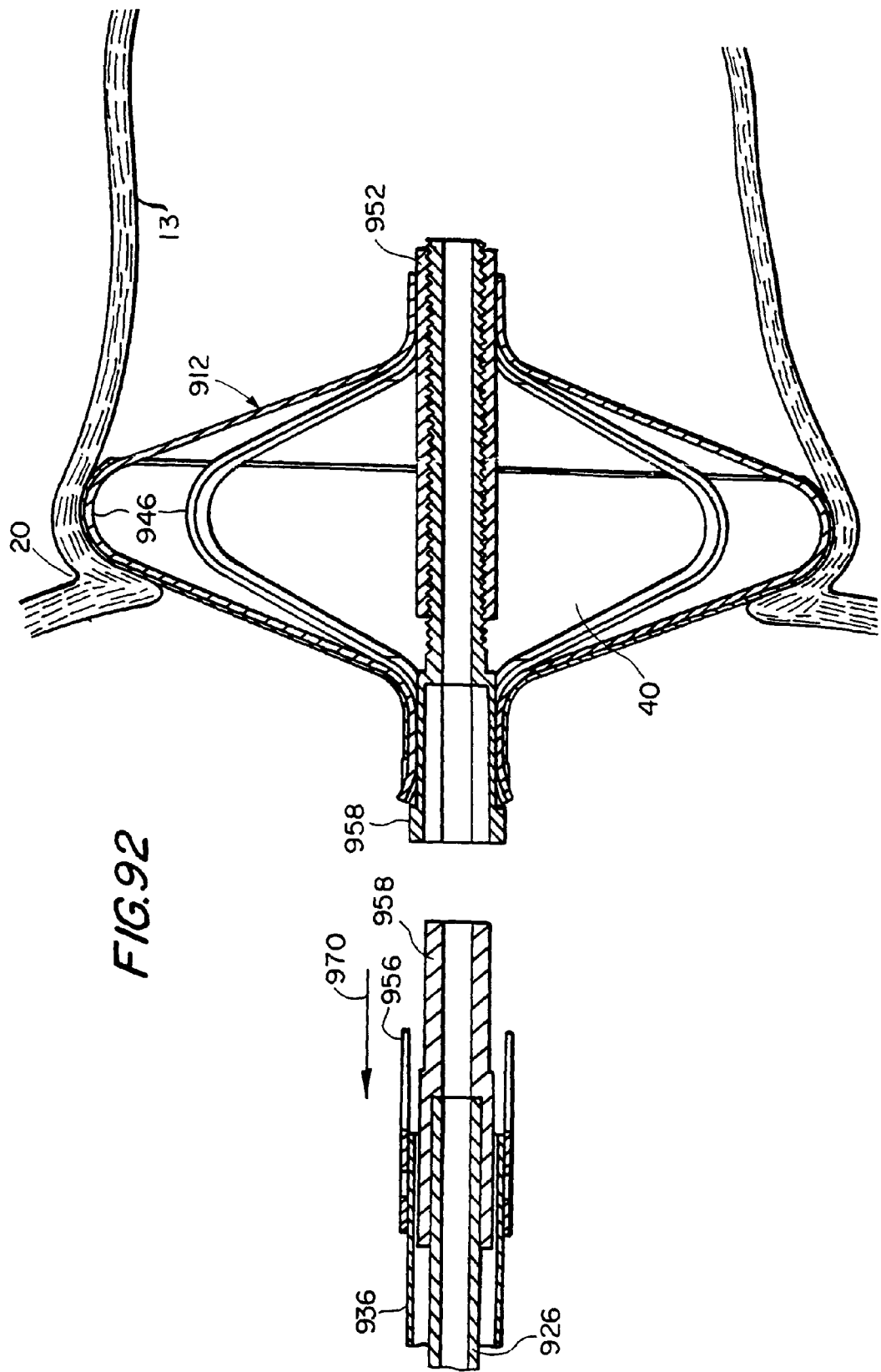
FIG. 92 is a sectional view similar to FIG. 91, illustrating a later stage in a procedure in accordance with the invention.

After deployment of the attachment apparatus 912, the deployment apparatus 910 may be detached from the attachment apparatus 912. More particularly, collet 956 is moved proximally longitudinally by moving longitudinal slider 922 proximally with respect to handle body portion 918 (as indicated by arrow 970). Longitudinal movement of collet 956 disengages locking tabs 954 from within apertures 959 provided on the distal portion of collet 958. As FIG. 92 illustrates, the drive tube 926 and driver 958 may be subsequently detached from the attachment apparatus 912 by proximal movement thereof (as indicated by arrow 970). It is also contemplated that alternative means may be provided to temporarily attach the shaft portion 910 to the attachment apparatus, such as a friction fit between the various components.

Figure 93:
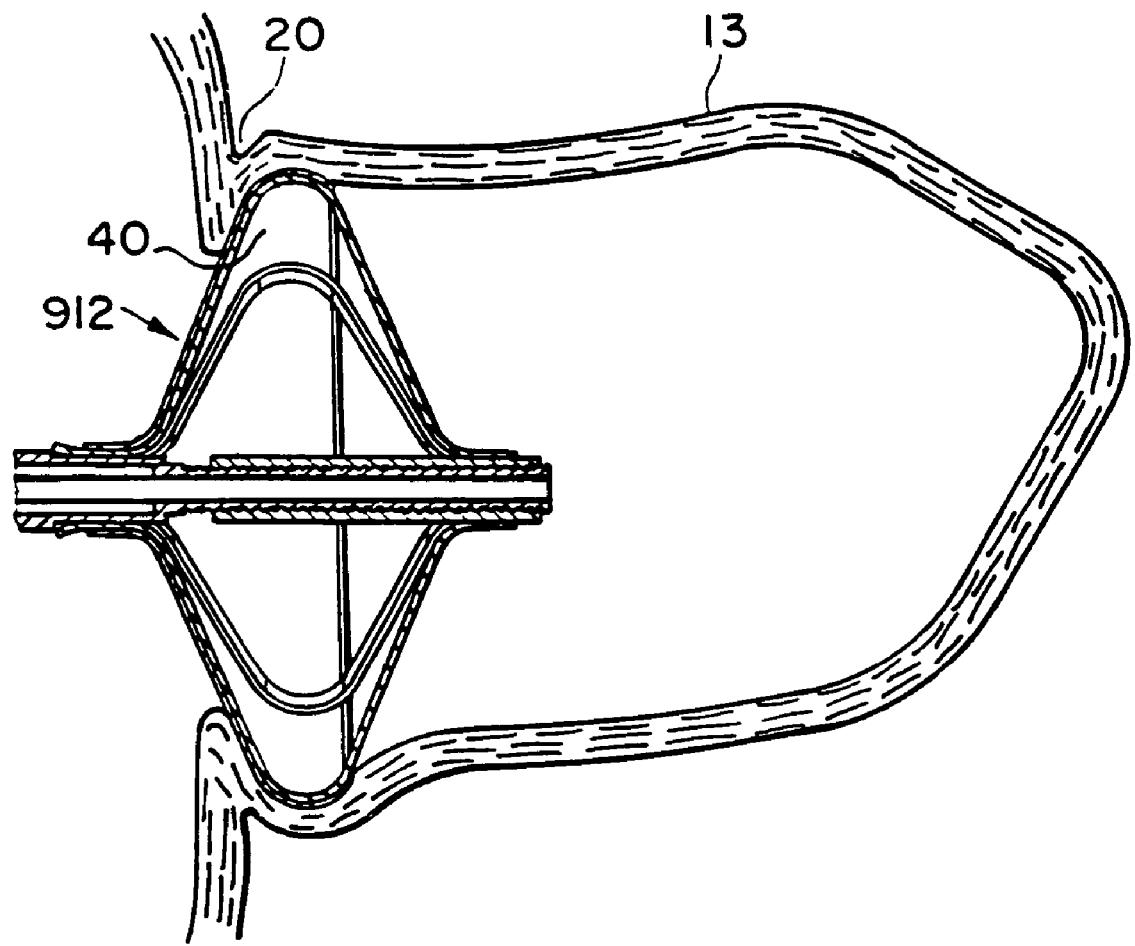
FIG. 93 is a sectional view similar to FIG. 92 at reduced scale, illustrating a later stage in a procedure in accordance with the invention.

As illustrated in FIG. 93, attachment apparatus 912 secures the filtering membrane 40 across the ostium 20 of the atrial appendage 13. Filtering membrane 40 provides the filtering characteristics described above, which allows blood to pass therethrough but substantially inhibits the passage of clots, thrombus, or emboli.

Figure 94:
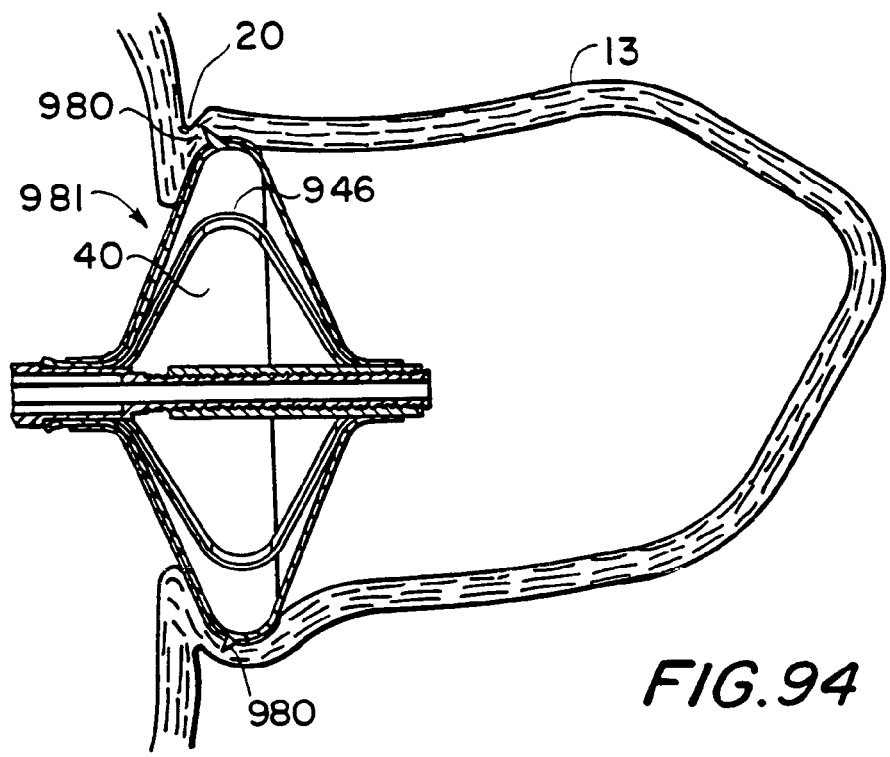
FIG. 94 is a sectional view similar to FIG. 93, illustrating another embodiment in accordance with the invention.
Figure 95:
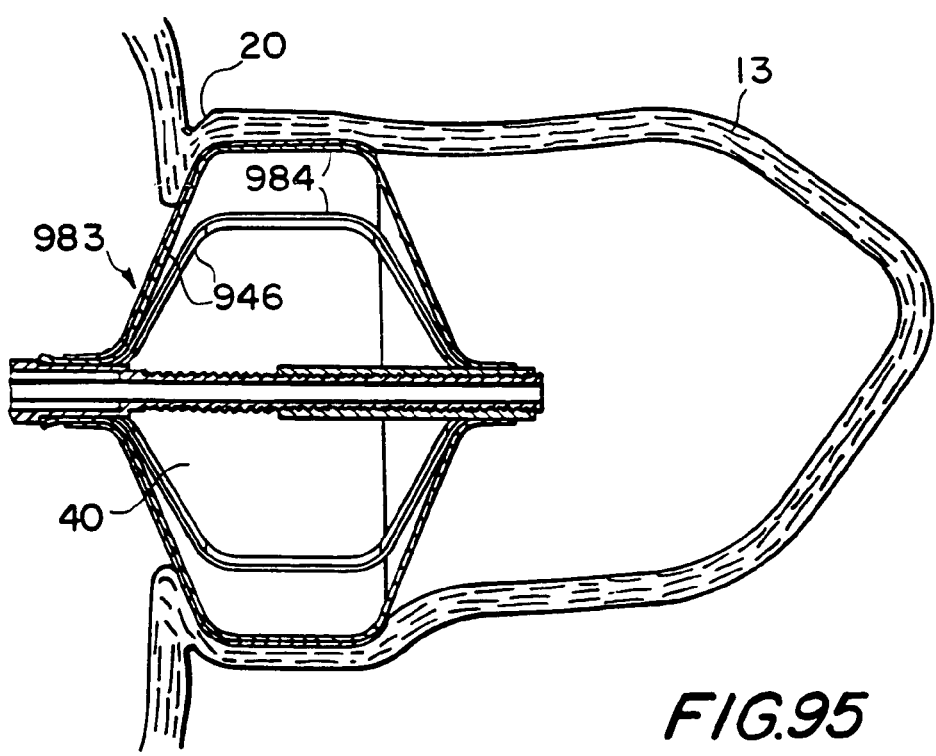
FIG. 95 is a sectional view similar to FIG. 93, illustrating yet another embodiment in accordance with the invention.

FIGS. 94-97 illustrate several additional embodiments of the attachment apparatus described herein with respect to FIGS. 88-93. FIG. 94 illustrates attachment apparatus 981, substantially similar to attachment apparatus 912, having one or more barbs 980 provided on longitudinal struts 946 in order to engage the ostium 20 or the interior wall of the atrial appendage 13. FIG. 95 illustrates attachment apparatus 983, substantially similar to attachment apparatus 912, wherein each of the longitudinal struts 946 has a substantially straight longitudinal section 984, which may provide improved conformity to the ostium 20 of the atrial appendage 13.

Figure 96:
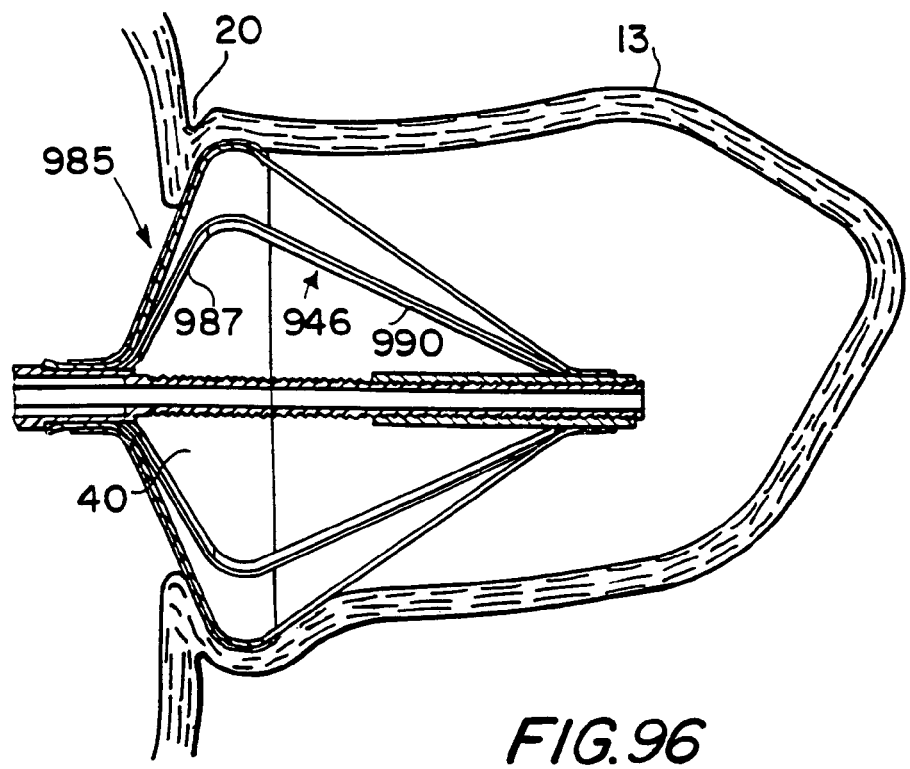
FIG. 96 is a sectional view similar to FIG. 93, illustrating still another embodiment in accordance with the invention.
Figure 97:
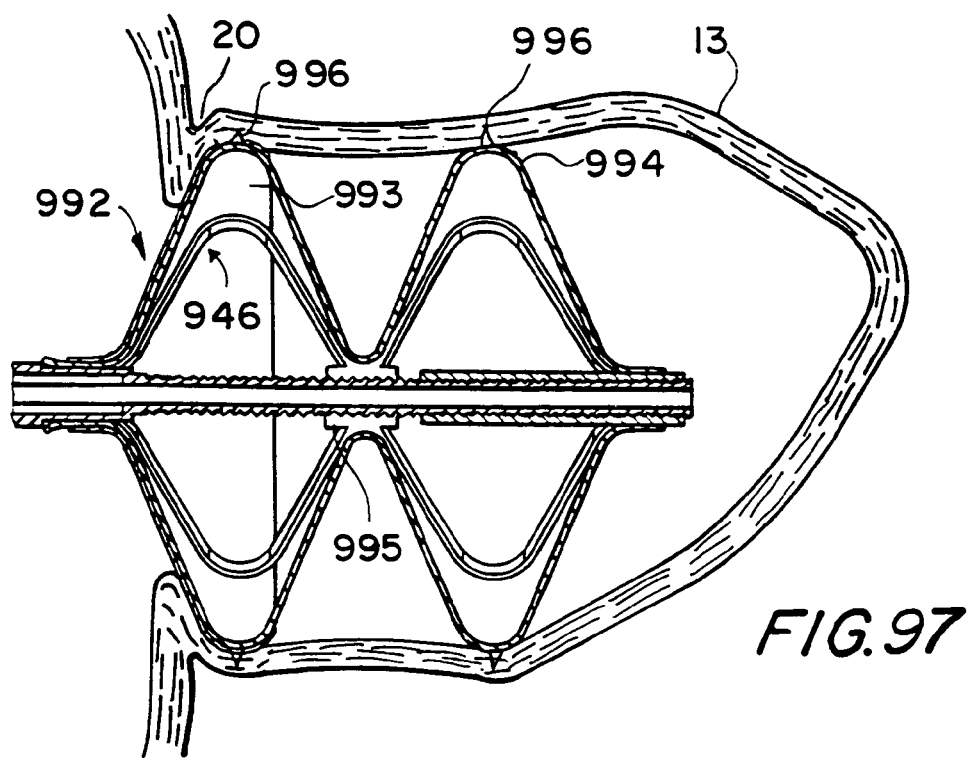
FIG. 97 is a sectional view similar to FIG. 93, illustrating a further embodiment in accordance with the invention.

FIG. 96 illustrates attachment member 985, substantially similar to attachment apparatus 912, wherein the longitudinal struts 946 have unequal length sections 987 and 990, which may provide additional stability and conformity to the ostium 20. FIG. 97 illustrates attachment apparatus 992, substantially similar to attachment apparatus 912, wherein the longitudinal struts 946 are configured to engage the ostium 20 or the interior wall of the atrial appendage 13 at a plurality of longitudinal locations, e.g., locations 993 and 994. This configuration may be achieved by attaching a portion of the longitudinal struts 946 to a slidable collar 995. In addition, the longitudinal struts 946 may be provided with barbs 996, which are configured to engage the ostium 20 and the interior wall of the atrial appendage 13 at a plurality of locations.

Figure 98:
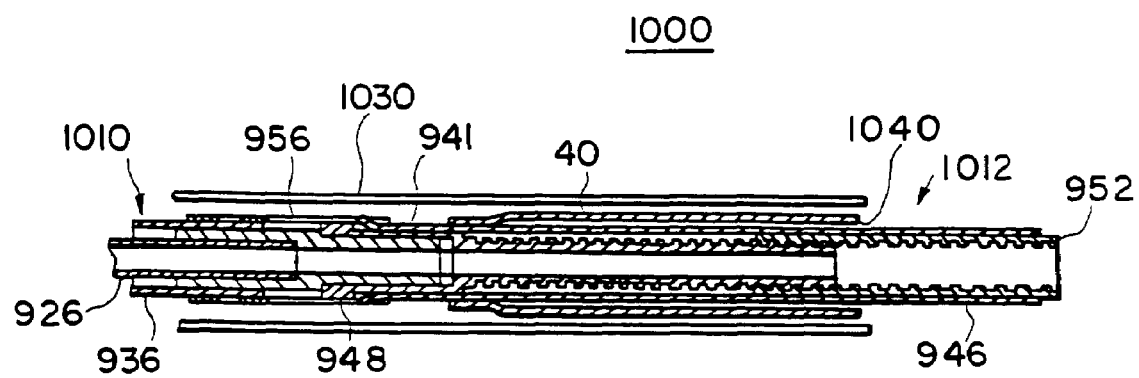
FIG. 98 is a sectional view similar to FIG. 88(b), illustrating another embodiment in accordance with the invention.
Figure 99:
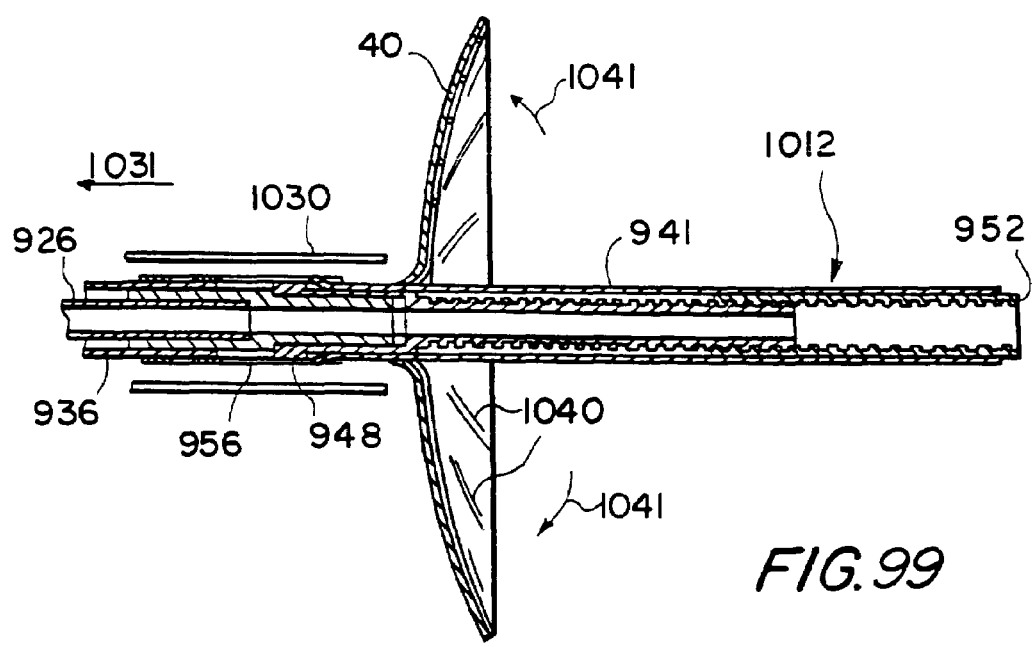
FIG. 99 is a sectional view similar to FIG. 98, illustrating a later stage in a procedure in accordance with the invention.
Figure 100:
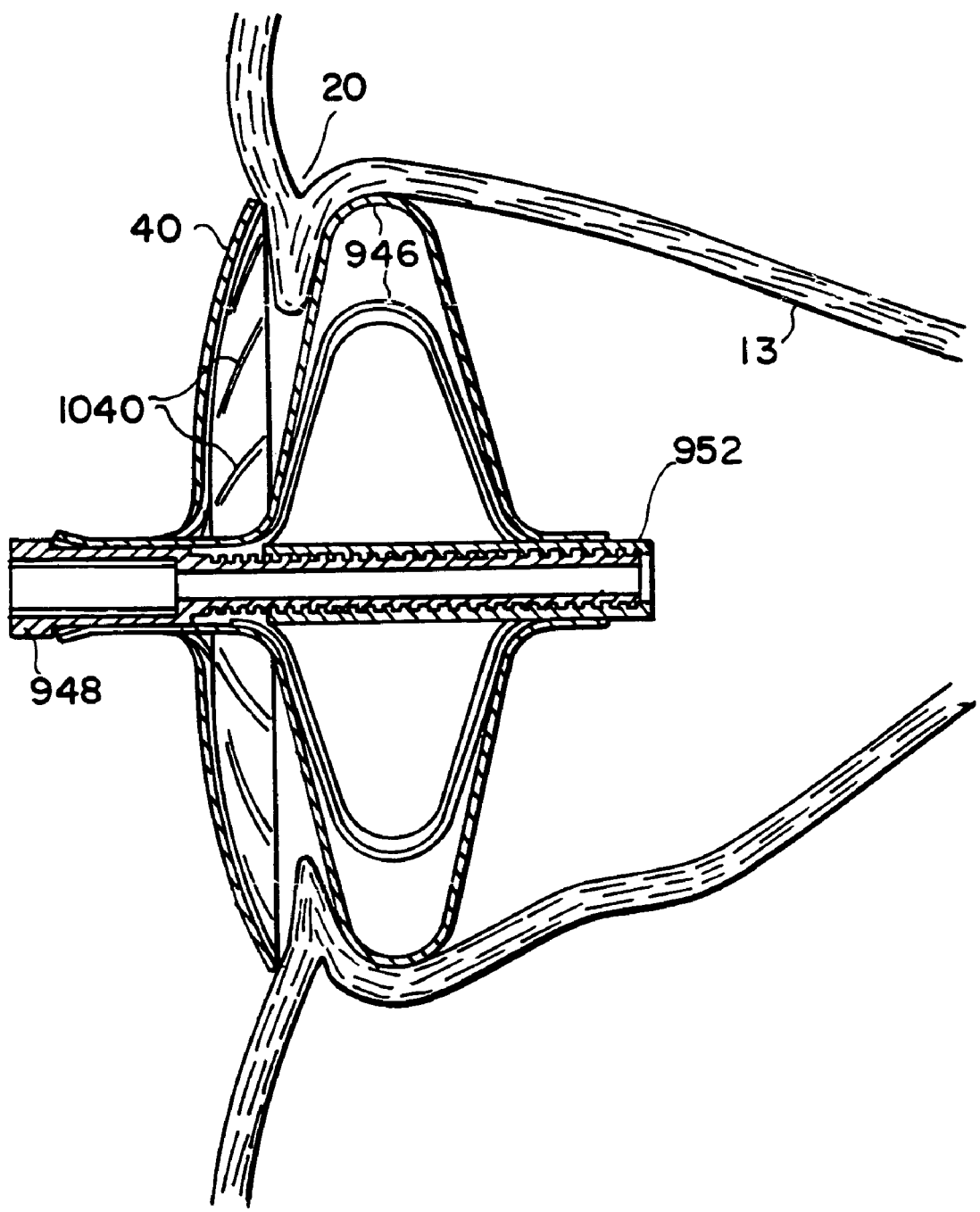
FIG. 100 is a sectional view similar to FIG. 99, illustrating a still later stage in a procedure in accordance with the invention.

Yet another embodiment is illustrated in FIGS. 98-100, and is denoted by reference number 1000. Apparatus 1000 is substantially similar to the apparatus 900 described above, with the differences noted herein. Attachment apparatus 1012 is substantially similar to attachment apparatus 912. However, filtering membrane 40 may be annularly attached to the outer portion 941 adjacent the proximal end portion thereof.

Moreover, filtering membrane 40 may be separately expandable from longitudinal struts 946. In a preferred embodiment, filtering membrane 40 is attached to an expandable membrane support frame 1040 which is preferably fabricated from a material having shape-memory characteristics, such as nitinol, and is self-expanding to radially outwardly disposed configuration.

Deployment apparatus 1010 is substantially similar to deployment apparatus 910. However, deployment apparatus 1010 may also comprise sheath 1030 which is sized to fit coaxially about the membrane 40 and the outer tube 936. Sheath 1030 retains the membrane support frame 1040 in a compacted configuration substantially parallel with the longitudinal axis of the apparatus. Sheath 1030 may be withdrawn proximally in order to permit the membrane support frame to expand radially outwardly.

FIG. 98 illustrates the attachment apparatus 1012 in an initial, compacted configuration. Sheath 1030 is coaxially disposed about the filtering membrane 40 to retain the membrane support frame 1040 substantially parallel with the longitudinal axis. Moreover, the cooperating threaded portions 952 and 948 are relatively positioned such that longitudinal struts 946 are also in the compacted, substantially cylindrical configuration. This configuration is useful for inserting and positioning the attachment apparatus 1012 adjacent the ostium 20 of the atrial appendage 13.

FIG. 99 illustrates a next step in the deployment of attachment apparatus 1012. When the attachment apparatus 1012 is positioned adjacent the ostium 20 of the atrial appendage 13, or partially disposed within the atrial appendage 13, the sheath 1030 may be withdrawn proximally (as indicated by arrow 1031). Withdrawal of sheath 1030 permits membrane support frame 1040 to expand radially outwardly (as indicated by arrows 1041), thereby outwardly expanding filtering membrane 40 therewith.

FIG. 100 illustrates a further step in the deployment of attachment apparatus. Filtering membrane 40 is positioned by the physician over the ostium 20 of the atrial appendage 13. The filtering membrane may define an outer periphery which is larger than the size of the ostium 20. Filtering membrane 40 is secured in position by expanding longitudinal struts 946 to engage the interior of the atrial appendage 13 and/or the ostium 20. Expansion of the longitudinal struts 946 is effected by rotation of the male threaded member 948 with respect to the female threaded member 952 by driver 958 (as described above with respect to FIG. 90). When the attachment apparatus 912 is securely positioned within the atrial appendage 13, the deployment apparatus 1010 may be detached from the attachment apparatus 1012, substantially as described above with respect to FIGS. 91-92. The filtering membrane 40 is secured in position by the attachment apparatus 1012 across the ostium 20. More particularly, the outer periphery of the filtering membrane 40 may be secured in direct engagement with the atrial wall surrounding the ostium 20.

The devices described above may be percutaneously delivered to the left and right atrial appendages 13, 23 respectively. The devices may have materials in them which enhance visualization or imaging by ultrasound, x-ray or other means making it easier for the device to be implanted and accurately centered with respect to the ostium 20 of the atrial appendage 13. This may consist of small beads placed strategically on the filtering membrane, the connecting elements, or on the anchors. Referring to FIG. 1 catheter 21 is seen entering the heart by way of the aorta 12 to the left ventricle 16 passing through the mitral valve 17 and then entering the left atrial appendage 13 to apply the permeable filtering membrane 40 in one of the embodiments as disclosed above. In FIG. 2 the catheter 21 enters the heart from the femoral vein, passes through the inferior vena cava 18 to the right atrium and then passes through the fossa ovalis 19 or through the septum 29 into the left atrium 11 and then approaches the left atrial appendage 13 to apply the permeable filtering membrane 40 thereto. FIG. 3 shows the catheter 21 being applied to the right atrial appendage 23. Catheter 21 may enter the heart through the jugular vein 28 or the femoral vein to the inferior vena cava 18.

It is understood that the invention may be practiced with numerous means of attaching the filtering membrane 40 across the ostium 20 of the atrial appendages 13 and 23. All of the above embodiments shown and discussed for the left atrial appendage 13 are also useable on the right atrial appendage 23. Any combination of the attachment means with adhesives, prongs, cylindrical structures, anchors, disks, tethers or springs may be used. The filtering membrane may also be inside of the atrial appendages 13 and 23, or may penetrate the atrial appendage and provide a means to securely lock the filtering membrane device into place. Other means of providing a filtering membrane for allowing blood flow therethrough and substantially inhibiting blood clots from exiting out of the atrial appendages not listed herein may also be used.

Obviously, many modifications and variations of the present invention are possible in light of the above teachings. It is therefore to be understood that, within the scope of the appended claims, the invention may be practiced otherwise than as specifically described.

What is claimed is:

1. Apparatus for permanent placement across an ostium of a left atrial appendage in a patient, comprising:

a permanent membrane configured to extend across the ostium of the left atrial appendage; and a support structure having a first deployed shape configuration having a radially enlarged medial portion to permanently engage the interior wall of the left atrial appendage, and having a second retracted shape configuration having a radially reduced medial portion to fit within a delivery catheter in an undeployed state;

said support structure having a plurality of strut like limbs defining an exterior diameter when in the deployed shape and defining a retracted diameter in the undeployed state, each strut like limb expanding from and defining a first distal hub area where radially deployable strut like limbs are gathered together in both the deployed and retracted state, a second medial hub area where deployable strut like limbs are gathered together in both the deployed and undeployed state in a necked down ring, and a third proximal hub area facing the left ventricle when in the deployed state, said support structure having a membrane support frame and associated membrane wherein the filtering membrane is attached to the support structure extending across the ostium of the left atrial appendage when the deployable medial portion engages the interior of the left atrial appendage the strut like limbs coming together at the third proximal hub area.

2. Apparatus as defined in claim 1, wherein the support structure comprises a plurality of strut like fingers each having a first end portion, a second end portion, and a medial portion, and wherein the medial portion of each finger is radially outwardly expanded in the second configuration and the first end portion and second end portion meet at said first distal hub area and said second medial hub area.

3. Apparatus as defined in claim 2, wherein the support structure further comprises first and second cooperating threaded members configured for relative angular rotation, wherein each cooperating threaded member is attached to a respective first and second end portion of each finger, and wherein the first and second end portions of said fingers are approximated by said relative angular rotation between the cooperating threaded members.

4. Apparatus as defined in claim 3, further comprising:
an actuator configured to expand the plurality of fingers by angularly rotating one of the cooperating threaded members about the longitudinal axis.

5. Apparatus as defined in claim 4, wherein the actuator further comprises an outer tube configured for releasable attachment to the support structure.

6. Apparatus as defined in claim 5, wherein the support member comprises a tab structure and the outer tube defines an aperture at an end portion thereof, and wherein the outer tube is releasably attached to the support member by engagement of the tab structure in the aperture.

7. Apparatus as defined in claim 5, wherein the outer tube is releasably attached to the support member by a frictional fit.

8. Apparatus as defined in claim 1, wherein the strut like fingers are fabricated of stainless steel.

9. Apparatus as defined in claim 1, wherein the strut like fingers are fabricated of nitinol.

10. Apparatus as defined in claim 1, wherein the strut like fingers further include proximate said medial portion a barbed portion configured to engage an interior wall of the atrial appendage.

11. The apparatus of claim 1 further comprising an actuator configured to remotely radially outwardly expand the support structure.

12. The apparatus of claim 11, wherein the support structure comprises a plurality of strut like fingers and wherein the actuator comprises a drive member configured to expand the plurality of fingers by angularly rotating one of the cooperating threaded members about the longitudinal axis.

13. The apparatus of claim 1 wherein the support structure is a membrane support frame that is radially outwardly expandable to engage the atrial wall surrounding the ostium, and wherein the filtering membrane is attached to the membrane support frame to extend over the ostium of the left atrial appendage.

14. Apparatus as defined in claim 13, wherein the membrane support frame is fabricated from a material having shape-memory characteristics.

15. Apparatus as defined in claim 13, wherein the membrane support frame is elastically expandable.

* * * * *